United States Patent
Svendsen et al.

(10) Patent No.: US 12,258,571 B2
(45) Date of Patent: Mar. 25, 2025

(54) METHODS AND COMPOSITIONS FOR INDUCIBLE EXPRESSION OF NEUROTROPHIC FACTORS

(71) Applicant: CEDARS-SINAI MEDICAL CENTER, Los Angeles, CA (US)

(72) Inventors: Clive Svendsen, Pacific Palisades, CA (US); Joshua Breunig, Los Angeles, CA (US); Aslam Akhtar, Torrance, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 1074 days.

(21) Appl. No.: 16/979,640

(22) PCT Filed: Mar. 15, 2019

(86) PCT No.: PCT/US2019/022595
§ 371 (c)(1),
(2) Date: Sep. 10, 2020

(87) PCT Pub. No.: WO2019/178550
PCT Pub. Date: Sep. 19, 2019

(65) Prior Publication Data
US 2021/0024955 A1 Jan. 28, 2021

Related U.S. Application Data

(60) Provisional application No. 62/773,752, filed on Nov. 30, 2018, provisional application No. 62/644,332, filed on Mar. 16, 2018.

(51) Int. Cl.
*C12N 15/86* (2006.01)
*A61K 31/65* (2006.01)
*A61K 35/30* (2015.01)
*A61K 38/18* (2006.01)
*C07K 14/475* (2006.01)
*C12N 5/079* (2010.01)

(52) U.S. Cl.
CPC ........... *C12N 15/86* (2013.01); *A61K 31/65* (2013.01); *A61K 35/30* (2013.01); *A61K 38/185* (2013.01); *C07K 14/4756* (2013.01); *C12N 5/0618* (2013.01); *C12N 2506/45* (2013.01); *C12N 2830/003* (2013.01); *C12N 2830/205* (2013.01)

(58) Field of Classification Search
CPC .. C12N 15/86; C12N 5/0618; C12N 2506/45; C12N 2830/003; C12N 2830/205; A61K 31/65; A61K 35/30; A61K 38/185; C07K 14/4756

See application file for complete search history.

(56) References Cited

U.S. PATENT DOCUMENTS

| | | |
|---|---|---|
| 11,466,290 B2 | 10/2022 | Breunig et al. |
| 2003/0084468 A1 | 5/2003 | Economides et al. |
| 2003/0228295 A1 | 12/2003 | Svendsen |
| 2010/0077495 A1 | 3/2010 | Davis et al. |
| 2010/0240133 A1 | 9/2010 | Brivanlou et al. |
| 2012/0107938 A1 | 5/2012 | Lopez-Rios et al. |
| 2013/0115692 A1 | 5/2013 | Trono et al. |
| 2015/0044187 A1 | 2/2015 | Visel et al. |
| 2016/0060651 A1 | 3/2016 | Alphey |
| 2017/0137781 A1 | 5/2017 | Qiang et al. |
| 2017/0216456 A1 | 8/2017 | Alexander et al. |
| 2017/0274048 A1 | 9/2017 | Neves et al. |
| 2018/0021383 A1 | 1/2018 | George et al. |
| 2019/0390222 A1 | 12/2019 | Breunig et al. |
| 2022/0304286 A1 | 9/2022 | Breunig et al. |

(Continued)

FOREIGN PATENT DOCUMENTS

| | | |
|---|---|---|
| AU | 2016389495 A1 | 8/2018 |
| AU | 2019236288 A1 | 9/2020 |
| CA | 3012042 A1 | 8/2017 |

(Continued)

OTHER PUBLICATIONS

Sareen et al ("Human neural progenitor cells generated from induced pluripotent stem cells can survive, migrate, and integrate in the rodent spinal cord," J Comp Neurol. Aug. 15, 2014; 522(12): 2707-2728 (Year: 2014).*
Wang et al ("Neuroprotective Effects of Glial Cell Line-Derived Neurotrophic Factor Mediated by an Adeno-Associated Virus Vector in a Transgenic Animal Model of Amyotrophic Lateral Sclerosis," The Journal of Neuroscience, Aug. 15, 2002, 22(16):6920-6928) (Year: 2002).*
Akhtar et al. ("A Transposon-Mediated System for Flexible Control of Transgene Expression in Stem and Progenitor-Derived Lineages" Stem Cell Reports. Mar. 10, 2015; 4(3): 323-331) (Year: 2015).*

(Continued)

*Primary Examiner* — Valarie E Bertoglio
(74) *Attorney, Agent, or Firm* — NIXON PEABODY LLP

(57) ABSTRACT

Delivery of glial cell line-derived neurotrophic factor (GDNF) has provided benefits to Parkinsonian patients and is currently being tested in a Phase 1/2a clinical trial for ALS patients. However, chronic trophic factor delivery prohibits dose adjustment or shut off in the event of side effects. To address this, the Inventors engineered a stably integrating, third-generation doxycycline-regulated vector, allowing inducible and reversible expression of a therapeutic molecule Human iPSC-derived neural progenitors were stably transfected with the vector, expanded and transplanted into the adult mouse brain. The Inventors observed that the addition and withdrawal of doxycycline led to GDNF expression that could be induced and reversed multiple times, demonstrating that doxycycline can penetrate the graft and regulate transgene expression in vivo. The Inventors' findings provide a proof of concept for combining gene and stem cell therapy for effective modulation of ectopic protein expression in transplanted cells.

19 Claims, 12 Drawing Sheets

Specification includes a Sequence Listing.

(56) References Cited

U.S. PATENT DOCUMENTS

2023/0084201 A1  3/2023  Breunig et al.

FOREIGN PATENT DOCUMENTS

| | | |
|---|---|---|
| CA | 3092284 A1 | 9/2019 |
| CN | 108884472 A | 11/2018 |
| CN | 111867617 A | 10/2020 |
| EP | 2977449 A1 | 1/2016 |
| EP | 3408396 A1 | 12/2018 |
| EP | 3765058 | 1/2021 |
| HK | 40001420 A | 2/2020 |
| JP | 2019511243 A | 4/2019 |
| JP | 2021518365 A | 8/2021 |
| KR | 20180101535 A | 9/2018 |
| KR | 20200132957 A | 11/2020 |
| WO | 2011001247 A2 | 1/2011 |
| WO | 2014127289 A1 | 8/2014 |
| WO | 2014204724 A1 | 12/2014 |
| WO | 2017079673 A1 | 5/2017 |
| WO | 2017131926 A1 | 8/2017 |
| WO | 2019/178550 A1 | 9/2019 |
| WO | 2020257205 A1 | 12/2020 |

OTHER PUBLICATIONS

Martinez et al ("Stem-cell transplantation into the frontal motor cortex in amyotrophic lateral sclerosis patients," Cytotherapy (2009) vol. 11, No. 1, 2634). (Year: 2009).*
Baloh (2022, Nature Medicine, 28:1813-1822).*
Akhtar (2018, Stem Cell Reports, 10:1696-1704).*
Zhang et al ("Human Neural Stem Cells with GDNF Site-Specific Integration at AAVS1 by Using AAV Vectors Retained Their Stemness," Neurochemical Research (2018) 43:930-937) (Year: 2018).*
Osterwalder et al ("Dual RMCE for efficient re-engineering of mouse mutant alleles;" Nature Methods, Nature America, 2010 (Year: 2010).*
Klein, S. M. et al. GDNF delivery using human neural progenitor cells in a rat model of ALS. Hum. Gene Ter. 16, 509-521 (2005). (Year: 2005).*
Suzuki, M. et al. GDNF secreting human neural progenitor cells protect dying motor neurons, but not their projection to muscle, in a rat model of familial ALS. PLoS ONE 2, e689 (2007). (Year: 2007).*
International Search Report and Written Opinion for PCT/US2019/022595 dated Jun. 10, 2019, 18 pages.
Breunig et al., Platform presentation, SNO Meeting, 2013.
Bruenig, et al., Ets Factors Regulate Neural Stem Cell Depletion and Gliogenesis in Ras Pathway Glioma, Cell Reports, Jul. 14, 2015, 12:258-271.
Cobellis et al., Tagging Genes with Cassette-Exchange Sites, Nucleic Acids Research, 2005, vol. 33(4), pp. 1-7.
Lauth et al., Stable and Efficient Cassette Exchange Under Non-Selectable Conditions by Combined Use of Two Site-Specific Recombinases, Nucleic Acids Research 2002, vol. 30(21).
Akhtar et al., A Transposon-Mediated System for Flexible Control of Transgene Expression in Stem and Progenitor-Derived Lineages, Stem Cell Reports, 2015, vol. 4, pp. 323-331.
International Search Report and Written Opinion for PCT/US2016/069442 dated Jun. 2, 2017, 13 pages.
Galli et al., Distinct Roles of Hand2 in Initiating Polarity and Posterior Shh Expression during the Onset of Mouse Limb Bud Development, PLoS Genetics, 2010, vol. 6(4), pp. 1-14.
Hohenstein et al., High-Efficiency Rosa26 Knock-in Vector Construction for Cre-Regulated Overexpression and RNAi, PathoGenetics, 2008, vol. 1(1), pp. 1-10.
Lopez-Rios et al., GLI3 Constrains Digit Number by Controlling Both Progenitor Proliferation and BMP-Dependent Exit to Chondrogenesis, Developmental Cell, 2012, pp. 1-70.
Osterwalder et al., Dual RMCE for Efficient Re-Engineering of Mouse Mutant Alleles, Nature Methods, 2010, pp. 1-12.
Osterwalder et al., Next Generation Engineering of Conditional Mouse Alleles with loxP and FRT sites by Dual RMCE, Protocol Exchange, 2010, Abstract Only.
Osterwalder et al., Genome-Wide Identification of Hand2 Target Regions in Mouse Embryos using dRMCE, a New Genetic Tool, Basel, 2012, pp. 1-203.
Zeller et al., Gene Cutting and Pasting Just Got a Whole Lot Faster, Nature Methods, 2010, vol. 7(11), p. 861.
Partial Supplementary European Search Report of EP 16888589.5, Issued Jun. 5, 2019, 12 Pages.
Extended European Search Report of EP 16888589.5, Issued Sep. 5, 2019, 9 Pages.
Chen et al., Engineering Human Stem Cell Lines with Inducible Gene Knockout using CRISPR/Cas9, Cell Stem Cell, 2015, vol. 17(2), pp. 233-244.
International Search Report and Written Opinion for PCT/US2020/037946 dated Sep. 16, 2020, 14 pages.
Zhang et al., Human Neural Stem Cells with GDNF Site-Specific Integration at AAVS1 by using AAV Vectors Retained Their Stemness, Neurochem Res, 2018, vol. 43(4), pp. 930-937.
Karimova et al., Discovery of Nigri/nox and Panto/pox site-specific recombinase systems facilities advanced genome engineering, Sci Rep, 2016, vol. 6(30130), pp. 1-13.
De Groot et al., In vivo induction of glial cell proliferation and axonal outgrowth and myelination by brain-derived neurotrophic factor, Mol Endocrinol, 2006, vol. 20(11), pp. 2987-2998.
Sullivan et al., Neurotrophic factor therapy for Parkinson's disease: past, present and future, Neural Regen Res, 2016, vol. 11(2), pp. 205-207.
Guan et al., Establishing isogenic inducible cell lines using founder reporter lines and recombinase-mediated cassette exchange, Biotechniques, 2013, vol. 55(5), pp. 233-242.
EP 19768063.0 European Extended Search Report dated Nov. 24, 2021, 10 pages.
Abbasi et al., Inducible Expression of GDNF in Transplanted iPSC-Derived Neural Progenitor Cells, Stem Cell Reports, 2018, vol. 10(6), pp. 1696-1704.
Suzuki et al., GDNF Secreting Human Neural Progenitor Cells Protect Dying Motor Neurons, but Not Their Projection to Muscle, in a Rat Model of Familial ALS, PLOS ONE, 2007, vol. 2(8).
Supplementary European Search Report for EP 20827879 dated Sep. 13, 2023.
Anderson et al., Flp and Cre expressed from Flp-2A-Cre and Flp-IRES-Cre transcription units mediate the highest level of dual recombinase-mediated cassette exchange, Nucleic Acids Research, 2012, vol. 40(8), vol. e62, pp. 1-9.
O'Brien et al., Single Copy Transgene Integration in a Transcriptionally Active Site for Recombinant Protein Synthesis, Biotechnology Journal, 2018, vol. 13(10), pp. 1-10.
Grausam et al., Expanding a Pediatric Glioma Toolkit of Genetic Manipulation to Generate Tertiary Modes of Inducible Recombinase Expression, Neuro-Oncology, 2019, Abstract only.
Meinke et al., Cre Recombinase and Other Tyrosine Recombinases, Chemical Reviews, 2016, vol. 116, pp. 12785-12820.
Turan et al., Recombinase-mediated cassette exchange (RMCE)—A rapidly-expanding toolbox for targeted genomic modifications, Gene, 2013, vol. 515(1), pp. 1-27.
Ordovas et al., Efficient Recombinase-Mediated Cassette Exchange in hPSCs to Study the Hepatocyte Lineage Reveals AAVSI Locus-Mediated Transgene Inhibition, Stem Cell Reports, 2015, vol. 5(5), pp. 918-931.
Muzumdar et al., A Global Double-Fluorescent Cre Reporter Mouse, Genesis, vol. 45(9), 2007, pp. 593-605.
Shah et al., Target-specific variants of Flp recombinase mediate genome engineering reactions in mammalian cells, 2015, the Febs Journal, vol. 282(17), pp. 3323-3333.
Chinese Office Action for CN2019800196836 dated Jun. 26, 2024, 18 pages.
Chen et al., Intrastriatal GDNF gene transfer by inducible lentivirus vectors protects dopaminergic neurons in a rat model of parkinsonism, Experimental Neurology, 2014 261:87-96.

* cited by examiner pDonor-Teton3g-2a-TagBFP-V5-nls-p2A-puroR WPRE_Insulated mpclover-2a-luc2pest-2a-gdnf wpre
15,067 bp

METHODS AND COMPOSITIONS FOR INDUCIBLE EXPRESSION OF NEUROTROPHIC FACTORS

CROSS-REFERENCE TO RELATED APPLICATIONS

This application is a National Phase of International Application No. PCT/US2019/022595, filed Mar. 15, 2019, which designated the U.S. and that International Application was published under PCT Article 21 (2) in English, which claims the benefit under 35 U.S.C. § 119 (e) to U.S. provisional patent application No. 62/644,332, filed Mar. 16, 2018, and to U.S. provisional patent application No. 62/773, 752, filed on Nov. 30, 2018, which are incorporated herein by reference in its entirety. A2,AMD

STATEMENT REGARDING FEDERALLY SPONSORED RESEARCH OR DEVELOPMENT

This invention was made with government support under Grant No. CA202900 awarded by the National Institutes of Health. The government has certain rights in the invention.

FIELD OF THE INVENTION

Described herein are cells engineered to express ectopic proteins in an inducible manner. The claimed invention relates to the technical field of regenerative medicine and degenerative diseases, including neurodegeneration.

BACKGROUND

Amyotrophic lateral sclerosis (ALS) is a rapidly progressing disease, hence constitutive trophic factor release may be sufficient without considering any long term effects of continual administration of the drug. In contrast, many other neurological diseases with a longer life span may not require sustained growth factor secretion, or it may be detrimental with chronic delivery. Indeed, postmortem analysis of a Parkinsonian patient only temporarily receiving GDNF in the caudate putamen showed persistent neuronal sprouting that may explain maintained effects after GDNF delivery cessation. Furthermore, constitutive growth factor release does not allow for cessation in the event of a contraindication. For instance, trials have reported that some patients receiving GDNF developed Lhermitte's symptoms. In addition, sustained GDNF expression can cause aberrant sprouting and desensitization of the targeted neurons. Importantly, these effects were reversed upon GDNF cessation. Overall, there is a clear rationale for growth factor regulation in these types of clinical applications and a great need in the art for compositions and techniques achieving these aims.

Combined cell and gene therapy approaches to both rejuvenate cellular niches and provide therapeutic molecules to diseased host cells is a promising new treatment approach for neurogical disorders. The Inventors' group has extensively used human neural progenitor cells genetically engineered to stably produce GDNF, and shown that they survive, migrate, release GDNF and protect degenerating neurons. Critically, these cells have been confirmed to be safe and non-tumorigenic and as such are now being used in the first-ever cell and gene therapy FDA-approved Phase 1/2a clinical trial for the protection of motor neurons in ALS patients.

External factors such as mifepristone, rapamycin or tetracycline (Tet, and its analog doxycycline, dox) can be used to regulate gene expression. Neurotrophic factors such as GDNF delivered by direct gene transfer in the rodent has been regulated, but this has yet to be accomplished for engrafted human neural cells engineered to release neurotrophic factors such as GDNF. Finally, the need for repeated on-off flexibility may be required, yet the current standard in the field is to only induce or repress a gene over a single cycle.

Described herein is a dox-mediated method for inducing and reversing GDNF expression in human induced pluripotent stem cell (iPSC)-derived neural progenitor cells (iNPCs) transplanted to the adult mouse brain. The Inventors show that dox administration can inducibly and reversibly modulate GDNF secretion in vivo. As such, the Inventors demonstrate that the powerful technologies of iPSCs, ex vivo cell engineering, and gene regulation can be combined as a unique approach to treat disorders where regulated protein delivery may be desired.

SUMMARY OF THE INVENTION

Described herein is a method of treatment, including administering a quantity of cells to a subject afflicted with a disease or condition, wherein the cells express a therapeutic protein or peptide, and further wherein the cells, therapeutic protein or peptide, or both, are capable of treating the disease or condition. In other embodiments, the cells are neural lineage cells. In other embodiments, the neural lineage cells are neural progenitor cells. In other embodiments, the neural progenitor cells are derived from induced pluripotent stem cells (iPSCs). In other embodiments, the cells express an expression cassette from one or more vectors. In other embodiments, the cells expressing the expression cassette from the one or more vectors have been nucleofected, transfected, or electroporated. In other embodiments, the one or more vectors comprise a piggyBac vector, a pBase vector, or both. In other embodiments, the piggyBac vector includes at least two promoters, wherein at least one promoter is inducible. In other embodiments, the at least one inducible promoter is polycistronic. In other embodiments, the at least one inducible, polycistronic promoter is bi-directional. In other embodiments, the expression cassette is genomically integrated. In other embodiments, the expression cassette encodes the therapeutic protein or peptide. In other embodiments, the therapeutic protein or peptide includes a neurotrophic factor.

In other embodiments, the neurotrophic factor includes glial derived neurotrophic factor (GDNF). In other embodiments, the disease or condition is a neurodegenerative disease. In other embodiments, the neurodegenerative disease is amyotrophic lateral sclerosis (ALS). In other embodiments, administering a quantity of cells includes injection. In other embodiments, the method includes administration of tetracycline, an analog or derivative thereof, including for example, doxycycline.

Also described herein is a method, including providing a quantity of induced pluripotent stem cell (iPSC) derived cells and introducing at least two vectors into the iPSC derived cells. In other embodiments, the iPSC derived cells are neural progenitor cells. In other embodiments, introducing at least two vector includes one or more of: nucleofection, transfection and electroporation. In other embodiments, the at least two vectors comprise a piggyBac vector and a pBase vector. In other embodiments, the piggyBac vector includes an expression cassette, including a constitutive promoter, an inducible promoter including a tet responsive element, and a sequence encoding a protein or peptide, two transposon elements, wherein the two transposon elements flank the expression cassette. In various embodiments, the inducible promoter is a bi-directional polycistronic promoter. In other embodiments, the protein or peptide includes a neurotrophic factor. In other embodiments, the neurotrophic factor includes glial derived neurotrophic factor (GDNF). Further described herein is a a quantity of cells made by the aforementioned method, wherein the iPSC derived cells express a genomically integrated expression cassette.

Described herein is a method, including administering a quantity of induced pluripotent stem cell derived neural progenitor cells (iNPCs) to a subject afflicted with a neurodegenerative disease, wherein the cells inducibly express a neurotrophic factor capable of treating the disease. In other embodiments, the iNPCs express a genomically integrated expression cassette introduced by nucleofection, the expression cassette including a constitutive promoter, an inducible promoter including a tet response element, and a sequence encoding glial derived neurotrophic factor (GDNF). In various embodiments, the inducible promoter is a bi-directional polycistronic promoter. In other embodiments, the method includes administration of tetracycline, an analog or derivative thereof, including for example, doxycycline.

Also described herein is a quantity of neural progenitor cells capable of inducible expression of glial derived neurotrophic factor (GDNF) including a quantity of induced pluripotent stem cell derived neural progenitor cells (iNPCs), wherein the iNPCs express a genomically integrated expression cassette including a constitutive promoter, an inducible promoter including a tet response element, and a sequence encoding GDNF. In various embodiments, the inducible promoter is a bi-directional polycistronic promoter. Further described herein is a method of treating amyotrophic lateral sclerosis (ALS) using the aforementioned cells. In various embodiments, the genomically integrated expression cassette lacks a transposon derived sequence within 10 kb of the genomically integrated expression cassette. In various embodiments, the genomically integrated expression cassette lacks a transposon derived sequence within 1 kb of the genomically integrated expression cassette. In various embodiments, the genomically integrated expression cassette lacks a viral derived sequence within 10 kb of the genomically integrated expression cassette. In various embodiments, the genomically integrated expression cassette lacks a viral derived sequence within 1 kb of the genomically integrated expression cassette.

Also described herein is a method of increasing glial derived neurotrophic factor (GDNF) levels in the central nervous system of an individual afflicted with a neurodegenerative disorder comprising administering to the individual: a plurality of induced pluripotent stem cell derived neural progenitor cells (iNPCs), wherein the iNPCs express a genomically integrated expression cassette comprising; a constitutive promoter, an inducible, bi-directional polycistronic promoter comprising a tet response element, and a sequence encoding GDNF. In various embodiments, the neurodegenerative disorder is selected from amyotrophic lateral sclerosis (ALS), Parkinson's, Huntington's, and Alzheimer's Diseases. In various embodiments, the neurodegenerative disorder is amyotrophic lateral sclerosis (ALS). In various embodiments, the neurodegenerative disorder is Parkinson's disease. In various embodiments, the neurodegenerative disorder is Alzheimer's disease. In various embodiments, the central nervous system includes a region of the brain. In various embodiments, the region of the brain includes the substantia nigra. In various embodiments, the region of the brain includes the motor cortex. In various embodiments, the region of the brain includes the entorhinal cortex and/or the hippocampus. In various embodiments, the individual is a human. In various embodiments, the genomically integrated expression cassette is integrated at a region of the genome with a reduced probability of oncogenic transformation for a cell comprising the genomically integrated expression cassette. In various embodiments, the genomically integrated expression cassette is integrated at a region of the genome selected from the adeno-associated virus site 1 (AAVS1), the chemokine (C-C motif) receptor 5 (CCR5) gene, and a human ortholog of the mouse Rosa26 locus. In various embodiments, the genomically integrated expression cassette is integrated at the adeno-associated virus site 1 (AAVS1). In various embodiments, the genomically integrated expression cassette is integrated at the chemokine (C-C motif) receptor 5 (CCR5) gene. In various embodiments, the genomically integrated expression cassette is integrated by homologous recombination. In various embodiments, the genomically integrated expression cassette lacks sequences derived from a transposable element. In various embodiments, the genomically integrated expression cassette is integrated by a transposon. In various embodiments, the method further includes administering to the individual a tetracycline-class antibiotic, wherein the tetracycline-class antibiotic induces transcription of a GDNF mRNA in the plurality of induced pluripotent stem cell derived neural progenitor cells. In various embodiments, the genomically integrated expression cassette is integrated as a single-copy.

Also described herein is use of a plurality of induced pluripotent stem cell derived neural progenitor cells (iNPCs) in a method of increasing glial derived neurotrophic factor (GDNF) levels in the central nervous system of an individual afflicted with a neurodegenerative disorder, wherein the iNPCs express a genomically integrated expression cassette comprising; a constitutive promoter, an inducible, bi-directional polycistronic promoter comprising a tet response element, and a sequence encoding GDNF. In various embodiments, the neurodegenerative disorder is selected from amyotrophic lateral sclerosis (ALS), Parkinson's, Huntington's, and Alzheimer's Diseases. In various embodiments, the neurodegenerative disorder is amyotrophic lateral sclerosis (ALS). In various embodiments, the neurodegenerative disorder is Parkinson's disease. In various embodiments, the neurodegenerative disorder is Alzheimer's disease. In various embodiments, the central nervous system includes a region of the brain. In various embodiments, the region of the brain includes the substantia nigra. In various embodiments, the region of the brain includes the motor cortex. In various embodiments, the region of the brain includes the entorhinal cortex and/or the hippocampus. In various embodiments, the individual is a human. In various embodiments, the genomically integrated expression cassette is integrated at a region of the genome with a reduced probability of oncogenic transformation for a cell comprising the genomically integrated expression cassette. In various embodiments, the genomically integrated expression cassette is integrated at a region of the genome selected from the adeno-associated virus site 1 (AAVS1), the chemokine (C-C motif) receptor 5 (CCR5) gene, and a human ortholog of the mouse Rosa26 locus. In various embodiments, the genomically integrated expression cassette is integrated at the adeno-associated virus site 1 (AAVS1). In various embodiments, the genomically integrated expression cassette is integrated at the chemokine (C-C motif) receptor 5 (CCR5) gene. In various embodiments, the genomically integrated expression cassette is integrated by homologous recombination. In various embodiments, the genomically integrated expression cassette lacks sequences derived from a transposable element. In various embodiments, the genomically integrated expression cassette is integrated by a transposon. In various embodiments, the genomically integrated expression cassette is integrated as a single-copy.

(A) pB-RTP-Tet-GDNF/memClover-FLuc plasmid that is designed to stably integrate into genome when transfected in combination with pBase plasmid.

(B) pBase plasmid (C) Transgenes that are constitutively expressed or expressed only in the presence of doxycycline.

(D) Live unstained fluorescent imaging of human iNPCs nucleofected with pB-RTP-Tet-GDNF/memClover-FLuc and grown as neurospheres.

(E) Firefly luciferase activity normalized to *Renilla* luciferase in iNPCs. N=4 biological replicates per condition.

(F) Real-time firefly luciferase activity in live culture of iNPCs. N=3 biological replicates per condition. Error bars represent mean±SEM.

Figure 2:
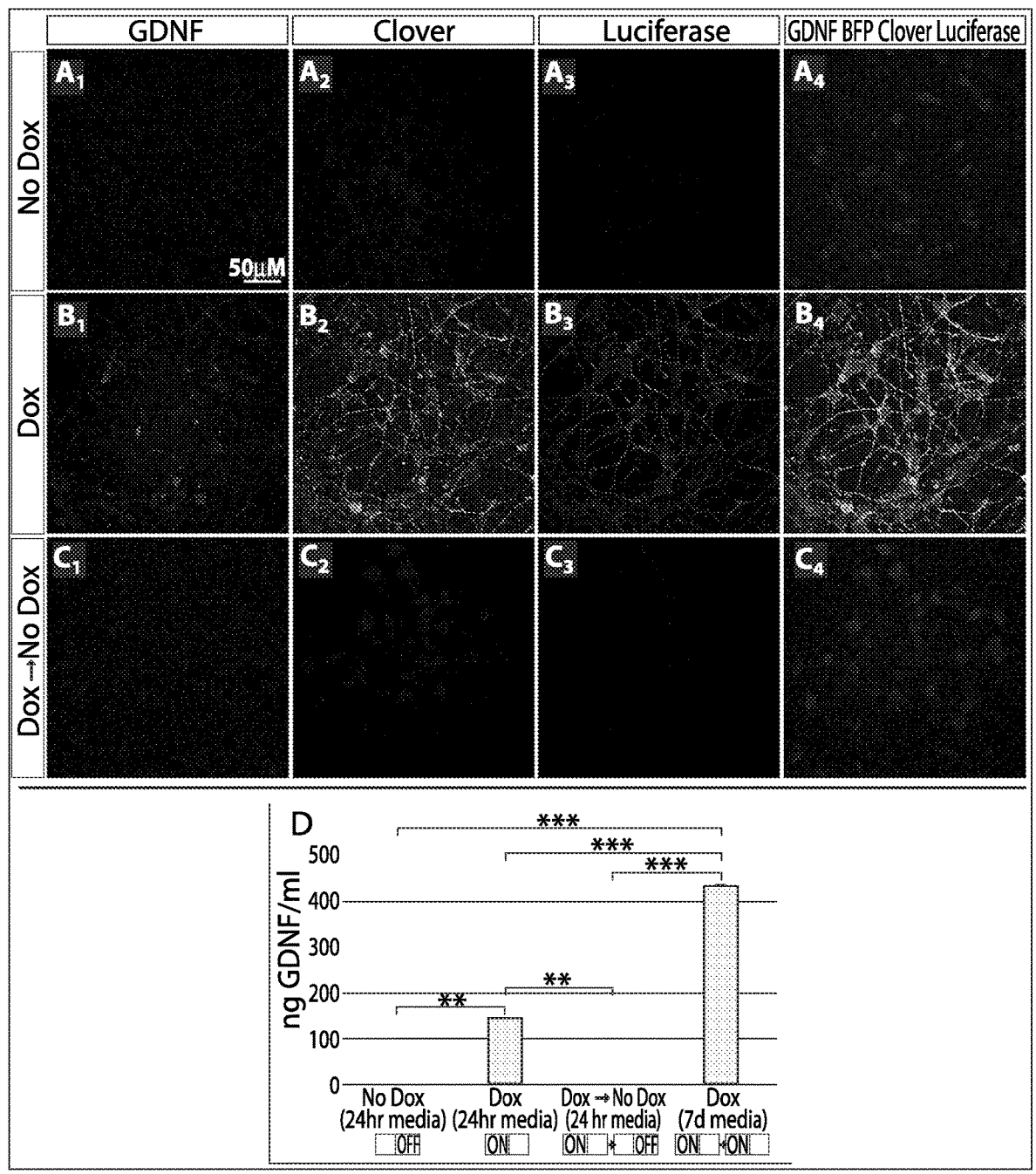

FIG. 2. Doxycycline regulates GDNF expression from pB-RTP-Tet-GDNF/memClover-FLuc nucleofected iPSC-derived NPCs.

Nucleofected iNPCs grown in the (A) absence or (B) presence of dox (C) Nucleofected iNPCs grown in the absence of dox after dox was added and removed (D) ELISA of 24-hour incubated media from cells in (A-C), as well as in a culture with GDNF protein accumulation for 7 days. N=3 biological replicates per condition. Error bars represent mean±SEM. p<0.01, *p<0.001

Figure 3:
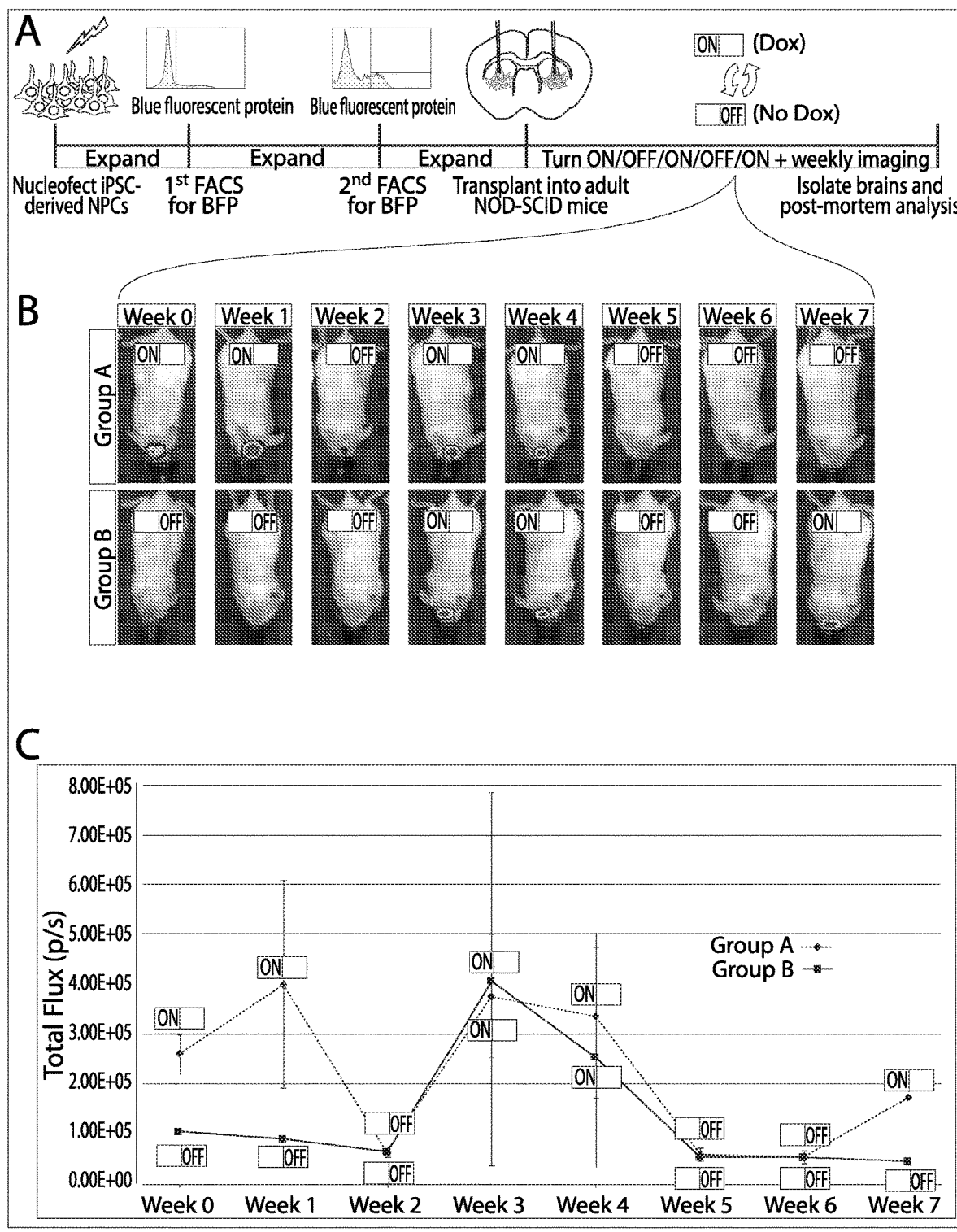

FIG. 3. Reporter transgene expression is inducible and reversible in iPSC-derived NPC transplants.

(A) Experimental design for nucleofection, expansion, FACS, transplant, treatment, and postmortem analysis.

(B) Weekly bioluminescence imaging of one animal from each group (Animal #9 for Group A and Animal #3 for Group B) over 7-week in vivo experimental period. ON/OFF buttons indicate if animal received dox during the week prior to imaging.

(C) Summary of weekly bioluminescence activity for all animals (N=14). One animal (#13) was excluded from this analysis due abnormally high bioluminescence signal observed and no inducible transgene signal observed by postmortem immunohistochemistry. Error bars represent mean±SEM.

Figure 4:
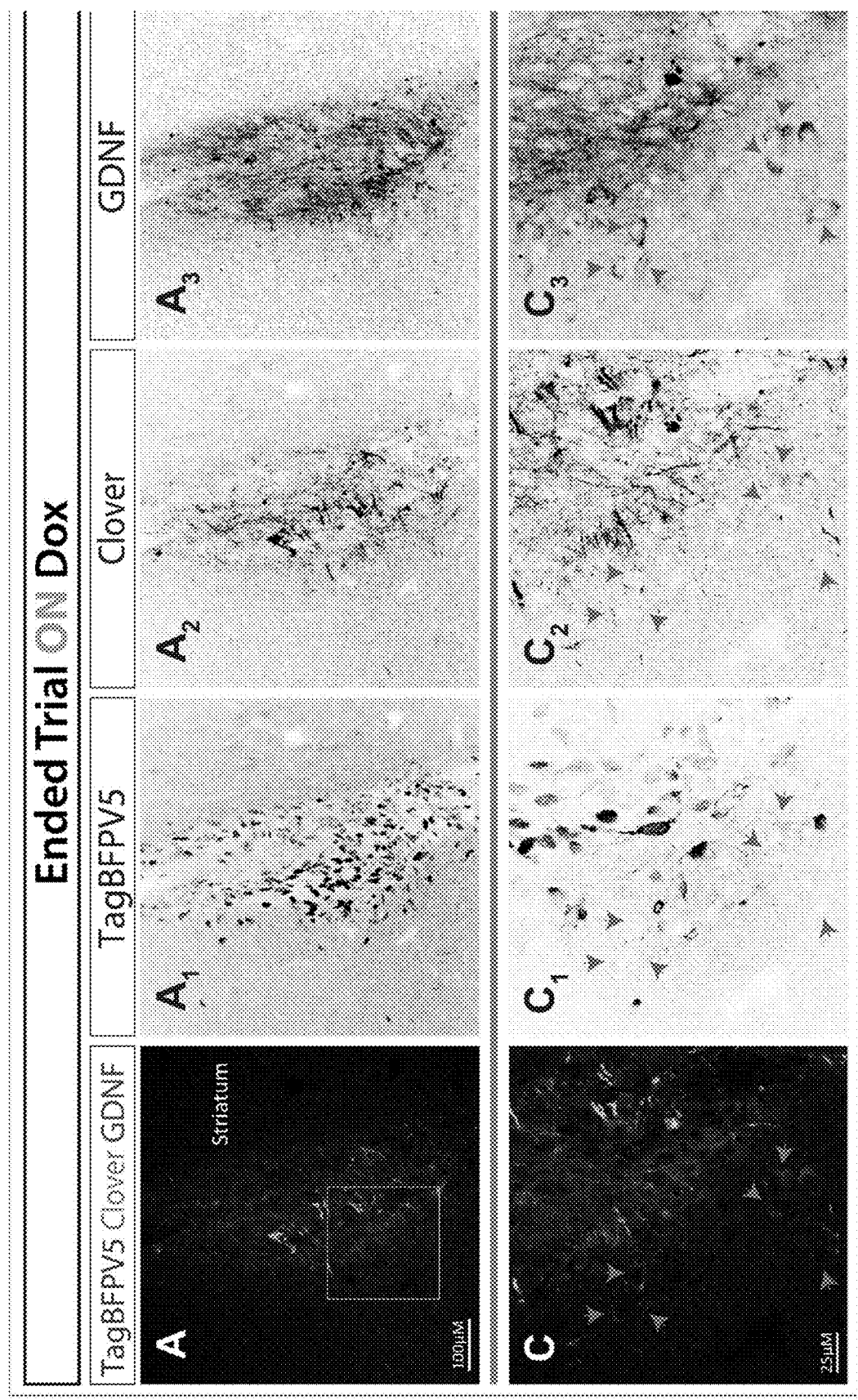
Figure 4:
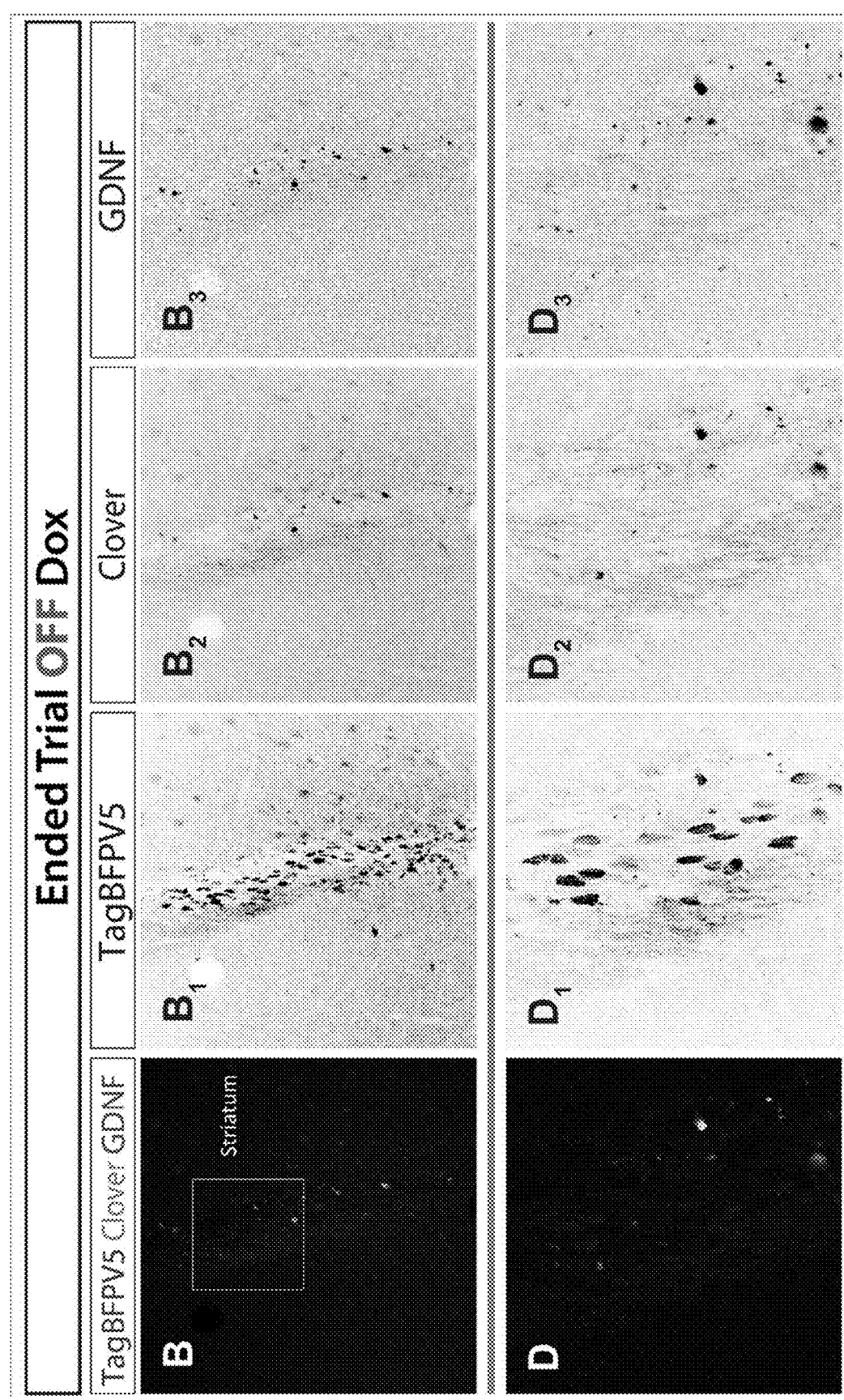

FIG. 4. Doxycycline administration mediates GDNF expression in transplanted iPSC-derived NPCs.

Striatal region of (A) animal #1 at experimental endpoint [Started OFF→ON→OFF→Ended ON] and (B) Animal #7 at experimental endpoint [Started ON→OFF→ON→Ended OFF].

(C) High magnification image of squared region in (A). Pink arrows indicate GDNF expression in areas distant from TagBFP+ cells, suggesting that host cells uptae secreted GDNF.

(D) High magnification image of squared region in (B). Note: Clover signal and GDNF signal are likely background given the overlap (B2/B3 and D2/D3).

Figure 5:
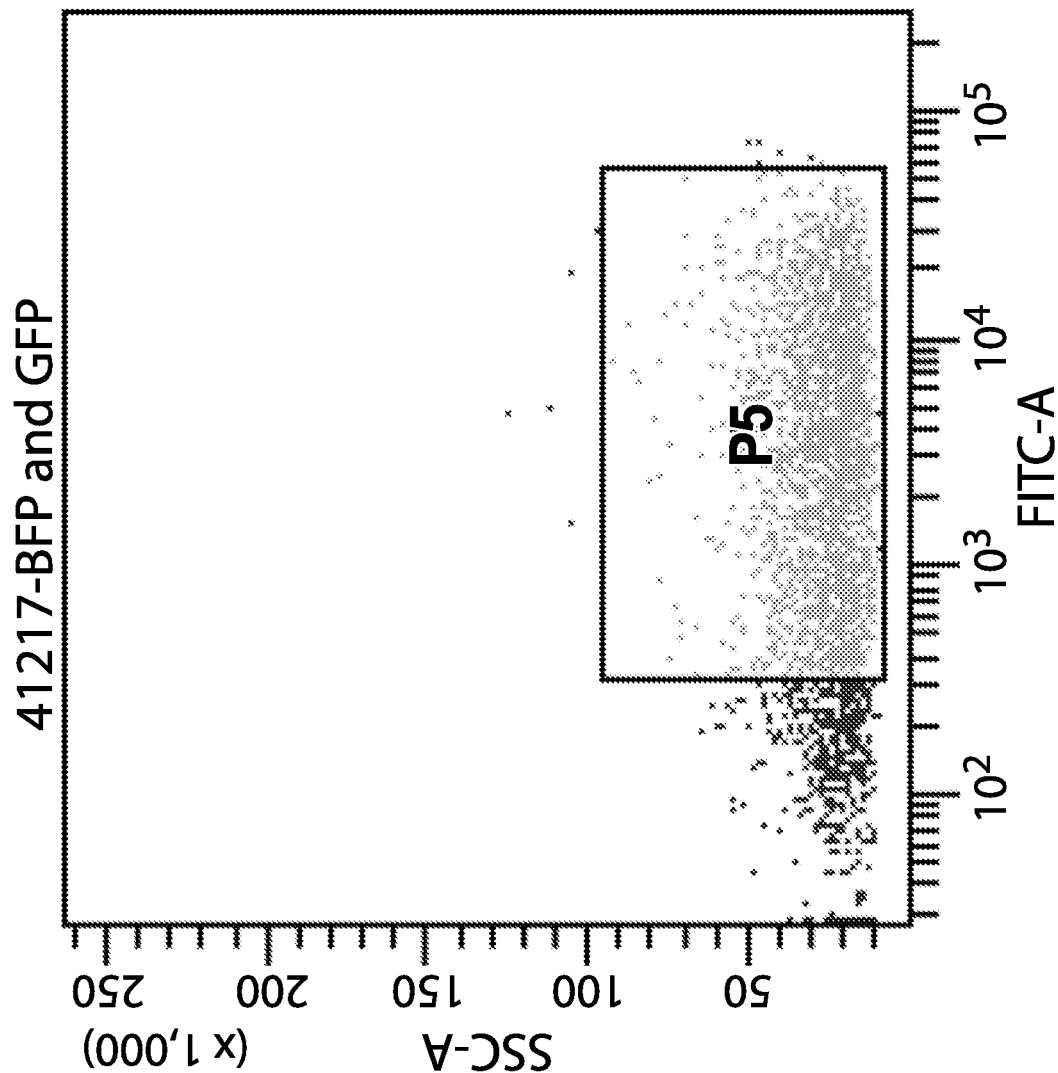

FIG. 5. IPSC-derived NPCs nucleofected with pB-RTP-Tet-GDNF/memClover-FLuc retain their ability to be induced upon the addition of dox. 83% of BF+ cells were also GFP+ (P5 Gate) 24 hours after adding dox to cells that were grown in culture for 6 months after nucleofection. Note: Cells were also exposed to two freeze/thaw cycles and were frozen for a total of 10 months during this period.

Figure 6:
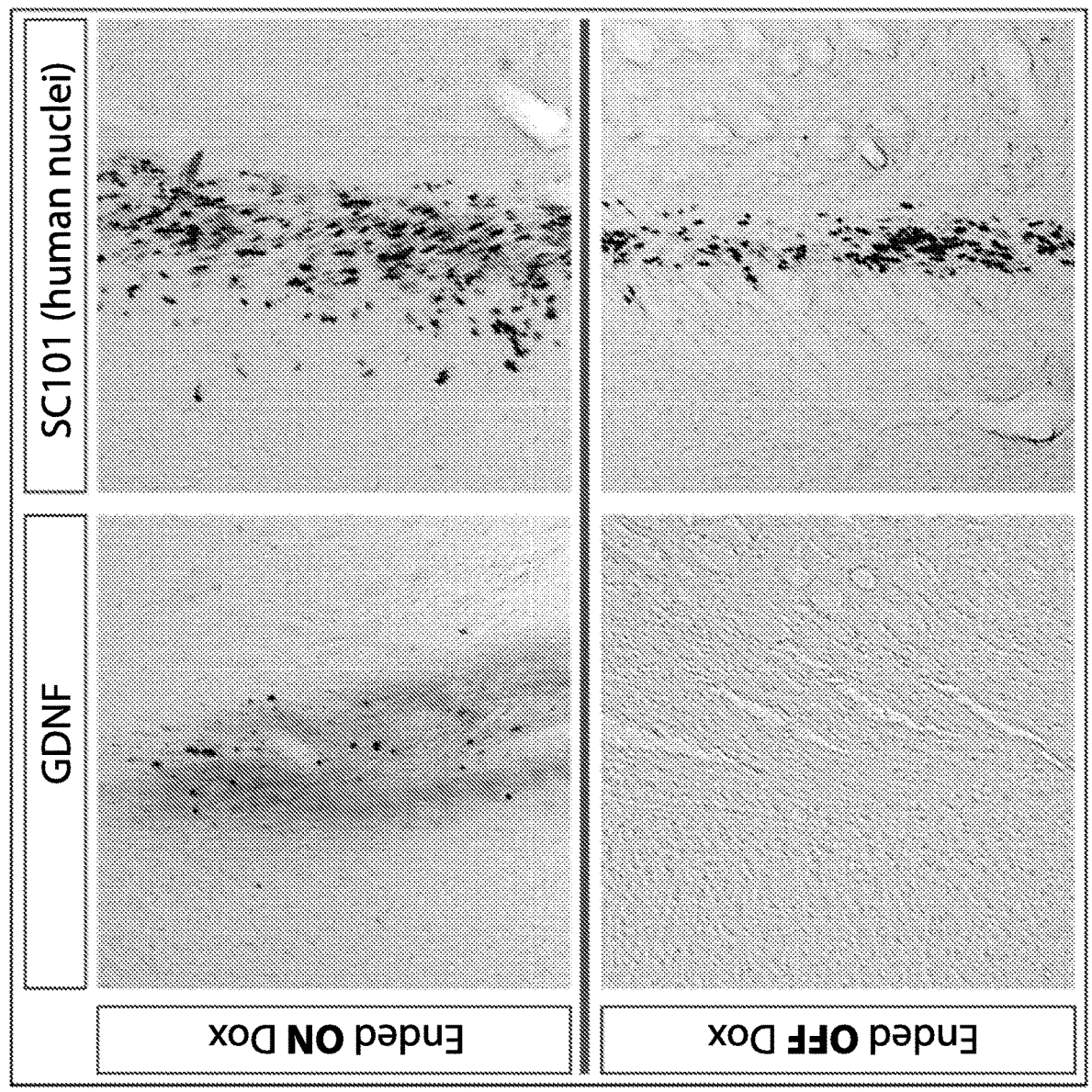

FIG. 6. GDNF DAB staining of animals reveals increased signal in animal that ended trial on dox. Related to FIG. 4.

Figure 7:
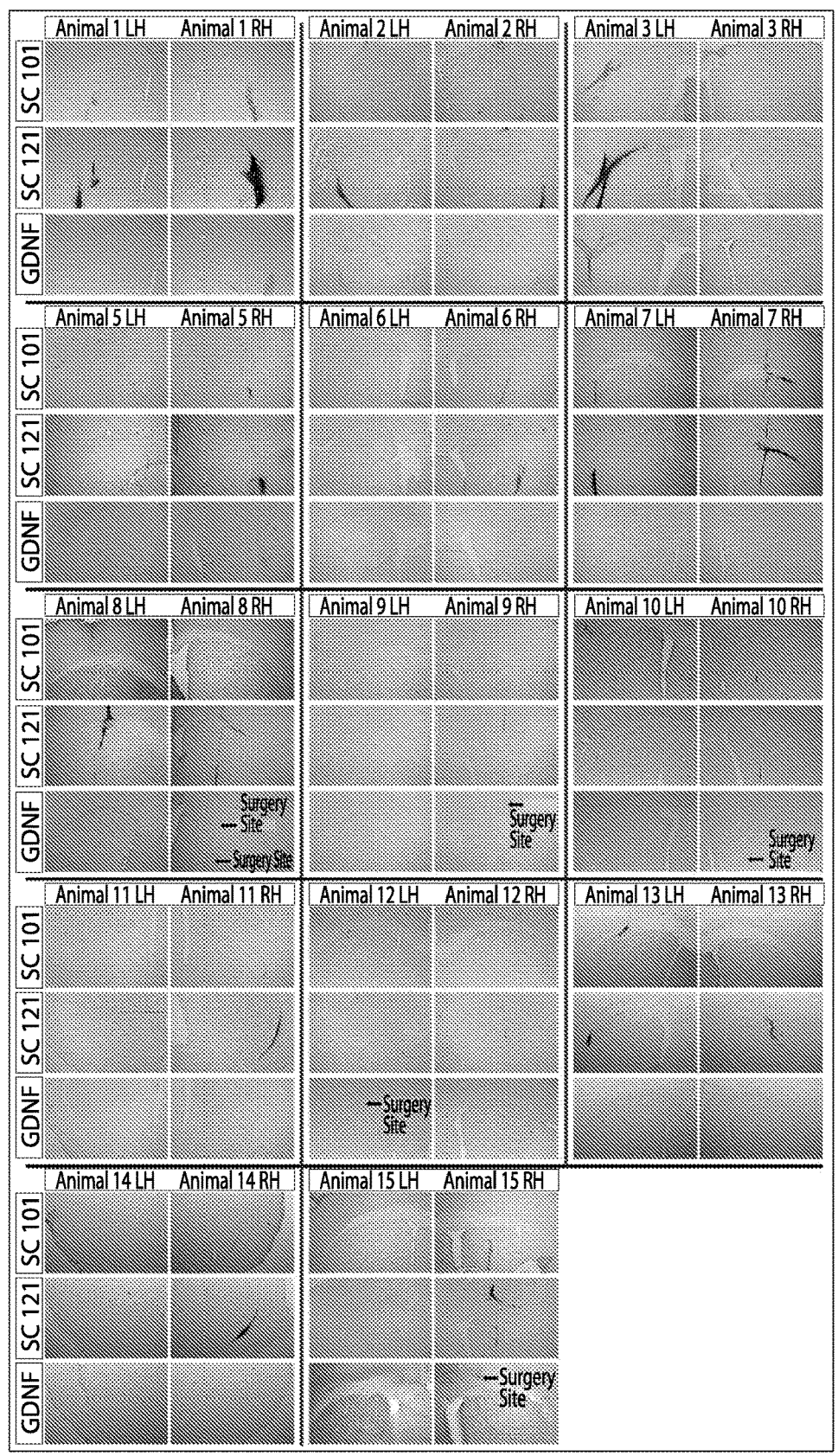

FIG. 7. GDNF, SC121 (human cytoplasm), and SC101 (human nuclei) staining of striatal/corpus callosum region of all animals used in study reveals increased GDNF signal in animals that ended trial on dox. These data were used for the blinded grading of GDNF signal shown in Table 2. (RH=right hemisphere; LH=left hemisphere).

Figure 8:
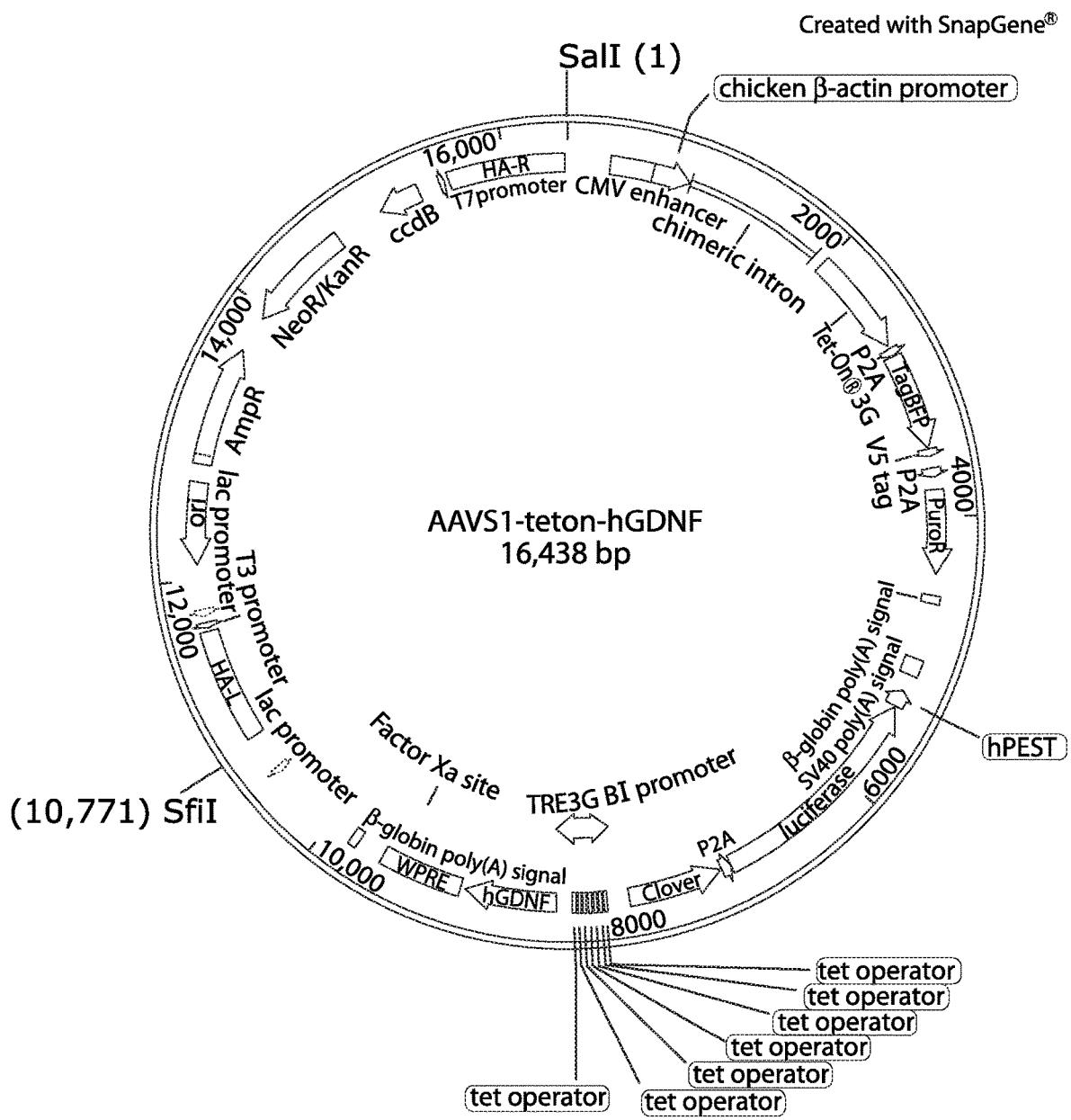

FIG. 8. Vector map of AAVS1-teton-hGDNF. Shown are HA-L and HA-R arms, which are homologous recombination sequences that can be used to target genomic safe harbors, such as AAVS.

Figure 9:
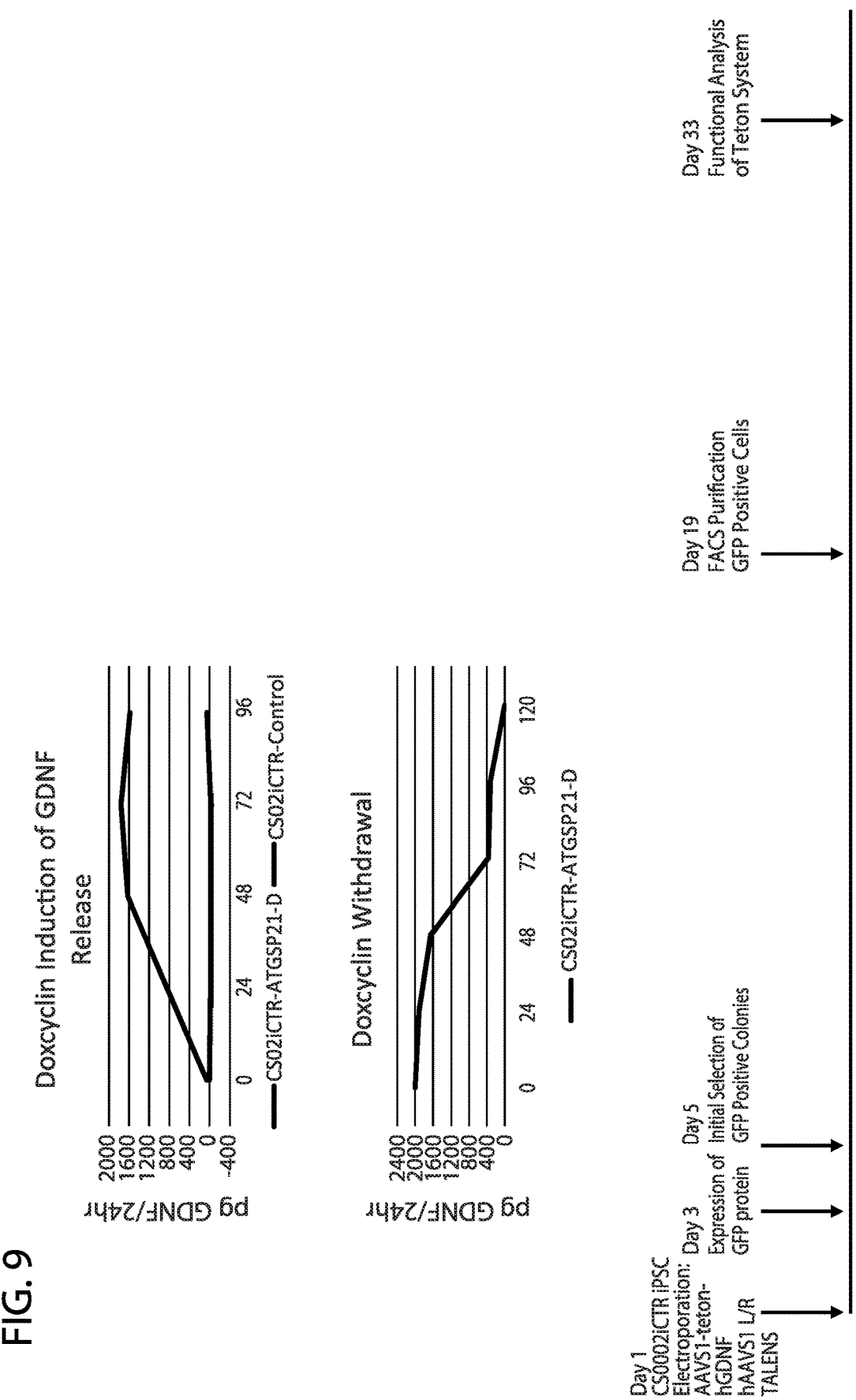

FIG. 9. Scheme of evaluation of inducible GDNF expression.

Figure 10:
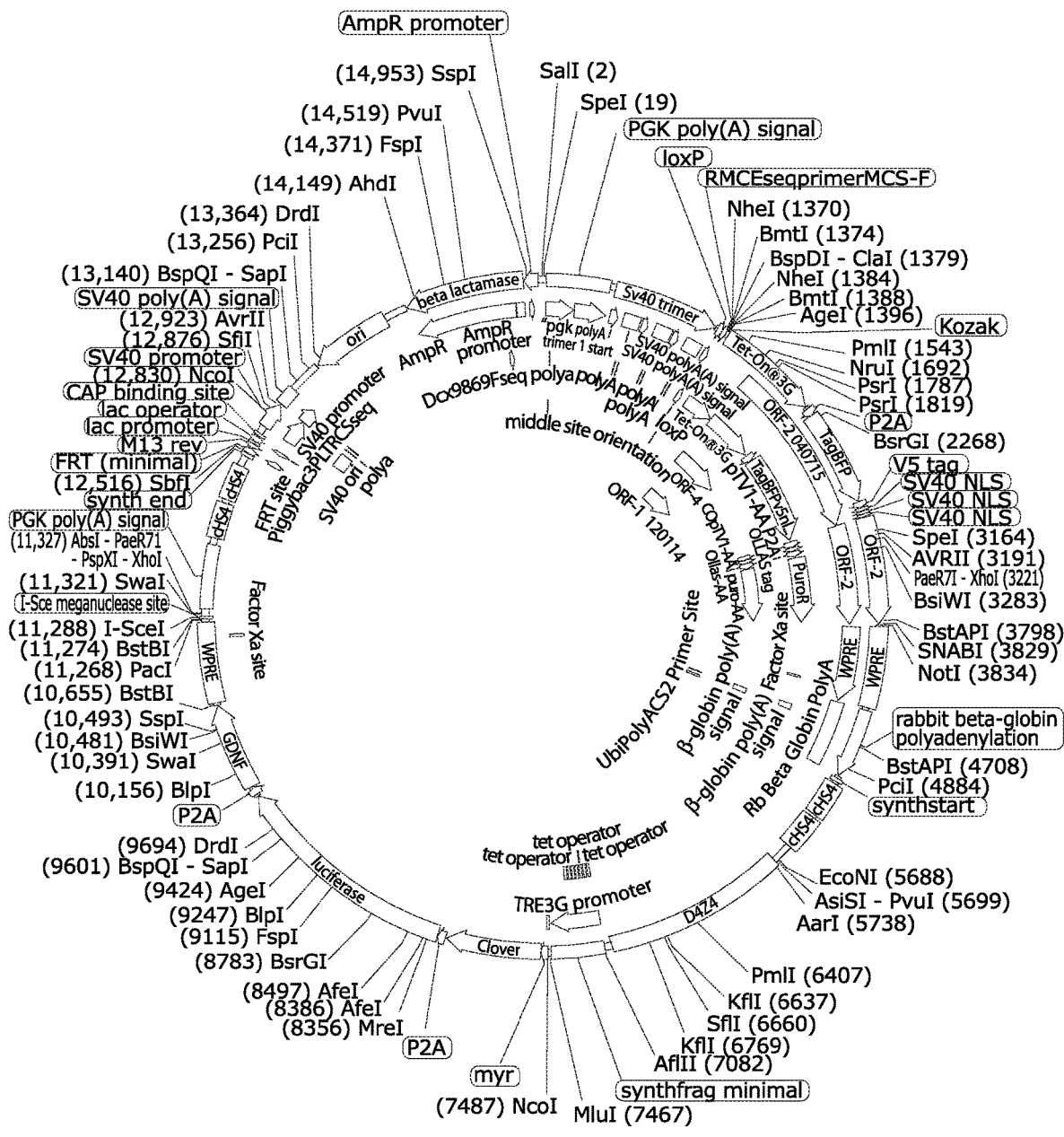

FIG. 10. Vector map of pDonor-Teton3g-2a-TagBFP-V5-nls-p2a-puroR WPRE_Insulated mpclover-2a-luc2pest-2a-gdnf wpre.

Figure 11:
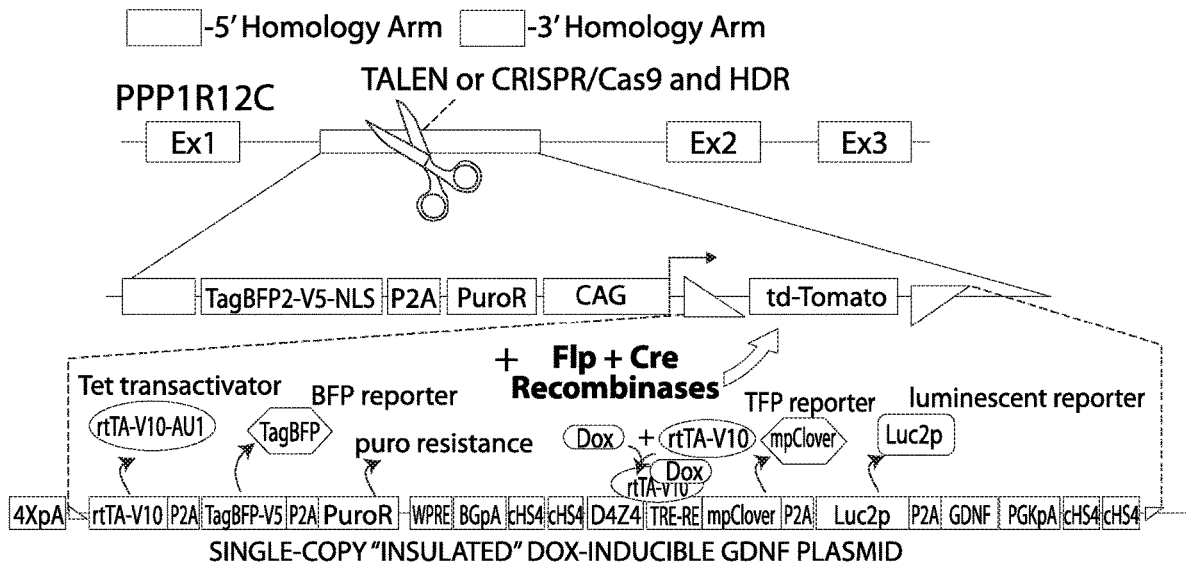
Figure 11:
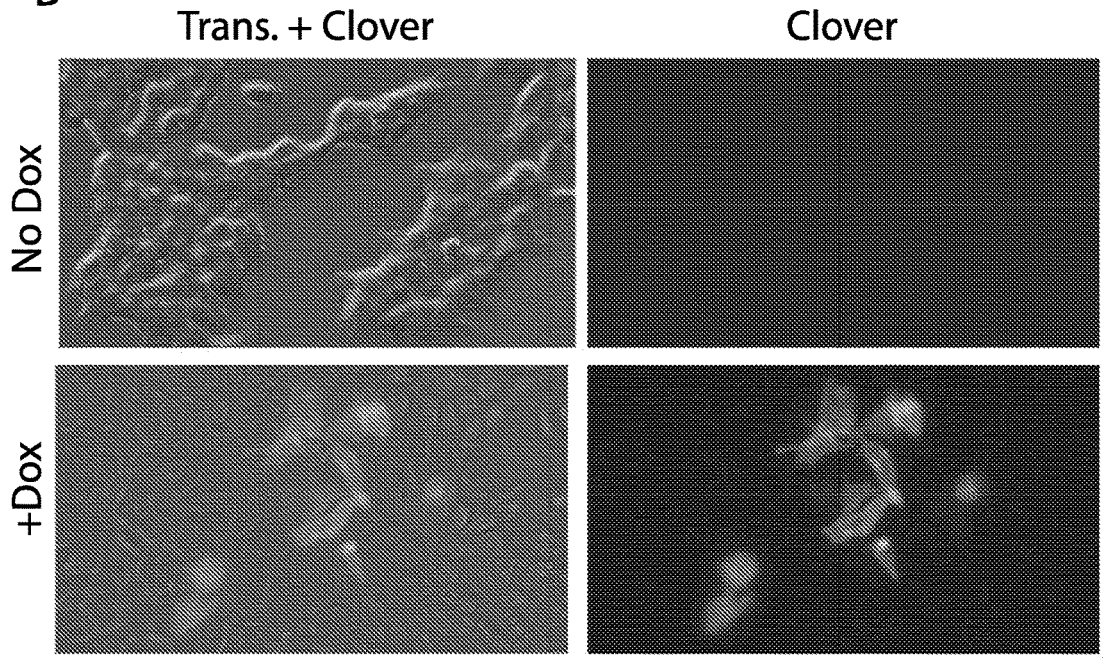

FIG. 11. (A) Schematic of AAVS1 targeting of the endogenous locus between exon 1 and 2 of the human PPP1R12C gene. Initially, a recipient "landing site" consisting of a reporter/selection cassette (TagBFP2 and PuroR for fluorescent and antibiotic selection) driven by a splice acceptor linked to the upstream PPP1R12C and a constitutive CAG promoter driven td-Tomato red fluorescent cistron flanked by a LoxP and an FRT site were stable integrated. Subsequently, upon stable selection for these reporters, these cells were lipofected with a plasmid expressing FlpO and Cre and the donor plasmid containing a LoxP and FRT flanked selection/reporter cassette and a dox-inducible mpClover/Luc2p/GDNF cistron-containing plasmid. (B) Transmitted light and green fluorescence imaging of cells in the absence and presence of doxycycline demonstrates the inducibility of mpClover 24 hours after addition of dox and the absence of GFP "leakiness" in the absence of dox. Moreover, these cells were examined roughly 1 week after a sorting to enrich transfected cells and 2 weeks after transfection so the mpClover populations are stable transfections.

DETAILED DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3rd ed., Revised, J. Wiley & Sons (New York, NY 2006); and Sambrook and Russel, *Molecular Cloning: A Laboratory Manual* 4th ed., Cold Spring Harbor Laboratory Press (Cold Spring Harbor, NY 2012), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

The term "control elements" refers collectively to promoter regions, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control elements need always be present, so long as the selected coding sequence is capable of being replicated, transcribed and translated in an appropriate host cell.

The term "promoter region" is used herein in its ordinary sense to refer to a nucleotide region including a DNA regulatory sequence, wherein the regulatory sequence is derived from a gene which is capable of binding RNA polymerase and initiating transcription of a downstream (3'-direction) coding sequence.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

Delivering trophic factors to the brain using stem cell-derived neural progenitors is a powerful way to bypass the blood brain barrier. The delivery of various growth factors to the site of damage using ex vivo genetically modified cells has been shown to support host neurons in disease models of amyotrophic lateral sclerosis (ALS) and Parkinson's, Huntington's, and Alzheimer's Diseases. In parallel, delivery of glial cell line-derived neurotrophic factor (GDNF) has provided benefits to Parkinsonian patients and is currently being tested in a Phase 1/2a clinical trial for ALS patients. To fully exploit the benefits of trophic factors and ward off potential unwanted effects of trophic factors delivered by cells, regulation of growth factor secretion is a promising avenue for several neurodegenerative diseases. Chronic trophic factor delivery prohibits dose adjustment or shut off in the event of side effects as gene expression and downstream signaling activation are tightly connected processes. Lack of control over the timing and magnitude of gene expression could limit the efficacy of therapy and introduce unintended cellular effects.

Toward these ends, tetracycline (Tet)-regulated systems have been used to temporally and spatially regulate gene expression in various methodologies. This includes bacterial Tet transactivator (tTA) to silence gene expression downstream of a Tet-regulated promoter in the presence of doxycycline (dox), a Tet analog. In addition to this "Tet-Off" system, a "Tet-On" system uses a reverse tTA (rtTA) in order to activate transgene expression in the presence of dox The use of tTA and rtTA variants in neural stem cell populations is unexplored.

Described herein is a stably integrating, third-generation doxycycline-regulated vector, allowing inducible and reversible expression of a therapeutic molecule. Human iPSC-derived neural progenitors were stably transfected with the vector, expanded and transplanted into the adult mouse brain. We observed that the addition and withdrawal of doxycycline led to GDNF expression that could be induced and reversed multiple times, demonstrating that doxycycline can penetrate the graft and regulate transgene expression in vivo. Our findings provide a proof of concept for combining gene and stem cell therapy for effective modulation of ectopic protein expression in transplanted cells.

Described herein is a method of treatment, including administering a quantity of cells to a subject afflicted with a disease or condition, wherein the cells express a therapeutic protein or peptide, and further wherein the cells, therapeutic protein or peptide, or both, are capable of treating the disease or condition. In other embodiments, the cells are neural lineage cells. In other embodiments, the neural lineage cells are neural progenitor cells. In other embodiments, the neural progenitor cells are derived from induced pluripotent stem cells (iPSCs). In various embodiments, neural progenitor cells are generated from iPSC colonies by culturing in a neural stem cell medium containing high concentrations of EGF and FGF-2. Cell aggregates (termed EZ spheres) could be expanded for long periods using a chopping method that maintained cell-cell contact. In various embodiments, EZ spheres are withdrawn from EGF/FGF, cultured with retinoic acid RA in a neural induction. Techniques related to neural progenitor cells derived from iPSCs are described in Sareen et al. "Human neural progenitor cells generated from induced pluripotent stem cells can survive, migrate, and integrate in the rodent spinal cord" *J Comp Neurol.* 2014 Aug. 15; 522(12): 2707-2728 and Ebert et al., "EZ spheres: a stable and expandable culture system for the generation of pre-rosette multipotent stem cells from human ESCs and iPSCs" *Stem Cell Res.* 2013 May; 10(3):417-427, which are fully incorporated by reference herein. In other embodiments, the iPSCs include somatic cells such as fibroblasts and blood reprogrammed according to methods described in U.S. Pub. No. 2017/0362574, which is fully incorporated by reference herein.

In other embodiments, the cells express an expression cassette from one or more vectors. In other embodiments, the cells expressing the expression cassette from the one or more vectors have been nucleofected, transfected, or electroporated or other gene delivery techniques known in the art. In other embodiments, the one or more vectors includes a piggyBac vector, a pBase vector, or both. In other embodiments, the piggyBac vector includes at least two promoters, wherein at least one promoter is inducible. In other embodiments, the least one inducible promoter is polycistronic. In other embodiments, the at least one inducible, polycistronic promoter is bi-directional. In other embodiments, the expression cassette is genomically integrated. In other embodiments, the expression cassette encodes the therapeutic protein or peptide. In other embodiments, the therapeutic protein or peptide includes a neurotrophic factor.

In various embodiments, the one or more vectors include a vector with a gene expression cassette flanked by two transposon elements. In various embodiments, the two transposon elements include piggyBac terminal repeats (PB TR). In various embodiments, the vector includes the constitutive promoter includes CMV/Chick β-Actin (aka CAG) promoter. In various embodiments, the vector includes an includible, bi-directional promoter includes TRE-Bi promoter. In various embodiments, the constitutive promoter is operatively linked to a tet response elements. In various embodiments, the "tet-on" element including for example, rTA. In other embodiments, rTA includes rtTA-V10. In various embodiments, the constitutive promoter is operatively linked to a selection factor, including for example neomycin or puromycin. In various embodiments, the inducible, bi-directional promoter is polycistronic. In various embodiments, the inducible bi-directional promoter is operatively linked to elements in a first, second or third or more cistrons. In various embodiments, a first, second, or third, or more cistrons includes a transgene. In various embodiments, the transgene is followed by one or more post-transcriptional elements. In various embodiments, the one or more post-transcriptional element includes woodchuck hepatitis virus post-transcriptional element (WPRE). In various embodiments, the transgene is followed by one or more poly-A tails. In this includes, for example, rabbit beta-globin polyAs. In various embodiments, the transgene is a neurotrophic factor. In various embodiments, the neurotrophic factor includes glial derived neurotrophic factor (GDNF). Additional information is found in PCT Pub. No. WO 2017/131926 and Akhtar et al. "A Transposon-Mediated System for Flexible Control of Transgene Expression in Stem and Progenitor-Derived Lineages" *Stem Cell Reports.* 2015 Mar. 10; 4(3): 323-331, which is fully incorporated by reference herein.

In other embodiments, the one or more vectors include a vector encoding a recombinase including VCre (Vlox and derivatives), SCre (Slox and derivatives), Dre (Rox and derivatives), and phiC31 (attb) or other recombinases known in the art.

In other embodiments, the neurotrophic factor includes glial derived neurotrophic factor (GDNF). In other embodiments, the disease or condition is a neurodegenerative disease. In other embodiments, the neurodegenerative disease is amyotrophic lateral sclerosis (ALS). In other embodiments, administering a quantity of cells includes injection. In other embodiments, the method includes administration of tetracycline, an analog or derivative thereof, including for example, doxycycline.

In various embodiments, the vector includes at least one homologous recombination sequence. In other embodiments, the homologous recombination sequence includes a sequence capable of targeting a genomic safe harbor. In other embodiments, the genomic safe harbor is one of: the adeno-associated virus site 1 (AAVS1), the chemokine (C-C motif) receptor 5 (CCR5) gene, human ortholog of the mouse Rosa26 locus. An exemplary sequence of one of the aforementioned vectors is SEQ ID NO: 2 and SEQ ID NO: 3.

Described herein is a method, including providing a quantity of induced pluripotent stem cell (iPSC) derived cells, and introducing at least two vectors into the iPSC derived cells. In other embodiments, the iPSC derived cells are neural progenitor cells. In other embodiments, introducing at least two vectors includes one or more of: nucleofection, transfection and electroporation. In other embodiments, the at least two vectors includes a piggyBac vector and a pBase vector. In other embodiments, the piggyBac vector includes an expression cassette, including a constitutive promoter, an inducible, bi-directional polycistronic promoter including a tet responsive element, and a sequence encoding a protein or peptide, two transposon elements, wherein the two transposon elements flank the expression cassette. In other embodiments, the protein or peptide includes a neurotrophic factor. In other embodiments, the neurotrophic factor includes glial derived neurotrophic factor (GDNF). In other embodiments, the vector includes at least one homologous recombination sequence. In various embodiments, the vector and/or cells comprising the vector lack a transposable element and/or a transposon derived sequence within 500 bp, 1 kb, 2 kb, 5 kb, or 10 kb of the expression cassette. In various embodiments, the vector and/or cells comprising the vector lack a virally derived sequence within 500 bp, 1 kb, 2 kb, 5 kb, or 10 kb of the expression cassette. In various embodiments, the cells includes 1 or 2 copies of the genomically integrated vector. In various embodiments, the cells includes the vector genomically integrated as a single copy.

Also described herein is a quantity of cells made by the aforementioned method, wherein the iPSC derived cells express a genomically integrated expression cassette. For example, a quantity of neural progenitor cells capable of inducible expression of glial derived neurotrophic factor (GDNF) made by a method including providing a quantity of induced pluripotent stem cell derived neural progenitor cells (iNPCs), and introducing a piggyBac vector and a pBase vector into the iNPCs derived cells, wherein the piggyBac vector includes a constitutive promoter, an inducible, bi-directional polycistronic promoter including a tet response element, and a sequence encoding GDNF. In various embodiments, the vector includes at least one homologous recombination sequence.

Further described herein is a method of treating a degenerative disease and/or condition using the aforementioned cells, including a neurodegenerative disease such as amyotrophic lateral sclerosis (ALS).

Described herein is a method, including administering a quantity of induced pluripotent stem cell derived neural progenitor cells (iNPCs) to a subject afflicted with a neurodegenerative disease, wherein the cells inducibly express a neurotrophic factor capable of treating the disease. In other embodiments, the iNPCs express a genomically integrated expression cassette introduced by nucleofection, the expression cassette including a constitutive promoter, an inducible, bi-directional polycistronic promoter including a tet response element, and a sequence encoding glial derived neurotrophic factor (GDNF). In various embodiments, the vector includes at least one homologous recombination sequence. In other embodiments, the method includes administration of tetracycline, an analog or derivative thereof.

Also described herein is a quantity of neural progenitor cells capable of inducible expression of glial derived neurotrophic factor (GDNF), wherein the neural progenitor cells include a genomically integrated expression cassette, including a bi-directional polycistronic promoter including a tet response element, and a sequence encoding GDNF. Further described herein is a method of treating a degenerative disease and/or condition using the aforementioned cells, including a neurodegenerative disease such as amyotrophic lateral sclerosis (ALS).

Described herein is a vector including a gene expression cassette including a constitutive promoter, an inducible, bi-directional promoter including a tet response element, and a sequence encoding a protein or peptide. In various embodiments, the gene expression cassette is flanked by two transposon elements. In various embodiments, the two transposon elements include piggyBac terminal repeats (PB TR). In various embodiments the two transposon elements include loxP and flippase recognition target, or other transposon elements known in the art. In various embodiments, the constitutive promoter includes CMV/Chick β-Actin (aka CAG) promoter. In various embodiments, the includible, bi-directional promoter includes TRE-Bi promoter. In various embodiments, the constitute promoter is operatively linked to a tet response elements. In various embodiments, the tet response element is a "tet-off" element, including for example, tTA, or a "tet-on" element including for example, rTA. In other embodiments, rTA includes rtTA-V10. In various embodiments, the constitutive promoter is operatively linked to a selection factor, including for example neomycin or puromycin. In various embodiments, embodiments, the inducible, bi-directional promoter is polycistronic. In various embodiments, the inducible bi-directional promoter is operatively linked to elements in a first, second or third or more cistrons. In various embodiments, a first, second, or third, or more cistrons includes a transgene. In various embodiments, the transgene is followed by one or more post-transcriptional elements. In various embodiments, the one or more post-transcriptional element includes woodchuck hepatitis virus post-transcriptional element (WPRE). In various embodiments, the transgene is followed by one or more poly-A tails. In this includes, for example, rabbit beta-globin polyAs. In various embodiments, the transgene is a neurotrophic factor. In various embodiments, the neurotrophic factor includes glial derived neurotrophic factor (GDNF). In various embodiments, the vector includes one or more elements promoting target of safe landing sites, including AAVS1. In various elements, one or more insulator elements around the inducible cassette attenuates potential silencing during cell differentiation. In various embodiments, the expression cassette includes one or more sub-cassettes, wherein each sub-cassette includes 1) a promoter 2) a transgene and 3) a polyA transcription stop element. In various embodiments, the expression cassette including one or more sub-cassettes includes a constitutive sub-cassette and an inducible sub-cassette. For example, the constitutive sub-cassette includes the constitutive promoter expressing rTA transactivator, and the inducible sub-cassette includes an inducible promoter expressing a neurotrophic factor such as GDNF and optionally one or more reporter proteins.

Figure 1:
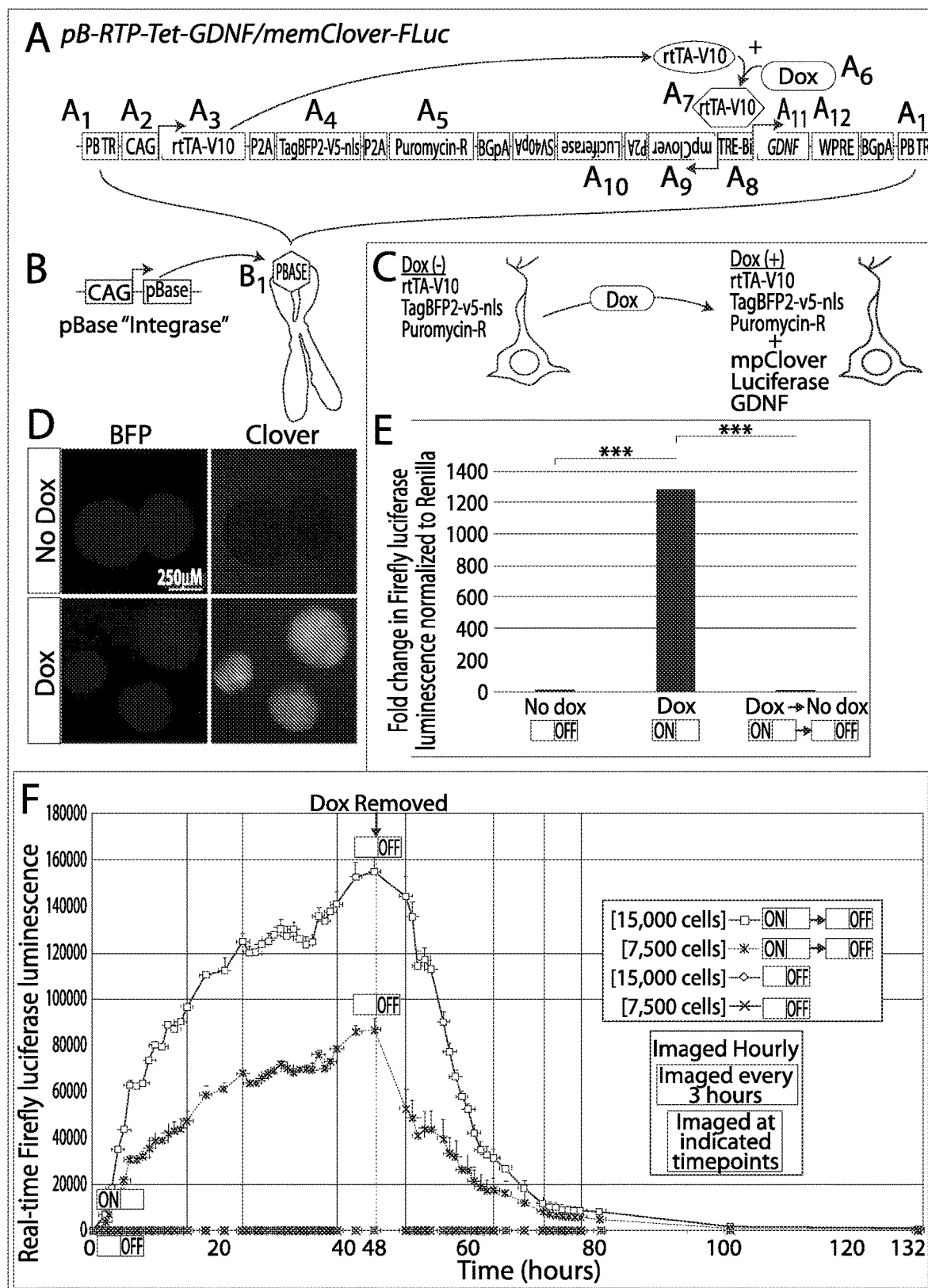
FIG. 1. Description of pB-RTP-Tet-GDNF/memClover-FLuc vector.

An example of the aforementioned vector includes pB-RTP-Tet-GDNF/memClover-FLuc" [piggyBac-Reverse transactivator/TagBFP2nls/PacR-Tet inducible-GDNF/membrane Clover-Firefly Luciferase] [SEQ ID NO: 1], which is depicted in FIG. 1A. Here, the vector includes two promoters—a constitutively active CMV/Chick β-Actin (aka CAG) promoter and an inducible, bi-directional TRE-Bi promoter. The CAG promoter drives constitutive expression of the rtTA-V10 (aka tet-ON) transactivator, TagBFP2-V5nls (enhanced blue fluorescent protein with a V5 tag and nuclear localization sequence), and the puromycin resistance gene. Transgenes in tandem are separated by self-cleaving peptide linkers (P2A). Here, addition of a tetracycline analog or derivative, doxycycline, causes the rtTA-V10 transactivator to bind to the TRE-Bi promoter and catalyze transcription of downstream transgenes. The first cistron of the TRE-Bi promoter harbors a myristoylated and palmitoylated (MyrPalm) clover reporter (mpClover) followed by destabilized firefly luciferase (Luc2P). The second cistron downstream of the inducible TRE-Bi promoter can encode a neurotrophic factor such as GDNF followed by the woodchuck hepatitis virus post-transcriptional element (WPRE) for increased gene expression. Rabbit beta-globin polyAs were placed downstream of the respective elements to terminate transcription and prevent spurious transgene expression. The pB-RTP-Tet-GDNF/memClover-FLuc vector can be transfected alongside a pBase plasmid to promote stable genomic integration. Another example of the aforementioned vector includes pDonor-Teton3g-2a-TagBFP-V5-nls-p2a-puroR WPRE_Insulated mpclover-2a-luc2pest-2a-gdnf were shown in FIG. 10.

In various embodiments, the vector includes at least one homologous recombination sequence. In other embodiments, the homologous recombination sequence includes a sequence capable of targeting a genomic safe harbor. In other embodiments, the genomic safe harbor is one of: the adeno-associated virus site 1 (AAVS1), the chemokine (C-C motif) receptor 5 (CCR5) gene, human ortholog of the mouse Rosa26 locus. An exemplary sequence of one of the aforementioned vectors is SEQ ID NO: 2 and SEQ ID NO: 3.

Described herein is a method of treatment, comprising: administering a quantity of cells to a subject afflicted with a disease or condition, wherein the cells express a therapeutic protein or peptide, and further wherein the cells, therapeutic protein or peptide, or both, are capable of treating the disease or condition. In each and all of the aforementioned embodiments of the method, the cells are neural lineage cells. In each and all of the aforementioned embodiments of the method, the neural lineage cells are neural progenitor cells. In each and all of the aforementioned embodiments of the method, the neural progenitor cells are derived from induced pluripotent stem cells (iPSCs). In each and all of the aforementioned embodiments of the method, the cells express an expression cassette from one or more vectors. In each and all of the aforementioned embodiments of the method, the cells expressing the expression cassette from the one or more vectors have been nucleofected, transfected, or electroporated. In each and all of the aforementioned embodiments of the method, the one or more vectors includes a piggyBac vector, a pBase vector, or both. In each and all of the aforementioned embodiments of the method, the piggyBac vector includes at least two promoters, wherein at least one promoter is inducible. In each and all of the aforementioned embodiments of the method, the at least one inducible promoter is polycistronic. In each and all of the aforementioned embodiments of the method, the at least one inducible, polycistronic promoter is bi-directional. In each and all of the aforementioned embodiments of the method, the expression cassette is genomically integrated. In each and all of the aforementioned embodiments of the method, the expression cassette encodes the therapeutic protein or peptide. In each and all of the aforementioned embodiments of the method, the therapeutic protein or peptide includes a neurotrophic factor. In each and all of the aforementioned embodiments of the method, the neurotrophic factor includes glial derived neurotrophic factor (GDNF). In each and all of the aforementioned embodiments of the method, the disease or condition is a neurodegenerative disease. In each and all of the aforementioned embodiments of the method, the neurodegenerative disease is amyotrophic lateral sclerosis (ALS). In each and all of the aforementioned embodiments of the method, administering a quantity of cells includes injection. In each and all of the aforementioned embodiments of the method, the method includes administration of tetracycline, an analog or derivative thereof.

Described herein is a method comprising: providing a quantity of induced pluripotent stem cell (iPSC) derived cells; and introducing at least two vectors into the iPSC derived cells. In each and all of the aforementioned embodiments of the method, the iPSC derived cells are neural progenitor cells. In each and all of the aforementioned embodiments of the method, introducing at least two vector includes one or more of: nucleofection, transfection and electroporation. In each and all of the aforementioned embodiments of the method, the at least two vectors includes a piggyBac vector and a pBase vector. In each and all of the aforementioned embodiments of the method, the piggyBac vector includes: an expression cassette, comprising: a constitutive promoter, an inducible, bi-directional polycistronic promoter comprising a tet responsive element, and a sequence encoding a protein or peptide, two transposon elements, wherein the two transposon elements flank the expression cassette. In each and all of the aforementioned embodiments of the method, protein or peptide includes a neurotrophic factor. In each and all of the aforementioned embodiments of the method, the neurotrophic factor includes glial derived neurotrophic factor (GDNF). In each and all of the aforementioned embodiments of the method, the piggyBac vector includes a homologous recombination sequence. In each and all of the aforementioned embodiments of the method, the homologous recombination sequence includes a sequence capable of targeting a genomic safe harbor. In each and all of the aforementioned embodiments of the method, the genomic safe harbor is one of: the adeno-associated virus site 1 (AAVS1), the chemokine (C-C motif) receptor 5 (CCR5) gene, human ortholog of the mouse Rosa26 locus.

This further includes quantity of cells made by each and all of the aforementioned embodiments of the method, wherein the iPSC derived cells express a genomically integrated expression cassette.

Also described herein is a method, comprising administering a quantity of induced pluripotent stem cell derived neural progenitor cells (iNPCs) to a subject afflicted with a neurodegenerative disease, wherein the cells inducibly express a neurotrophic factor capable of treating the disease. In each and all of the aforementioned embodiments of the method, iNPCs express a genomically integrated expression cassette introduced by nucleofection, the expression cassette comprising: a constitutive promoter, an inducible, bi-directional polycistronic promoter comprising a tet response element, and a sequence encoding glial derived neurotrophic factor (GDNF). In each and all of the aforementioned embodiments of the method, the method includes administration of tetracycline, an analog or derivative thereof.

EXAMPLES

Described herein are non-limiting examples of the claimed invention.

Example 1

Dox Addition to Cell Culture or to Animals, iPSCs and iNPCs

In all experiments, dox solution was maintained in light protection and 4° C. For cell culture, dox (Clontech 631311) was added to culture media at 100 ng/ml. For in vivo work, animals were administered dox (15 µg dox/g weight) every 3-4 days by oral gavage (e.g. 60 µl for a 20 g animal), using a soft-tipped feeding needle (Instech FTP-20-30; Plymouth Meeting, PA) attached to a 1 ml syringe (BD 309659; Franklin Lakes, NJ).

Reprogramming of somatic cells to generate iPSCs and subsequent generation of iNPCs has been described previously, including for example, Sareen et al. "Human neural progenitor cells generated from induced pluripotent stem cells can survive, migrate, and integrate in the rodent spinal cord" *J Comp Neurol*. 2014 Aug. 15; 522(12): 2707-2728, which is fully incorporated by reference herein.

Briefly, for reprogramming and iPSC generation, cells such as fibroblasts are reprogrammed into virus-free iPSC lines using the Amaxa Human Dermal Fibroblast Nucleofector Kit to express episomal plasmids with 6 factors: OCT4, SOX2, KLF4, L-MYC, LIN28, and p53 shRNA (Addgene). Exogenously introduced genes do not integrate and are instead expressed episomally in a transient fashion. Briefly, fibroblasts (0.8×106 cells per nucleofection) were harvested, centrifuged at 200 g for 5 minutes, re-suspended carefully in Nucleofector® Solution (VPD-1001, Lonza) and the U-023 program was applied. All cultures were maintained under norm-oxygen conditions (5% O2) during reprogramming, which further enhance the efficiency of iPSC generation. The media was kept on for 48 hours and gradually changed to chemically-defined mTeSR®1 medium containing small molecules to enhance reprogramming efficiency. The small molecules used were 1) sodium butyrate (0.5 mM), 2) glycogen synthase kinase 3β inhibitor of the Wnt/β-catenin signaling pathway (CHIR99021, 3 µM), 3) MEK pathway inhibitor (PD 0325901, 0.5 µM), 4) Selective inhibitor of TGF-β type I receptor ALK5 kinase, type I activin/nodal receptor ALK4 and type I nodal receptor ALK7 (A 83-01, 0.5 µM). Colonies with ES/iPSC-like morphology appeared 25-31 days later. Subsequently, colonies with the best morphology were transferred onto a feeder-independent 6 BD Matrigel™ Matrix and maintained in mTeSR®1 medium. The iPSC clones were further expanded and cryopreserved.

EZ spheres generated from iPSCs can be differentiated to a culture of neural progenitor cells in suspension (iNPCsSU), with astroglial predisposition. After EGF/FGF2/heparin withdrawal, EZ spheres were caudalized using retinoic acid RA (0.5 µM) in Neural Induction Media (NIM) (DMEM/F12, 1% NEAA, 1% N2, heparin 2 µg/ml; Sigma). This media was replaced every 2 days for the next 11 days, after which a stable population of iNPCsSU was reintroduced into StemHi E/F/H for expansion by weekly chopping (similar to EZ spheres). The iNPCsSU maintain their proliferative potential and astroglial generation propensity for 26-30 passages and can be efficiently cryopreserved. In addition, an adherent format of iNPCs grown as adherent cultures and termed iNPCsAD, were generated by accutase dissociation of EZ spheres for plating on growth-factor reduced Matrigel (Corning) at a density of 10,000 cells/cm2 in StemHi E/F/H and passaged weekly using TrypLE (Life Technologies). For differentiation to astrocytes, iNPCsSU were dissociated to single cells with accutase (BD Biosciences) or iNPCsAD harvested with TrypLE were plated on poly-1-ornithine/Matrigel coated glass coverslips at 25000 cells/cm2 in NIM for 7-21 days. Additional information can be found in Ebert et al., "EZ spheres: a stable and expandable culture system for the generation of pre-rosette multipotent stem cells from human ESCs and iPSCs" *Stem Cell Res*. 2013 May; 10(3):417-427.

Example 2

Transplantation

Nucleofected iNPCs, which underwent two rounds of FACS for BFP, were transplanted into the striatum (41 of cells at 100,000 cells/µl into each hemisphere) of 6-month old NOD-SCID mice (Nod.cb17-Prkdc$^{scid}$/J, Jackson Lab #1303; Bar Harbor, ME). Three days before transplantation, a subset of cells was treated with dox. For transplantation, cells were dissociated and diluted to a final concentration of 100,000 cells/µl in conditioned media, and maintained on ice. Animals were anesthetized with isoflurane and placed in a stereotaxic frame. Cells were injected bilaterally relative to bregma at 0.7 mm rostral and +/−2.0 mm lateral. A 5 µl Hamilton microsyringe backfilled with PBS was loaded with 2 µl of cell solution and inserted to a depth of −4.00 mm. The microsyringe was then raised to −3.50 mm and the cell solution was injected at 1 µl/min. After cell injection, the microsyringe was raised to −3.00 mm, held for 2 minutes and slowly withdrawn. Animals were checked daily.

Example 3

A New Vector to Provide Regulated Expression of Reporter Genes and GDNF

Tet-ON systems rely on constitutive expression of the rtTA-V10 transactivator and a dox-responsive TRE-Bi (Tet-Response Element Bi-directional) promoter. The Inventors observed that if the transactivator and inducible promoter are expressed in different plasmids and co-transfected into cells, the cells drifted during expansion and selected against doubly-transgenic populations, resulting in cells that are non-inducible (data not shown). Incorporating these elements as well as reporter genes in a single system requires a large vector, which was accomplished with the Inventors' newly created vector named "pB-RTP-Tet-GDNF/memClover-FLuc" [piggyBac-Reverse transactivator/TagBFP2nls/PacR-Tet inducible-GDNF/membrane Clover-Firefly Luciferase (FIG. 1A). The vector is flanked by piggyBac terminal repeats (PB TR) (FIG. 1A$_1$), which allows for its stable genomic integration when the pBase enzyme is transiently expressed.

The vector has two promoters—a constitutively active CMV/Chick β-Actin (aka CAG) promoter and an inducible, bi-directional TRE-Bi promoter. The CAG promoter (FIG. 1A$_2$) drives constitutive expression of the rtTA-V10 (aka tet-ON) transactivator (FIG. 1A$_3$), TagBFP2-V5nls (enhanced blue fluorescent protein with a V5 tag and nuclear localization sequence) (FIG. 1A$_4$), and the puromycin resistance gene (FIG. 1A$_5$). Transgenes in tandem are separated by self-cleaving peptide linkers (P2A). Addition of dox (FIG. 1A$_6$) to the system causes the rtTA-V10 transactivator to undergo a conformational change (FIG. 1A$_7$), allowing it to bind to the TRE-Bi promoter (FIG. 1A$_8$) and catalyze transcription of downstream transgenes; and withdrawal of dox reverses the induced gene expression. The first cistron of the TRE-Bi promoter harbors a myristoylated and palmitoylated (MyrPalm) clover reporter (mpClover) (FIG. 1A$_9$) followed by destabilized firefly luciferase (Luc2P) (FIG. 1A$_{10}$). Clover is a green fluorescent protein, which the MyrPalm sequences localizes to the cell membrane. A membrane fluorescent reporter was chosen in order to avoid visual overlap with perinuclear GDNF localization. Destabilized firefly luciferase (Luc2P), which has a half-life several folds less than wild-type luciferase, was used for analysis of gene expression in live animals over time. The second cistron downstream of the inducible TRE-Bi promoter harbors GDNF (FIG. 1A$_{11}$) followed by the woodchuck hepatitis virus post-transcriptional element (WPRE) for increased gene expression (FIG. 1A$_{12}$). Well-characterized rabbit beta-globin polyAs were placed downstream of the respective elements to terminate transcription and prevent spurious transgene expression. The pB-RTP-Tet-GDNF/memClover-FLuc vector is designed to be transfected alongside a pBase plasmid (FIG. 1B) to promote stable genomic integration (FIG. 1B$_1$). In summary, the presence or absence of dox dictates the expression of the inducible transgenes (Clover, luciferase, and GDNF), while the rtTA-v10 transactivator, TagBFP-v5-nls, and puromycin resistance genes are constitutively expressed (FIG. 1C). Additional information is found in PCT Pub. No. WO 2017/131926 and Akhtar et al. "A Transposon-Mediated System for Flexible Control of Transgene Expression in Stem and Progenitor-Derived Lineages" *Stem Cell Reports*. 2015 Mar. 10; 4(3): 323-331, which is fully incorporated by reference herein.

Example 4

Immunocytochemistry of Nucleofected iPSC-Derived NPCs

In order to promote cell adhesion, glass coverslips were coated with poly-ornithine (Sigma, P4638) and subsequently treated for 1 hour at 37° C. with 25 µl of laminin (50 µg/ml, Sigma-Aldrich L2020). Coating was then removed. Incubation in TrypLE for 5 minutes removed nucleofected cells from the 6-well plates. An equal volume of media was added to neutralize the enzymatic reaction, then dissociated cells were counted, pelleted at 150 rcf, resuspended in media at 1,000 cells/µl and 25 µl of cells were pipetted onto the laminin-coated region of the coverslip. Following a 4-6 hour incubation at 37° C. to permit cell adhesion, wells were gently flooded with 500 µl of growth media. Media was changed at half volume every 24 hours.

Immunocytochemistry was performed as previously described. Briefly, cells were fixed in 4% paraformaldehyde (PFA) for 12 minutes. The PFA solution was then removed and washed three times with Phosphate Buffered Saline (PBS) with a 5-minute incubation each. Cells were then incubated in primary antibodies [concentrations listed in Table 1] diluted in PBS with 0.3% Triton (PBS-T) and 3% normal donkey serum (NDS) for at least 12 hours at 4° C. on a gentle rocker, followed by three 5 min PBS washes at room temperature. Secondary antibodies (conjugated with Alexa405, FITC, Alexa488, Dylight488, Alexa555, Dylight549, Alexa647, or Dylight649; Jackson Immunoresearch, West Grove, PA) were diluted in PBS-T at a 1:1000 dilution and incubated for 1 hour at room temperature on a gentle rocker. Coverslips were then washed in PBS and mounted on glass slides with anti-fade mounting gel medium (Invitrogen ProLong Gold, P10144).

TABLE 1

Antibodies used in this study.

| Manufacturer | Host Species | Antigen | Dilution |
|---|---|---|---|
| Abcam 13970 | Chicken | EGFP | 1:2500 |
| Abcam 95038 | Goat | V5 | 1:1000 |
| Invitrogen 46-0705 | Mouse | V5 | 1:1000 |
| Abcam 9113 | Chicken | V5 | 1:250 |
| KeraFast EMU108 | Guinea Pig | mKate (BFP visualization) | 1:500 |
| R&D BAF212 | Goat | GDNF | 1:250 |
| Abcam ab21176 | Rabbit | Luciferase | 1:500 |
| Cellartis Y40400 | Mouse | Stem 101 (human nuclei) | 1:1000 |
| Cellartis Y40410 | Mouse | Stem 121 (human cytoplasm) | 1:2000 |

Example 5

ELISA

Media used for ELISA was devoid of EGF and FGF and composed of DMEM:F12 (70:30) supplemented with 1% Antibiotic-Antimycotic and 2% B27 without Vitamin A. Before media was added for an incubation period of 24 hours or 7 days, old media was aspirated and wells were washed twice with sterile PBS. Collected media was stored at −80° C. A GDNF ELISA was performed per manufacturer instructions (R&D Systems DY212; Minneapolis, MN).

Example 6

Imaging

After immunocytochemistry and immunohistochemistry fluorescent staining, confocal images were collected on a Nikon A1R inverted laser scanning confocal microscope with appropriate settings to sequentially image colors and avoid signal crosstalk. The exposure and saturation measures were utilized to capture the maximum dynamic range. Typically, after the exposure was set, the identical setting was reused for the subsequent samples in the group. ND2 image files were initially imported into ImageJ for manipulation of confocal Z-stacks or for isolation of individual channels from single z-slices for subsequent editing in Adobe Photoshop CS6. Image curves were adjusted for consistency of dynamic range and exposure in Photoshop CS6, cropped, and then imported into Adobe Illustrator CS6 for the preparation of final images.

Example 7

GDNF Scoring of Transplanted Tissue

Immunostained sections were photographed using a Leica DM200 LED microscope. Images were scored based on stain intensity of DAB GDNF stain by an observer blinded to the experiment conditions (dox vs no dox).

Example 8

Reporter Protein Production is Reversibly Regulated In Vitro

To assess the dox-regulated system in therapeutically-relevant cells, human iNPCs were nucleofected with the pB-RTP-Tet-GDNF/memClover-FLuc and pBase vectors. Nucleofected cells were grown as free-floating spheres (termed EZ spheres) that could be easily maintained and rapidly expanded. In the absence of dox, spheres constitutively expressed BFP$^+$, and within 24 hours of adding dox, spheres expressed both BFP$^+$ and GFP$^+$, indicating that the TRE-Bi promoter was responding to dox (FIG. 1D).

To quantitatively assess reporter expression from the TRE-Bi promoter, iNPCs were nucleofected as above, along with an Ef1-*Renilla* plasmid that constitutively expresses *Renilla* luciferase for protein normalization. A dual-luciferase assay revealed that cells expressed a ~1300-fold increase in firefly luciferase activity (normalized to *Renilla*) after a 24-hour dox treatment, and this returned to near basal levels upon dox withdrawal (FIG. 1E). To assess the kinetics of the TRE-Bi inducible promoter, firefly luciferase activity was quantified in a live culture of the nucleofected iNPCs grown in the presence of beetle luciferin (FIG. 1F). Results showed that firefly bioluminescence rapidly increased after the dox addition at time 0 and slowly decreased after dox removal (at 48 hours). In order to assess if the TRE-Bi promoter could be reversibly induced, the IncuCyte S3 Live-Cell Analysis system was used to take hourly images of the nucleofected iNPCs. Results showed that clover expression could be induced, reversed, and re-induced by adding, removing, and re-adding dox to the culture. As a clinically-relevant cell product would need to be expanded and banked, the Inventors assessed if the TRE-Bi promoter would remain functionally responsive with an extensive cell expansion and freeze. Flow analysis revealed that 83% of the constitutively BFP$^+$ cells were induced to express GFP (FIG. 5), demonstrating that the TRE-Bi promoter remained functional.

Example 9

GDNF Production is Reversibly Regulated In Vitro

To ensure that the Inventors' system could regulate a therapeutically relevant molecule, GDNF production was next assessed in nucleofected iNPCs. Immunofluorescence revealed that GDNF was not visible in cells in the absence of dox, which confirms the Inventors' previous report that wildtype cells do not produce GDNF. The reporter proteins Clover and luciferase were also not produced in the absence of dox, whereas BFP was produced under the constitutive promoter (FIG. 2A). In the presence of dox, GDNF as well as Clover and luciferase were detected, along with maintained BFP production (FIG. 2B). When dox was subsequently removed, GDNF and reporter gene production all ceased, while BFP was maintained (FIG. 2C).

In order to quantify the regulation of GDNF, ELISA was used on cells grown in the presence of dox (ON), absence of dox (OFF), in the presence then absence of dox (ON→OFF), and in the presence of dox for an extended period of time (ON→ON) wherein the media was not changed (FIG. 2D). Once again, cells did not produce appreciable levels of GDNF in the absence of dox. In contrast, cells produced robust levels of GDNF in the presence of dox after only 24 hours and this accumulated over 7 days of continuous dox treatment. Critically, GDNF could be reversibly turned on and returned to baseline levels based on the presence/absence of dox. Normalizing the ELISA results with stereological counts of GDNF-positive cells demonstrated that dox-treated cultures secreted 7.34×10' picograms of GDNF per GDNF-positive cell per hour. Collectively, the demonstration that proteins can be successfully induced and reversed in vitro sets the stage for protein regulation in cells following transplantation.

Example 10

Reporter Transgene Expression is Inducible and Reversible in iNPCs Transplants in the Adult Brain To investigate the ability of this system to regulate protein expression in vivo, nucleofected iNPCs were expanded and transplanted to the adult NOD-SCID mouse brain (FIG. 3A). During the in vitro expansion, cells underwent two rounds of FACS for nuclear BFP. The parent cell population contained 15.6% BFP$^+$, which were then expanded as neurospheres for 7-weeks and sorted a second time for BFP, which yielded 32.4% BFP$^+$ cells. Three weeks after the second sort, cells were divided into two groups, with one cell group receiving dox in culture for three days prior to transplantation and the other cell group receiving no dox. 6-month old NOD-SCID mice (n=14) were transplanted with 200,000 iNPCs into each striatal hemisphere, with 10 animals receiving cells pre-treated with dox and 4 animals receiving untreated cells. Animals did not receive dox before the transplant.

One day after transplantation, all ten animals transplanted with the dox-treated cells emitted luciferase signal above background, which was calculated based on the signal from the animal's hind region distal to the CNS (FIG. 3B-C, Week 0). To determine if the transplanted cells could be subsequently turned "ON" and "OFF" multiple times by dox administration and withdrawal, animals were separated into two groups and switched ON→OFF→ON→OFF→ON (Group A) or OFF→ON→OFF→ON (Group B). Weekly bioluminescence imaging demonstrated that dox effectively regulated the luciferase protein in vivo, both in representative animals that started the trial on dox and ended off dox as well as started off dox and ended on dox (FIG. 3B). Quantification of luciferase activity at the weekly imaging session confirmed both the increase in luciferase activity in dox-treated animals and the inducibility of gene expression over time (FIG. 3C). Collectively, this provides in vivo proof-of-principle for dox-inducible gene expression.

Example 11

GDNF Expression is Inducible and Reversible in iNPC Transplants

To confirm regulated GDNF expression in transplanted cells, animals were euthanized after the final imaging session and fluorescent immunohistochemistry assessed GDNF, Clover, and BFP production (FIG. 4). Transplants in an animal ending the trial on dox (FIG. 4A) and its littermate endeing the trial off dox (FIG. 4B) demonstrated BFP+ cells in the striatal region, yet Clover and GDNF were only detected in the dox animal. High magnification showed that host cells adjacent to the graft site may be taking up GDNF in the dox-treated animal (FIG. 4C, pink arrows), whereas this was not observed in the off-dox animal at (FIG. 4D). Collectively, these data reveal that GDNF secretion can be induced and reversed in iNPCs months after transplantation.

Finally, DAB staining, which provides a high sensitivity of protein detection and has effectively tracked human GDNF-expressing NPC transplants, was used to determine the levels and location of GDNF expression. (FIG. 6 shows DAB staining of littermate animals from FIG. 4). A blinded analysis revealed that all animals (except one, Animal #8) that ended the trial on dox exhibited increased GDNF signal, and none of the animals that ended the trial off dox exhibited GDNF signal (Table 2).

TABLE 2

Blinded Postmortem GDNF Scoring.

| Observation | Animal # | GDNF Str/CC | GDNF Meninges |
|---|---|---|---|
| Ended trial ON dox and had luciferase signal | 1 | ++ | − |
|  | 2 | ++ | + |
|  | 3 | ++ | ++ |
|  | 5 | + | − |
|  | 6 | − | +++ |
| Ended trial ON dox but no luciferase signal | 8 | − | − |
|  | 10 | − | + |
| Ended trial OFF dox and no luciferase signal | 7 | − | − |
|  | 9 | − | − |
|  | 11 | − | − |
|  | 12 | − | − |
|  | 14 | − | − |
|  | 15 | − | − |
| Ended trial OFF dox but had luciferase signal | 13 | − | − |

(−) no positive staining;
(+) slight staining;
(++) moderate staining;
(+++) extensive staining.
Str = Striatum.
CC = Corpus Callosum This analysis also revealed that the variations in bioluminescence intensity may be a result of varying graft location. Specifically, some animals that exhibited remarkably high bioluminescence signal had grafted cells in the meninges, which is likely due to cell reflux into the injection tract during needle retraction (FIG. 7). Overall, the extensive analysis of all study animals confirmed a strong correlation between bioluminescence signal and GDNF expression.

Example 12

Discussion

This report provides proof-of-concept that GDNF produced by engineered human neural progenitor cells can be tightly regulated across multiple cycles in vivo. This technology can be applied to other growth factors, providing a valuable means to protect neurons damaged in different disease. Using pB-RTP-Tet-GDNF/memClover-FLuc, the Inventors observed that dox penetrates the parenchymal transplant site to a level that allows for transgene activation from the inducible TRE-Bi promoter. The Inventors also report that transgene activity can be induced and reversed multiple cycles. Thus, GDNF administration can be attenuated or stopped if patients develop side-effects, desensitization, or other transgene-related phenomena during disease progression. Alternatively, the drug regimen could be varied to allow for re-sensitization of host receptors and signaling pathways. This is in stark contrast to ex vivo gene therapy with constitutive gene expression. Importantly, the amount of dox concentration required for gene control (15 μg dox/g weight) is below antimicrobial doses and does not increase the presence of dox-resistant bacteria or negatively affect the gut flora.

Interestingly, in comparison to the lentiviral transduction of human NPCs used for the current ALS clinical trial, the novel dox-catalyzed system provides nearly two-fold higher GDNF secretion. This increase may be attributed to piggyBac transposition that can mediate more copies of plasmid genomic insertion than lentiviral transduction. Furthermore, GDNF transcription with previous lentiviral experiments is dependent on the PGK promoter that is activated by endogenous transcription factors. In the present study, GDNF transcription is initiated by binding of the tet-ON transactivator to the TRE-Bi promoter that is catalyzed by a conformational change initiated by dox administration. Thus, transcription is not limited by a naturally occurring transcription factor, but rather the amount of transactivator and dox present. It is important to note that transplanting ex vivo genetically engineered neural progenitors as done in this study adds a level of safety compared to direct genetic manipulation of host cells by viral transduction of pB-RTP-Tet-GDNF/memClover-Flu. Specifically, direct viral transduction to the brain may not only target healthy cells neighboring diseased cells but also may further compromise diseased host cells. In addition, simply introducing healthy neural progenitor/stem cells, in it of itself, may have beneficial effects on the diseased host mileu in various diseases. Therefore, the synergistic effect of both cell and inducible gene therapy may surpass gene therapy alone. Especially when the neural cells are derived from a human iPSC source, critically providing the promise of autologous transplantation.

No animal exhibited abnormal behavior or any overt damage to the transplanted striatum based on examination of the brain. Importantly, no tumors or ectopic growths were observed in any of the transplant animals in this study or the Inventors' previous iPSC transplant studies. However, translating this therapy to the clinic will require further safety and efficacy testing. First, the long-term efficacy, toxicity, and potential antigenicity of the constitutively expressed transactivator (rtTA-V10) must be tested. Secondly, pBase in the Inventors' study was used as a means to stably integrate pB-RTP-Tet-GDNF/memClover-FLuc due to its ease of use. Though pBase mediates random integration, the Inventors have not seen tumors in over 500 mice where pBase was used. However, a clinical grade product may necessitate single-copy site-specific integration. Towards this end, targeting the AAVS1 safe landing may allow for long-term stable integration and methylation-resistant expression of transgenes. Importantly, the Inventors have observed marked dox-mediated transgene expression at the single-copy level using the same TRE-Bi promoter used in this study.

In conclusion, this proof-of-principle study lays the foundation for combined inducible gene and cell therapies that function to provide protection for the treatment of neurodegenerative diseases.

Example 13

Inducible Expression of Human GDNF from the AAVS1 "Safe Landing Site" in Human iPSC Cell Lines Applying the above constructs in a therapeutic setting would benefit greatly from "safe" integration to avoid deleterious effects. This includes, developing a DNA vector to produce Human GDNF, optionally including a controllable expression, which can be targeted for integration into the Human AAVS1 loci.

As a starting point, one utilizes the aforementioned human GDNF producing plasmid pB-RTP-Tet-GDNF/memClover-FLuc from the Breunig Laboratory at CSMC. The AAVS1 SA-2A-puro-pA donor plasmid was a gift from Rudolf Jaenisch (Addgene plasmid #22075; http://n2t.net/addgene:22075; RRID: Addgene_22075). One can modify the AAVS1 SA-2A-puro-pA donor plasmid to include a SfiI restriction site to facilitate cloning pB-RTP-Tet-GDNF/memClover-FLuc between the AAVS1 homology sequences. This new intermediate vector is named AAVS1-AVPT.

Intermediate vector AAVS1-AVPT and pB-RTP-Tet-GDNF/memClover-FLuc are digested with the restriction enzymes SalI and SfiI. The appropriate fragments were isolated and joined by DNA ligation. The resulting construct was confirmed by DNA sequencing and provisionally named AAVS1-teton-hGDNF. [SEQ ID NO: 2] as shown in FIG. 8. The AAVS1-teton-hGDNF construct was introduced into the human iPSC line CS0002iCTR-n11 by electroporation. Targeted integration into the AAVS1 loci is achieved by including the plasmids hAAVS1 1R TALEN and hAAVS1 1L TALEN (hAAVS1 1R TALEN was a gift from Feng Zhang (Addgene plasmid #35432; http://n2t.net/addgene:35432; RRID: Addgene_35432) hAAVS1 1L TALEN was a gift from Feng Zhang (Addgene plasmid #35431; http://n2t.net/addgene:35431; RRID:Addgene_35431)).

Example 14

Expression of GDNF in iPSC Cells

Cultures are maintained in the presence of the tetracycline analog doxycycline to facilitate identification of AAVS1-teton-hGDNF containing cells based on the expression of the fluorescent protein Clover. "Green" colonies were hand-picked under fluorescent microscopy for expansion. Once sufficient numbers of cells were produced the clones were further purified by FACS sorting. Simultaneously, culture media was collected from these clones to confirm GDNF production by ELISA assay.

Example 15

Cloned Single Copy Variants of the GDNF-Expressing Plasmids (TREBi and TRB3 Inducible Promoters Another example of the aforementioned includes single copy variants of the GDNF-expressing plasmids. Using TREBi and TRB3 inducible promoters, such vectors can include reports such as eGFP and Luc2. An example includes pDonor-Teton3g-2a-TagBFP-V5-nls-p2a-puroR WPRE_Insulated mpclover-2a-luc2pest-2a-gdnf wpre [SEQ ID NO: 3] as shown in FIG. 10. Such vector includes homologous recombination sequences. Here, AAVS1 targeting of the endogenous locus is between exon 1 and 2 of the human PPP1R12C gene. A recipient "landing site" includes a reporter/selection cassette (TagBFP2 and PuroR for fluorescent and antibiotic selection) driven by a splice acceptor linked to the upstream PPP1R12C and a constitutive CAG promoter driven td-Tomato red fluorescent cistron flanked by a LoxP and an FRT site were stable integrated. Subsequently, upon stable selection for these reporters, these cells were lipofected with a plasmid expressing FlpO and Cre and the donor plasmid containing a LoxP and FRT flanked selection/reporter cassette and a dox-inducible mpClover/Luc2p/GDNF cistron-containing plasmid.

Transmitted light and green fluorescence imaging of cells in the absence and presence of doxycycline demonstrates the inducibility of mpClover 24 hours after addition of dox and the absence of GFP "leakiness" in the absence of dox. Note that this population has not be selected on Puro, so it is not a pure population (thus, the negative cells do not contain the donor element). Moreover, these cells were examined roughly 1 week after a sorting to enrich transfected cells and 2 weeks after transfection so the mpClover populations are stable transfections. Dox inducibility would not function in the absence of integration.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the compositions and methods related to induced pluripotent stem cells (iPSCs), differentiated iPSCs including neural progenitor cells, vectors used for manipulation of the aforementioned cells, methods and compositions related to use of the aforementioned compositions, techniques and composition and use of solutions used therein, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventor for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of increasing glial derived neurotrophic factor (GDNF) levels in the central nervous system of an individual afflicted with a neurodegenerative disorder, the method comprising:
    administering to the central nervous system of the individual a plurality of induced pluripotent stem cell derived neural progenitor cells (iNPCs), wherein the iNPCs express a genomically integrated expression cassette comprising, in a single piggyBac vector:
        a constitutive promoter driving constitutive expression of rTA transactivator,
        an inducible, bi-directional polycistronic promoter comprising a tet response element, and
        a sequence encoding GDNF, wherein GDNF expression is inducible and reversible in the individual administered with the iNPCs; and
    administering to the individual a tetracycline-class antibiotic, wherein the tetracycline-class antibiotic leads to increased GDNF levels in the central nervous system of the individual.

2. The method according to claim 1, wherein the neurodegenerative disorder is selected from amyotrophic lateral sclerosis (ALS), Parkinson's, Huntington's, and Alzheimer's Diseases.

3. The method according to claim 1, wherein the central nervous system comprises a region of the brain and the region of the brain comprises the substantia nigra, the motor cortex, the entorhinal cortex and/or the hippocampus.

4. The method according to claim 1, wherein the individual is a human.

5. The method according to claim 1, wherein the genomically integrated expression cassette is integrated at a region of the genome with a reduced probability of oncogenic transformation for a cell comprising the genomically integrated expression cassette.

6. The method according to claim 1, wherein the genomically integrated expression cassette is integrated at a region of the genome selected from the group consisting of the adeno-associated virus site 1 (AAVS1), the chemokine (C-C motif) receptor 5 (CCR5) gene, and a human ortholog of the mouse Rosa26 locus.

7. The method according to claim 1, wherein the genomically integrated expression cassette is integrated by homologous recombination.

8. The method according to claim 1, wherein the genomically integrated expression cassette is integrated as a single-copy.

9. The method according to claim 1, wherein the plurality of iNPCs are administered to the brain of the individual, and wherein the tetracycline-class antibiotic induces transcription of a GDNF mRNA in the plurality of iNPCs.

10. A method of increasing glial derived neurotrophic factor (GDNF) levels in the central nervous system of a subject afflicted with a disease or condition, the method comprising:
    administering a quantity of cells to the central nervous system of the subject, wherein the cells express a therapeutic protein or peptide, and wherein the cells, therapeutic protein or peptide, or both, are capable of treating the disease or condition; and
    administering to the subject a tetracycline-class antibiotic, wherein the tetracycline-class antibiotic leads to increased GDNF levels in the central nervous system of the subject,
    wherein the cells are neural progenitor cells derived from induced pluripotent stem cells (iPSCs),
    wherein the therapeutic protein or peptide comprises a neurotrophic factor comprising GDNF,
    wherein the cells express an expression cassette from vectors and have been nucleofected, transfected, or electroporated,
    wherein the vectors comprise a piggyBac vector and a pBase vector that are nucleofected, transfected, or electroporated into the iPSC derived neural progenitor cells (iNPCs),
    wherein the piggyBac vector includes a constitutive promoter driving constitutive expression of rTA transactivator, an inducible, bi-directional polycistronic promoter comprising a tet response element, and a sequence encoding GDNF such that GDNF expression is inducible and reversible in the subject transplanted with the iNPCs, and
    wherein the disease or condition is a neurodegenerative disease.

11. The method of claim 10, wherein the sequence encoding GDNF which is operatively linked to the inducible, bi-directional polycistronic promoter, is located at one cistron downstream of the inducible, bi-directional polycistronic promoter-encodes GDNF.

12. The method of claim 10, wherein the quantity of cells are administered to the brain of the subject.

13. The method of claim 10, wherein the neurodegenerative disease is amyotrophic lateral sclerosis (ALS).

14. A method of increasing glial derived neurotrophic factor (GDNF) levels in the central nervous system of a subject afflicted with a neurodegenerative disease, the method comprising:
    administering a quantity of induced pluripotent stem cell derived neural progenitor cells (iNPCs) to the central nervous system of the subject, wherein the cells inducibly express a neurotrophic factor capable of treating the disease, wherein the iNPCs express a genomically integrated expression cassette introduced by nucleofection, the expression cassette comprising, in a single piggyBac vector:
        a constitutive promoter driving constitutive expression of rTA transactivator,
        an inducible, bi-directional polycistronic promoter comprising a tet response element, and
        a sequence encoding GDNF operatively linked to the inducible, bi-directional polycistronic promoter, wherein GDNF expression is inducible and reversible in the subject administered with the iNPCs; and administering to the subject a tetracycline-class antibiotic, wherein the tetracycline-class antibiotic leads to increased GDNF levels in the central nervous system of the subject.

15. The method of claim 14, wherein the single piggyBac vector is transfected to the iNPCs alongside a pBase plasmid.

16. The method of claim 14, wherein the iNPCs are administered to the brain of the subject.

17. A quantity of neural progenitor cells capable of inducible expression of glial derived neurotrophic factor (GDNF) comprising:
    a quantity of induced pluripotent stem cell derived neural progenitor cells (iNPCs), wherein the iNPCs express a genomically integrated expression cassette comprising, in a single piggyBac vector:
        a constitutive promoter driving constitutive expression of rTA transactivator,
        an inducible, bi-directional polycistronic promoter comprising a tet response element, and
        a sequence encoding GDNF,
    wherein GDNF expression is inducible and reversible in the iNPCs by addition or withdrawal of doxycycline.

18. A method of increasing GDNF levels in the central nervous system of a subject afflicted with a neurodegenerative disease, the method comprising:
    administering the cells of claim 17 to the central nervous system of the subject; and
    administering to the subject a tetracycline-class antibiotic, wherein the tetracycline-class antibiotic leads to increased GDNF levels in the central nervous system of the subject.

19. The method according to claim 1, wherein administering the plurality of iNPCs to the central nervous system of the individual includes injection.

\* \* \* \* \*

SEQUENCE LISTING

```
<160> NUMBER OF SEQ ID NOS: 3

<210> SEQ ID NO 1
<211> LENGTH: 12962
<212> TYPE: DNA
<213> ORGANISM: Artificial Sequence
<220> FEATURE:
<223> OTHER INFORMATION: pB-RTP-Tet-GDNF/memClover-FLuc

<400> SEQUENCE: 1
gtcgacttaa ccctagaaag ataatcatat tgtgacgtac gttaaagata atcatgcgta      60
```

```
aaattgacgc atgtgtttta tcgatctgta tatcgaggtt tatttattaa tttgaataga    120
tattaagttt tattatattt acacttacat actaataata aattcaacaa acaatttatt    180
tatgtttatt tatttattaa aaaaaaacaa aaactcaaaa tttcttctat aaagtaacaa    240 aactttact agttattaat agtaatcaat tacgggtca ttagttcata gcccatatat      300
ggagttccgc gttacataac ttacggtaaa tggcccgcct ggctgaccgc caacgaccc    360 ccgcccattg acgtcaataa tgacgtatgt tcccatagta acgccaatag gactttcca    420 ttgacgtcaa tgggtggagt atttacggta aactgcccac ttggcagtac atcaagtgta   480
tcatatgcca agtacgcccc ctattgacgt caatgacggt aaatgggccg cctggcatta   540
tgcccagtac atgaccttat gggactttcc tacttggcag tacatctacg tattagtcat   600
cgctattacc atgggtcgag gtgagcccca cgttctgctt cactctcccc atctcccccc   660
cctccccacc cccaattttg tatttatta ttttttaatt attttgtgca gcgatggggg    720 cgggggggggg gggggcgcgc gccaggcggg gcggggcggg gcgaggggcg gggcggggcg   780
aggcggagag gtgcggcggc agccaatcag agcggcgcgc tccgaaagtt tcctttatg    840 gcgaggcggc ggcggcggcg gccctataaa aagcgaagcg cgcggcgggc gggagtcgct    900
gcgttgcctt cgccccgtgc cccgctccgc gccgcctcgc gccgcccgcc ccggctctga    960
ctgaccgcgt tactcccaca ggtgagcggg cgggacggcc cttctcctcc gggctgtaat   1020
tagcgcttgg tttaatgacg gctcgtttct tttctgtggc tgcgtgaaag ccttaaaggg   1080
ctccgggagg gccctttgtg cggggggag cggctcgggg ggtgcgtgcg tgtgtgtgtg   1140
cgtggggagc gccgcgtgcg gcccgcgctg cccggcggct gtgagcgctg cgggcgcggc   1200 gcggggctt gtgcgctccg cgtgtgcgcg aggggagcgc ggccggggc ggtgccccgc    1260 ggtgcggggg ggctgcgagg ggaacaaagg ctgcgtgcgg ggtgtgtgcg tggggggtg   1320 agcaggggt gtgggcgcgg cggtcgggct gtaaccccc cctgcacccc cctccccgag    1380
ttgctgagca cggcccggct tcgggtgcgg ggctccgtgc ggggcgtggc gcggggctcg   1440
ccgtgccggg cgggggtgg cggcaggtgg gggtgccggg cggggcgggg ccgcctcggg    1500
ccggggaggg ctcgggggag gggcgcgcg gcccccggag cgccggcggc tgtcgaggcg    1560
cggcgagccg cagccattgc ctttatggt aatcgtgcga gagggcgcag ggacttcctt    1620
tgtcccaaat ctgtgcggag ccgaaatctg ggaggcgccg ccgcaccccc tctagcgggc   1680
gcggggcgaa gcggtgcggc gccggcagga aggaaatggg cggggagggc cttcgtgcgt   1740
cgccgcgccg ccgtccccctt ctccctctcc agcctcgggg ctgtccgcgg gggacggct    1800 gccttcgggg gggacggggc agggcggggt tcggcttctg gcgtgtgacc ggcggctcta   1860
gagcctctgc taaccatgtt catgccttct tcttttcct acagtcctg ggcaacgtgc    1920 tggttattgt gctgtctcat catttttggca aagaattcgg taccgcatgc atcgatgcta   1980
gcgcgccgcc accatgtcta gactggacaa gagcaaagtc ataaactctg ctctggaatt   2040
actcaatgga gtcggtatcg aaggcctgac gacaaggaaa ctcgctcaaa agctgggagt   2100
tgagcagcct accctgtact ggcacgtgaa gaacaagcgg gccctgctcg atgccctgcc   2160
aatcgagatg ctggacaggc atcatacca ctcctgcccc ctggaaggcg agtcatggca    2220
agactttctg cggaacaacg ccaagtcata ccgctgtgct ctcctctcac atcgcgacgg   2280
ggctaaagtg catctcggca cccgcccaac agagaaacag tacgaaaccc tggaaaatca   2340
gctcgcgttc ctgtgtcagc aaggcttctc cctggagaac gcactgtacg ctctgtccgc   2400
cgtgggccac tttacactgg gctgcgtatt ggaggaacag gagcatcaag tagcaaaaga   2460
```

-continued

```
ggaaagagag acacctacca ccgattctat gcccccactt ctgaaacaag caattgagct    2520
gttcgaccgg cagggagccg aacctgcctt ccttttcggc ctggaactaa tcatatgtgg    2580
cctggagaaa cagctaaagt gcgaaagcgg cgggccgacc gacgcccttg acgattttga    2640
cttagacatg ctcccagccg atgcccttga cgactttgac cttgatatgc tgcctgctga    2700
cgctcttgac gattttgacc ttgacatgct ccccggggga tccggaggat ccggagccac    2760
gaacttctct ctgttaaagc aagcaggaga cgtggaagaa accccggtc ctatgagcga     2820 gctgattaag gagaacatgc acatgaagct gtacatggag ggcaccgtgg acaaccatca    2880
cttcaagtgc acatccgagg gcgaaggcaa gccctacgag ggcacccaga ccatgagaat    2940
caaggtggtc gagggcggcc ctctcccctt cgccttcgac atcctggcta ctagcttcct    3000
ctacggcagc aagaccttca tcaaccacac ccagggcatc cccgacttct caagcagtc     3060 cttccctgag ggcttcacat gggagagagt caccacatac gaagacgggg gcgtgctgac    3120
cgctacccag gacaccagcc tccaggacgg ctgcctcatc tacaacgtca agatcagagg    3180
ggtgaacttc acatccaacg gccctgtgat gcagaagaaa cactcggct gggaggcctt     3240 caccgagacg ctgtaccccg ctgacggcgg cctggaaggc agaaacgaca tggccctgaa    3300
gctcgtgggc gggagccatc tgatcgcaaa cgccaagacc acatatagat ccaagaaacc    3360
cgctaagaac ctcaagatgc ctggcgtcta ctatgtggac tacagactgg aaagaatcaa    3420
ggaggccaac aacgagacct acgtcgagca gcacgaggtg gcagtggcca gatactgcga    3480
cctccctagc aaactggggc acaagcttaa ttccggactc ggcaagccta tccctaaccc    3540
tctgctgggc ctggacagca ccgatccaaa aaagaagaga aaggtagacc ctaagaagaa    3600
gaggaaggtg gaccccaaga agaagagaaa ggtgtgaggc agtggaggga gtggagcaac    3660 caattttca ctcctgaagc aagctgggga tgtagaggag aatcctgggc ctatggacta    3720
caaagacgat gacgacaagc ttggcactag tggctttgcg aatgaattgg gacctaggtt    3780
gatgggcaag ctttctagtc aactcgagat gaccgagtac aagcccacgg tgcgcctcgc    3840 caccgcgac gacgtcccca gggccgtacg caccctcgcc gccgcgttcg ccgactaccc    3900
cgccacgcgc cacaccgtcg atccggaccg ccacatcgag cgggtcaccg agctgcaaga    3960
actcttcctc acgcgcgtcg ggctcgacat cggcaaggtg tgggtcgcgg acgacggcgc    4020
cgcggtggcg gtctggacca cgccggagag cgtcgaagcg gggcggtgt tcgccgagat     4080 cggcccgcgc atggccgagt tgagcggttc ccggctggcc gcgcagcaac agatggaagg    4140
cctcctggcc ccgcaccggc ccaaggagcc gcgtggttc ctggccaccg tcggcgtctc     4200
gcccgaccac cagggcaagg gtctgggcag cgccgtcgtg ctccccggag tggaggcggc    4260
cgagcgcgcg gggtgcccg ccttcctgga gacctccgcg ccccgcaacc tccccttcta     4320
cgagcggctc ggcttcaccg tcaccgccga cgtcgaggtg cccgaaggac gcgcgcacctg    4380 gtgcatgacc cgcaagcccg gtgcctgagc ggccgcactc tcaggtgca ggctgcctat     4440 cagaaggtgg tggctggtgt ggccaatgcc ctggctcaca ataccactg agatcttttt     4500 ccctctgcca aaaattatgg ggacatcatg aagcccttg agcatctgac ttctggctaa     4560
taaaggaaat ttatttcat tgcaatagtg tgttggaatt ttttgtgtct ctcactcgga     4620
aggacatatg ggagggcaaa tcatttaaaa catcagaatg agtatttggt ttagagtttg    4680
gcaacatatg cccatatgct ggctgccatg aacaaaggtt ggctataaag aggtcatcag    4740
tatatgaaac agcccctgc tgtccattcc ttattccata gaaaagcctt gacttgaggt      4800
```

-continued

```
tagattttttt ttatattttg ttttgtgtta ttttttttctt taacatccct aaaattttcc      4860
ttacatgttt tactagccag attttttcctc ctctcctgac tactcccagt catagctgtc      4920
cctcttctct tatggagatc cctcgacctg ggtaacgcca gggttttccc agtcacgacg      4980
ttgtaaaacg acggccagtg ccaagcttgc atgcctgcag taagatacat tgatgagttt      5040
ggacaaacca caactagaat gcagtgaaaa aaatgcttta tttgtgaaat ttgtgatgct      5100
attgctttat ttgtaaccat tataagctgc aataaacaag ttaacaacaa caattgcatt      5160
cattttatgt ttcaggttca gggggaggtg tgggaggttt tttaaagcaa gtaaaacctc      5220
tacaaatgtg gtaggtacca ccggtcctgc aggttagacg ttgatcctgg cgctggcgca      5280
agcagcaggg tgtctatcca tgccgctctc ctgggcgcag ctcatgggca gggtgccggc      5340
ggcctgctcc tccacctcgg gagggaagcc gtgagaattc acggcgatct tgccgccctt      5400
cttggcctta atgagaatct cgcggatctt gcggcgtcc aacttgccgg tcagtccttt      5460
aggcacctcg tccacgaaca caacaccacc gcgcagcttc ttggcggttg taacctggct      5520
ggccacatag tccacgatct ccttctcggt catggttta ccgtgttcca gcacgacgac      5580
tgcggcgggc agctcgccgg catcgtcgtc gggcaggccg gcgacccggg cgtcgaagat      5640
gttggggtgt tgcagcagga tgctctccag ttcggctggg gctacctggt agcccttgta      5700
tttgatcagg ctcttcagcc ggtccacgat gaagaagtgc tcgtcctcgt cccagtaggc      5760
gatgtcgccg ctgtgcagcc agccgtcctt gtcgatgaga gcgtttgtag cctcggggtt      5820
gttaacgtag ccgctcatga tcatggggcc acggacgcac agctcgccgc gctggttcac      5880
acccagtgtc ttaccggtgt ccaagtccac caccttagcc tcgaagaagg gcaccacctt      5940
gcctactgcg ccaggcttgt cgtcccttc ggggtgatc agaatggcgc tggttgtttc      6000
tgtcaggccg tagccctggc ggatgcctgg taggtggaag cgtttggcca cggcctcacc      6060
tacctccttg ctgagcggcg ccccgccgct ggcgatctcg tgcaagttgc ttaggtcgta      6120
cttgtcgatg agagtgctct tagcgaagaa gctaaatagt gtgggcacca gcagggcaga      6180
ttgaatctta tagtcttgca agctgcgcaa gaatagctcc tcctcgaagc ggtacatgag      6240
cacgacccga aagccgcaga tcaagtagcc cagcgtggtg aacatgccga agccgtggtg      6300
aaatggcacc acgctgagga tagcggtgtc ggggatgatc tggttgccga agatggggtc      6360
gcgggcatga ctgaatcgga cacaagcggt gcggtgcgt agggctacgc ccttgggcaa      6420
tccggtactg ccactactgt tcatgatcag ggcgatggtt ttgtcccggt cgaagctctc      6480
gggcacgaag tcgtactcgt tgaagccggg tggcaaatgg gaagtcacga aggtgtacat      6540
gctttggaag ccctggtagt cggtcttgct atccatgatg atgatctttt gtatgatcgg      6600
tagcttcttt tgcacgttga ggatcttttg cagcccttc ttgctcacga atacgacggt      6660
gggctggctg atgcccatgc tgttcagcag ctcgcgctcg ttgtagatgt cgttagctgg      6720
ggccacagcc acaccgatga acagggcacc caacacgggc atgaagaact gcaagctatt      6780
ctcgctgcac accacgatcc gatggtttgt attcagccca tagcgcttca tagcttctgc      6840
cagccgaacg ctcatctcga agtactcggc gtaggtaatg tccacctcga tatgtgcgtc      6900
ggtaaaggcg atggtgccgg gcaccagggc gtagcgcttc atggctttgt gcagctgctc      6960
gccggcggtc ccgtcttcga gtgggtagaa tggcgctggg cccttcttaa tgttttttggc      7020 atcttccata ggaccggggt ttcttccac gtctcctgct tgctttaaca gagagaagtt      7080
cgtggctccg gatccggcgg cggttacgaa ctccagcagg accatgtgat cgcgcttctc      7140
gttggggtct ttgctcaggg cggactgatg gctcaggtag tggttgtcgg gcagcagcac      7200
```

-continued

```
ggggccgtcg ccgatggggg tgttctgctg gtagtggtcg gcgagctgca cgctgccgtc    7260
ctcaacgttg tggcggatct tgaagttagc cttgatgccg ttcttctgct tgtcggccgt    7320
gatatagacg ttgtggctgt tgaagttgta ctccagcttg tgccccagga tgttgccgtc    7380
ctccttgaag tcgatgccct tcagctcgat gcggttcacc agggtgtcgc cctcgaactt    7440
cacctcggcg cgggtcttgt aggtaccgtc gtccttgaaa gagatggtgc gctcctggac    7500
gtagccttcg ggcatggcgg acttgaagaa gtcgtgctgc ttcatgtggt cggggtagcg    7560
gctgaagcag gccacgccgt agccgaaggt ggtcacgagg gtgggccagg gcacgggcag    7620
cttgccggtg tgcagatga acttcagggt cagcttgccg ttggtggcat cgccctcgcc    7680
ctcgccgcgg acgctgaact tgtggccgtt tacgtcgccg tccagctcga ccaggatggg    7740
caccaccccg gtgaacagct cctcgccctt gctcaccatg tccacgccgt cgtcgttcag    7800
gttgtccttg cgcttgctct tgatgcagcc catggtggcg gcggtcacca cgcgtccgcg    7860
atctgacggt tcactaaacg agctctgctt ataggcct cccaccgtac acgccacctc     7920
gacatactcg agtttactcc ctatcagtga tagagaacgt atgaagagtt tactccctat    7980
cagtgataga gaacgtatgc agactttact ccctatcagt gatagagaac gtataaggag    8040
tttactccct atcagtgata gagaacgtat gaccagttta ctccctatca gtgatagaga    8100
acgtatctac agtttactcc ctatcagtga tagagaacgt atatccagtt tactccctat    8160
cagtgataga gaacgtataa gctttaggcg tgtacggtgg gcgcctataa aagcagagct    8220
cgtttagtga accgtcagat cgcctggagc aattccacaa cacttttgtc ttataccaac    8280
tttccgtacc acttcctacc ctcgtaaaca gctggccgcc accatgaagt tatgggatgt    8340
cgtggctgtc tgcctggtgc tgctccacac cgcgtccgcc ttcccgctgc ccgccggtaa    8400
gaggcctccc gaggcgcccg ccgaagaccg ctccctcggc cgccgccgcg cgcccttcgc    8460
gctgagcagt gactcaaata tgccagagga ttatcctgat cagttcgatg atgtcatgga    8520
ttttattcaa gccaccatta aaagactgaa aaggtcacca gataaacaaa tggcagtgct    8580
tcctagaaga gagcggaatc ggcaggctgc agctgccaac ccagagaatt ccagaggaaa    8640
aggtcggaga ggccagaggg gcaaaaaccg gggttgtgtc ttaactgcaa tacatttaaa    8700
tgtcactgac ttgggtctgg gctatgaaac caaggaggaa ctgattttta ggtactgcag    8760
cggctcttgc gatgcagctg agacaacgta cgacaaaata ttgaaaaact tatccagaaa    8820
tagaaggctg gtgagtgaca aagtagggca ggcatgttgc agacccatcg cctttgatga    8880
tgacctgtcg ttttagatg ataacctggt ttaccatatt ctaagaaagc attccgctaa     8940
aaggtgtgga tgtatctgat tcgaaagccg cactcctcat aatcaacctc tggattacaa    9000
aatttgtgaa agattgactg gtattcttaa ctatgttgct ccttttacgc tatgtggata    9060
cgctgcttta atgcctttgt atcatgctat tgcttcccgt atggctttca ttttctcctc    9120
cttgtataaa tcctggttgc tgtctcttta tgaggagttg tggcccgttg tcaggcaacg    9180
tggcgtggtg tgcactgtgt tgctgacgc aaccccact ggttgggca ttgccaccac       9240
ctgtcagctc ctttccggga ctttcgcttt cccctccct attgccacgg cggaactcat    9300
cgccgcctgc cttgcccgct gctggacagg gctcggctg ttgggcactg acaattccgt     9360
ggtgttgtcg gggaaatcat cgtcctttcc ttggctgctc gcctgtgttg ccacctggat    9420
tctgcgcggg acgtccttct gctacgtccc ttcggccctc aatccagcgg accttccttc    9480
ccgcggcctg ctgccggctc tgcggcctct tccgcgtctt cgccttcgcc ctcagacgag    9540
```

```
tcggatctcc ctttgggccg cctccccgca ggccgcacac ctcaggtgca ggctcgaaat   9600
ttaaatcctc gagggccgca ctcctcaggt gcaggctgcc tatcagaagg tggtggctgg   9660
tgtggccaat gccctggctc acaaatacca ctgagatctt tttccctctg ccaaaaatta   9720
tggggacatc atgaagcccc ttgagcatct gacttctggc taataaagga aatttatttt   9780
cattgcaata gtgtgttgga atttttgtg tctctcactc ggaaggacat atgggagggc   9840
aaatcattta aaacatcaga atgagtattt ggtttagagt ttggcaacat atgccatatg   9900
ctggctgcca tgaacaaagg tggctataaa gaggtcatca gtatatgaaa cagcccctg    9960 ctgtccattc cttattccat agaaaagcct tgacttgagg ttagattttt tttatatttt  10020
gttttgtgtt attttttttct ttaacatccc taaaattttc cttacatgtt ttactagcca 10080 gattttttcct cctctcctga ctactcccag tcatagctgt ccctcttctc ctgcagatat 10140
ctataacaag aaaatatata tataataagt tatcacgtaa gtagaacatg aaataacaat  10200
ataattatcg tatgagttaa atcttaaaag tcacgtaaaa gataatcatg cgtcatttg   10260 actcacgcgg tcgttatagt tcaaaatcag tgacacttac cgcattgaca agcacgcctc  10320
acgggagctc caagcggcga ctgagatgtc ctaaatgcac agcgacggat tcgcgctatt  10380
tagaaagaga gagcaatatt tcaagaatgc atgcgtcaat tttacgcaga ctatctttct  10440
agggttaagc ttggcgtaat catggtcata gctgtttcct gtgtgaaatt gttatccgct  10500
cacaattcca cacaacatac gagccggaag cataaagtgt aaagcctggg gtgcctaatg  10560
agtgagctaa ctcacattaa ttgcgttgcg ctcactgccc gctttccagt cgggaaacct  10620
gtcgtgccag cggatccgca tctcaattag tcagcaacca tagtcccgcc ctaactccg   10680 cccatcccgc ccctaactcc gcccagttcc gcccattctc cgccccatgg ctgactaatt  10740 tttttttattt atgcagaggc cgaggccgcc tcggcctctg agctattcca gaagtagtga 10800
ggaggctttt ttggaggcct aggcttttgc aaaaagctaa cttgtttatt gcagcttata  10860
atggttacaa ataaagcaat agcatcacaa atttcacaaa taaagcattt ttttcactgc  10920
attctagttg tggtttgtcc aaactcatca atgtatctta tcatgtctgg atccgctgca  10980
ttaatgaatc ggccaacgcg cggggagagg cggtttgcgt attgggcgct cttccgcttc  11040
ctcgctcact gactcgctgc gctcggtcgt tcggctgcgg cgagcggtat cagctcactc  11100
aaaggcggta atacggttat ccacagaatc aggggataac gcaggaaaga acatgtgagc  11160
aaaaggccag caaaaggcca ggaaccgtaa aaaggccgcg ttgctggcgt ttttccatag  11220
gctccgcccc cctgacgagc atcacaaaaa tcgacgctca agtcagaggt ggcgaaaccc  11280
gacaggacta taaagatacc aggcgtttcc ccctggaagc tccctcgtgc gctctcctgt  11340
tccgaccctg ccgcttaccg gatacctgtc cgcctttctc ccttcgggaa gcgtggcgct  11400
ttctcaatgc tcacgctgta ggtatctcag ttcggtgtag gtcgttcgct ccaagctggg  11460
ctgtgtgcac gaaccccccg ttcagcccga ccgctgcgcc ttatccggta actatcgtct  11520
tgagtccaac ccggtaagac acgacttatc gccactggca gcagccactg gtaacaggat  11580
tagcagagcg aggtatgtag gcggtgctac agagttcttg aagtggtggc ctaactacgg  11640
ctacactaga aggacagtat ttggtatctg cgctctgctg aagccagtta ccttcggaaa  11700
aagagttggt agctcttgat ccggcaaaca aaccaccgct ggtagcggtg gtttttttgt  11760
ttgcaagcag cagattacgc gcagaaaaaa aggatctcaa gaagatcctt tgatcttttc  11820 tacgggtct gacgctcagt ggaacgaaaa ctcacgttaa gggattttgg tcatgagatt   11880
atcaaaaagg atcttcacct agatcctttt aaattaaaaa tgaagtttta aatcaatcta  11940
```

```
aagtatatat gagtaaactt ggtctgacag ttaccaatgc ttaatcagtg aggcacctat    12000
ctcagcgatc tgtctatttc gttcatccat agttgcctga ctccccgtcg tgtagataac    12060
tacgatacgg gagggcttac catctggccc cagtgctgca atgataccgc gagacccacg    12120
ctcaccggct ccagatttat cagcaataaa ccagccagcc ggaagggccg agcgcagaag    12180
tggtcctgca actttatccg cctccatcca gtctattaat tgttgccggg aagctagagt    12240
aagtagttcg ccagttaata gtttgcgcaa cgttgttgcc attgctacag gcatcgtggt    12300
gtcacgctcg tcgtttggta tggcttcatt cagctccggt tcccaacgat caaggcgagt    12360
tacatgatcc cccatgttgt gcaaaaaagc ggttagctcc ttcggtcctc cgatcgttgt    12420
cagaagtaag ttggccgcag tgttatcact catggttatg gcagcactgc ataattctct    12480
tactgtcatg ccatccgtaa gatgcttttc tgtgactggt gagtactcaa ccaagtcatt    12540
ctgagaatag tgtatgcggc gaccgagttg ctcttgcccg gcgtcaatac gggataatac    12600
cgcgccacat agcagaactt taaaagtgct catcattgga aaacgttctt cggggcgaaa    12660
actctcaagg atcttaccgc tgttgagatc cagttcgatg taacccactc gtgcacccaa    12720
ctgatcttca gcatctttta ctttcaccag cgtttctggg tgagcaaaaa caggaaggca    12780
aaatgccgca aaaaagggaa taagggcgac acggaaatgt tgaatactca tactcttcct    12840
ttttcaatat tattgaagca tttatcaggg ttattgtctc atgagcggat acatatttga    12900
atgtatttag aaaaataaac aaataggggt tccgcgcaca tttccccgaa aagtgccacc    12960
tg                                                                   12962

<210> SEQ ID NO 2
<211> LENGTH: 16438
<212> TYPE: DNA
<213> ORGANISM: Artificial Sequence
<220> FEATURE:
<223> OTHER INFORMATION: AAVS1-teton-Hgdnf

<400> SEQUENCE: 2
gtcgacttaa ccctagaaag ataatcatat tgtgacgtac gttaaagata atcatgcgta      60
aaattgacgc atgtgtttta tcgatctgta tatcgaggtt tatttattaa tttgaataga     120
tattaagttt tattatattt acacttacat actaataata aattcaacaa acaatttatt     180
tatgtttatt tatttattaa aaaaaaacaa aaactcaaaa tttcttctat aaagtaacaa     240
aacttttact agttattaat agtaatcaat tacggggtca ttagttcata gcccatatat     300
ggagttccgc gttacataac ttacggtaaa tggcccgcct ggctgaccgc ccaacgaccc     360
ccgcccattg acgtcaataa tgacgtatgt tcccatagta acgccaatag gactttccca     420
ttgacgtcaa tgggtggagt atttacggta aactgcccac ttggcagtac atcaagtgta     480
tcatatgcca agtacgcccc ctattgacgt caatgacggt aaatggcccg cctggcatta     540
tgcccagtac atgaccttat gggactttcc tacttggcag tacatctacg tattagtcat     600
cgctattacc atgggtcgag gtgagcccca cgttctgctt cactctcccc atctcccccc     660
cctccccacc cccaattttg tatttattta ttttttaatt attttgtgca gcgatggggg     720
cggggggggg ggggcgcgc gccaggcggg gcggggcggg gcgaggggcg gggcggggcg     780
aggcggagag gtgcggcggc agccaatcag agcggcgcgc tccgaaagtt ccttttatg     840 gcgaggcggc ggcggcggcg gccctataaa aagcgaagcg cgcggcgggc gggagtcgct     900
gcgttgcctt cgccccgtgc cccgctccgc gccgcctcgc gccgcccgcc ccggctctga     960
```

-continued

```
ctgaccgcgt tactcccaca ggtgagcggg cgggacggcc cttctcctcc gggctgtaat   1020
tagcgcttgg tttaatgacg gctcgtttct tttctgtggc tgcgtgaaag ccttaaaggg   1080
ctccgggagg gcccttttgtg cggggggag cggctcgggg ggtgcgtgcg tgtgtgtgtg   1140
cgtggggagc gccgcgtgcg gcccgcgctg cccggcggct gtgagcgctg cgggcgcggc   1200
gcggggcttt gtgcgctccg cgtgtgcgcg aggggagcgc ggccggggc ggtgccccgc   1260
ggtgcggggg ggctgcgagg ggaacaaagg ctgcgtgcgg ggtgtgtgcg tggggggtg    1320
agcagggggt gtgggcgcgg cggtcgggct gtaaccccc cctgcacccc cctccccgag    1380
ttgctgagca cggcccggct tcgggtgcgg ggctccgtgc ggggcgtggc gcgggctcg    1440
ccgtgccggg cgggggtgg cggcaggtgg gggtgccggg cggggcgggg ccgcctcggg    1500
ccggggaggg ctcgggggag gggcgcgcg gcccccggag cgccggcggc tgtcgaggcg    1560
cggcgagccg cagccattgc cttttatggt aatcgtgcga gagggcgcag ggacttcctt   1620
tgtcccaaat ctgtgcgag ccgaaatctg ggaggcgccg ccgcaccccc tctagcgggc    1680
gcggggcgaa gcggtgcggc gccggcagga aggaaatggg cggggagggc cttcgtgcgt   1740
cgccgcgccg ccgtccccctt ctccctctcc agcctcgggg ctgtccgcgg gggacggct    1800
gccttcgggg ggacggggc agggcggggt tcggcttctg gcgtgtgacc ggcggctcta   1860
gagcctctgc taaccatgtt catgccttct tcttttttcct acagctcctg ggcaacgtgc   1920
tggttattgt gctgtctcat cattttggca aagaattcgg taccgcatgc atcgatgcta   1980
gcgcgccgcc accatgtcta gactggacaa gagcaaagtc ataaactctg ctctggaatt   2040
actcaatgga gtcggtatcg aaggcctgac gacaaggaaa ctcgctcaaa agctgggagt   2100
tgagcagcct accctgtact ggcacgtgaa gaacaagcgg gccctgctcg atgccctgcc   2160
aatcgagatg ctggacaggc atcataccca ctcctgcccc ctggaaggcg agtcatggca   2220
agactttctg cggaacaacg ccaagtcata ccgctgtgct ctcctctcac atcgcgacgg   2280
ggctaaagtg catctcggca cccgcccaac agagaaacag tacgaaaccc tggaaaatca   2340
gctcgcgttc ctgtgtcagc aaggcttctc cctggagaac gcactgtacg ctctgtccgc   2400
cgtgggccac tttacactgg gctgcgtatt ggaggaacag gagcatcaag tagcaaaaga   2460
ggaaagagag acacctacca ccgattctat gcccccactt ctgaaacaag caattgagct   2520
gttcgaccgg cagggagccg aacctgcctt ccttttcggc ctggaactaa tcatatgtgg   2580
cctggagaaa cagctaaagt gcgaaagcgg cgggccgacc gacgcccttg acgattttga   2640
cttagacatg ctcccagccg atgcccttga cgactttgac cttgatatgc tgcctgctga   2700
cgctcttgac gattttgacc ttgacatgct ccccgggga tccggaggat ccggagccac   2760
gaacttctct ctgttaaagc aagcaggaga cgtggaagaa aaccccgtc ctatgagcga   2820
gctgattaag gagaacatgc acatgaagct gtacatggag ggcaccgtgg acaaccatca   2880
cttcaagtgc acatccgagg gcgaaggcaa gccctacgag ggcacccaga ccatgagaat   2940
caaggtggtc gagggcggcc ctctcccctt cgccttcgac atcctggcta ctagcttcct   3000
ctacggcagc aagaccttca tcaaccacac ccagggcatc cccgacttct tcaagcagtc   3060
cttccctgag ggcttcacat gggagagagt caccacatac gaagacgggg gcgtgctgac   3120
cgctacccag acaccagcc tccaggacgg ctgcctcatc tacaacgtca agatcagagg   3180
ggtgaacttc acatccaacg gccctgtgat gcagaagaaa acactcggct gggaggcctt   3240
caccgagacg ctgtaccccg ctgacggcgg cctggaaggc agaaacgaca tggcctgaa   3300
gctcgtgggc gggagccatc tgatcgcaaa cgccaagacc acatatagat ccaagaaacc   3360
```

```
cgctaagaac ctcaagatgc ctggcgtcta ctatgtggac tacagactgg aaagaatcaa    3420
ggaggccaac aacgagacct acgtcgagca gcacgaggtg gcagtggcca gatactgcga    3480
cctccctagc aaactggggc acaagcttaa ttccggactc ggcaagccta tccctaaccc    3540
tctgctgggc ctggacagca ccgatccaaa aagaagaga aaggtagacc ctaagaagaa    3600
gaggaaggtg gaccccaaga agaagagaaa ggtgtgaggc agtggaggga gtggagcaac    3660 caattttca ctcctgaagc aagctgggga tgtagaggag aatcctgggc ctatggacta    3720
caaagacgat gacgacaagc ttggcactag tggctttgcg aatgaattgg gacctaggtt    3780
gatgggcaag ctttctagtc aactcgagat gaccgagtac aagcccacgg tgcgcctcgc    3840
cacccgcgac gacgtcccca gggccgtacg caccctcgcc gccgcgttcg ccgactaccc    3900
cgccacgcgc cacaccgtcg atccggaccc ccacatcgag cgggtcaccg agctgcaaga    3960
actcttcctc acgcgcgtcg ggctcgacat cggcaaggtg tgggtcgcgg acgacggcgc    4020
cgcggtggcg gtctggacca cgccggagag cgtcgaagcg ggggcggtgt cgccgagat    4080 cggcccgcgc atggccgagt tgagcggttc ccggctggcc gcgcagcaac agatggaagg    4140
cctcctggcg ccgcaccggc ccaaggagcc gcgcgtggttc ctggccaccg tcggcgtctc    4200
gcccgaccac cagggcaagg gtctgggcag cgccgtcgtg ctccccggag tggaggcggc    4260
cgagcgcgcc ggggtgcccg ccttcctgga gacctccgcg cccgcaacc tcccttcta    4320 cgagcggctc ggcttcaccg tcaccgccga cgtcgaggtg cccgaaggac cgcgcacctg    4380
gtgcatgacc cgcaagcccg gtgcctgagc ggccgcactc tcaggtgca ggctgcctat    4440 cagaaggtgg tggctggtgt ggccaatgcc ctggctcaca ataccactg agatctttt    4500 ccctctgcca aaattatgg ggacatcatg aagcccttg agcatctgac ttctggctaa    4560 taaggaaat ttattttcat tgcaatagtg tgttggaatt ttttgtgtct ctcactcgga    4620
aggacatatg ggagggcaaa tcatttaaaa catcagaatg agtatttggt ttagagtttg    4680
gcaacatatg cccatatgct ggctgccatg aacaaaggtt ggctataaag aggtcatcag    4740
tatatgaaac agcccctgc tgtccattcc ttattccata gaaaagcctt gacttgaggt    4800
tagatttttt ttatatttg ttttgtgtta ttttttctt taacatccct aaaatttttcc    4860 ttacatgttt tactagccag attttttcctc ctctcctgac tactcccagt catagctgtc    4920
cctcttctct tatggagatc cctcgacctg ggtaacgcca gggttttccc agtcacgacg    4980
ttgtaaaacg acggccagtg ccaagcttgc atgcctgcag taagatacat tgatgagttt    5040
ggacaaacca caactagaat gcagtgaaaa aaatgcttta tttgtgaaat ttgtgatgct    5100
attgctttat ttgtaaccat tataagctgc aataaacaag ttaacaacaa caattgcatt    5160
cattttatgt ttcaggttca gggggaggtg tgggaggttt tttaaagcaa gtaaaacctc    5220
tacaaatgtg gtaggtacca ccggtcctgc aggttagacg ttgatcctgg cgctggcgca    5280
agcagcaggg tgtctatcca tgccgctctc ctggcgcag ctcatgggca gggtgccggc    5340
ggcctgctcc tccacctcgg gagggaagcc gtgagaattc acggcgatct tgccgccctt    5400
cttggcctta atgagaatct cgcggatctt gcgggcgtcc aacttgccgg tcagtccttt    5460
aggcacctcg tccacgaaca caacaccacc gcgcagcttc ttggcggttg taacctggct    5520
ggccacatag tccacgatct ccttctcggt catggtttta ccgtgttcca gcacgacgac    5580
tgcggcgggc agctcgccgg catcgtcgtc gggcaggccg cgacccggg cgtcgaagat    5640 gttggggtgt tgcagcagga tgctctccag ttcggctggg gctacctggt agcccttgta    5700
```

```
tttgatcagg ctcttcagcc ggtccacgat gaagaagtgc tcgtcctcgt cccagtaggc    5760
gatgtcgccg ctgtgcagcc agccgtcctt gtcgatgaga gcgtttgtag cctcggggtt    5820
gttaacgtag ccgctcatga tcatggggcc acggacgcac agctcgccgc gctggttcac    5880
acccagtgtc ttaccggtgt ccaagtccac caccttagcc tcgaagaagg gcaccacctt    5940
gcctactgcg ccaggcttgt cgtcccctic ggggtgatc agaatggcgc tggttgtttc    6000
tgtcaggccg tagccctggc ggatgcctgg taggtggaag cgtttggcca cggcctcacc    6060
tacctccttg ctgagcggcg ccccgccgct ggcgatctcg tgcaagttgc ttaggtcgta    6120
cttgtcgatg agagtgctct tagcgaagaa gctaaatagt gtgggcacca gcagggcaga    6180
ttgaatctta tagtcttgca agctgcgcaa gaatagctcc tcctcgaagc ggtacatgag    6240
cacgacccga aagccgcaga tcaagtagcc cagcgtggtg aacatgccga agccgtggtg    6300
aaatggcacc acgctgagga tagcggtgtc ggggatgatc tggttgccga agatggggtc    6360
gcgggcatga ctgaatcgga cacaagcggt gcggtgcggt agggctacgc ccttgggcaa    6420
tccggtactg ccactactgt tcatgatcag ggcgatggtt ttgtcccggt cgaagctctc    6480
gggcacgaag tcgtactcgt tgaagccggg tggcaaatgg gaagtcacga aggtgtacat    6540
gctttggaag ccctggtagt cggtcttgct atccatgatg atgatctttt gtatgatcgg    6600
tagcttcttt tgcacgttga ggatctttg cagccctttc ttgctcacga atacgacggt    6660
gggctggctg atgcccatgc tgttcagcag ctcgcgctcg ttgtagatgt cgttagctgg    6720
ggccacagcc acaccgatga acagggcacc caacacgggc atgaagaact gcaagctatt    6780
ctcgctgcac accacgatcc gatggtttgt attcagccca tagcgcttca tagcttctgc    6840
cagccgaacg ctcatctcga agtactcggc gtaggtaatg tccacctcga tatgtgcgtc    6900
ggtaaaggcg atggtgccgg gcaccagggc gtagcgcttc atggctttgt gcagctgctc    6960
gccggcggtc ccgtcttcga gtgggtagaa tggcgctggg cccttcttaa tgttttggc    7020
atcttccata ggaccggggt tttcttccac gtctcctgct tgctttaaca gagagaagtt    7080
cgtggctccg gatccggcgg cggttacgaa ctccagcagg accatgtgat cgcgcttctc    7140
gttggggtct ttgctcaggg cggactgatg gctcaggtag tggttgtcgg gcagcagcac    7200
ggggccgtcg ccgatggggg tgttctgctg gtagtggtcg gcgagctgca cgctgccgtc    7260
ctcaacgttg tggcggatct tgaagttagc cttgatgccg ttcttctgct tgtcggccgt    7320
gatatagacg ttgtggctgt tgaagttgta ctccagcttg tgccccagga tgttgccgtc    7380
ctccttgaag tcgatgccct tcagctcgat gcggttcacc agggtgtcgc cctcgaactt    7440
cacctcggcg cgggtcttgt aggtaccgtc gtccttgaaa gagatggtgc gctcctggac    7500
gtagccttcg ggcatggcgg acttgaagaa gtcgtgctgc ttcatgtggt cggggtagcg    7560
gctgaagcag gccacgccgt agccgaaggt ggtcacgagg gtgggccagg gcacgggcag    7620
cttgccggtg gtgcagatga acttcagggt cagcttgccg ttggtggcat cgccctcgcc    7680
ctcgccgcgg acgctgaact gtggccgtt tacgtcgccg tccagctcga ccaggatggg    7740
caccaccccg gtgaacagct cctcgcccct gctcaccatg tccacgccgt cgtcgttcag    7800
gttgtccttg cgcttgctct tgatgcagcc catggtggcg gcggtcacca cgcgtccgcg    7860
atctgacggt tcactaaacg agctctgctt atataggcct cccaccgtac acgccacctc    7920
gacatactcg agtttactcc ctatcagtga tagagaacgt atgaagagtt tactccctat    7980
cagtgataga gaacgtatgc agactttact ccctatcagt gatagagaac gtataaggag    8040
tttactccct atcagtgata gagaacgtat gaccagttta ctccctatca gtgatagaga    8100
```

```
acgtatctac agtttactcc ctatcagtga tagagaacgt atatccagtt tactccctat    8160
cagtgataga gaacgtataa gctttaggcg tgtacggtgg gcgcctataa aagcagagct    8220
cgtttagtga accgtcagat cgcctggagc aattccacaa cacttttgtc ttataccaac    8280
tttccgtacc acttcctacc ctcgtaaaca gctggccgcc accatgaagt tatgggatgt    8340
cgtggctgtc tgcctggtgc tgctccacac cgcgtccgcc ttcccgctgc ccgccggtaa    8400
gaggcctccc gaggcgcccg ccgaagaccg ctccctcggc cgccgccgcg cgcccttcgc    8460
gctgagcagt gactcaaata tgccagagga ttatcctgat cagttcgatg atgtcatgga    8520
ttttattcaa gccaccatta aaagactgaa aaggtcacca gataaacaaa tggcagtgct    8580
tcctagaaga gagcggaatc ggcaggctgc agctgccaac ccagagaatt ccagaggaaa    8640
aggtcggaga ggccagaggg gcaaaaaccg ggggttgtgtc ttaactgcaa tacatttaaa    8700
tgtcactgac ttgggtctgg gctatgaaac caaggaggaa ctgattttta ggtactgcag    8760
cggctcttgc gatgcagctg agacaacgta cgacaaaata ttgaaaaact tatccagaaa    8820
tagaaggctg gtgagtgaca aagtagggca ggcatgttgc agacccatcg cctttgatga    8880
tgacctgtcg ttttttagatg ataacctggt ttaccatatt ctaagaaagc attccgctaa    8940
aaggtgtgga tgtatctgat tcgaaagccg cactcctcat aatcaacctc tggattacaa    9000
aatttgtgaa agattgactg gtattcttaa ctatgttgct cctttttacgc tatgtggata    9060 cgctgcttta atgcctttgt atcatgctat tgcttcccgt atggctttca ttttctcctc    9120
cttgtataaa tcctggttgc tgtctcttta tgaggagttg tggcccgttg tcaggcaacg    9180
tggcgtggtg tgcactgtgt ttgctgacgc aacccccact ggttgggca ttgccaccac    9240 ctgtcagctc ctttccggga ctttcgcttt ccccctccct attgccacgg cggaactcat    9300
cgccgcctgc cttgcccgct gctggacagg ggctcggctg ttgggcactg acaattccgt    9360
ggtgttgtcg gggaaatcat cgtcctttcc ttggctgctc gcctgtgttg ccacctggat    9420
tctgcgcggg acgtccttct gctacgtccc ttcggccctc aatccagcgg accttccttc    9480
ccgcggcctg ctgccggctc tgcggcctct tccgcgtctt cgccttcgcc ctcagacgag    9540
tcggatctcc ctttgggccg cctccccgca ggccgcacac ctcaggtgca ggctcgaaat    9600
ttaaatcctc gagggccgca ctcctcaggt gcaggctgcc tatcagaagg tggtggctgg    9660
tgtggccaat gccctggctc acaaatacca ctgagatctt tttccctctg ccaaaaatta    9720
tggggacatc atgaagcccc ttgagcatct gacttctggc taataaagga aatttatttt    9780
cattgcaata gtgtgttgga attttttgtg tctctcactc ggaaggacat atgggagggc    9840
aaatcattta aaacatcaga atgagtattt ggtttagagt ttggcaacat atgccatatg    9900
ctggctgcca tgaacaaagg tggctataaa gaggtcatca gtatatgaaa cagcccctg    9960 ctgtccattc cttattccat agaaaagcct tgacttgagg ttagattttt tttatatttt   10020
gttttgtgtt attttttct ttaacatccc taaaatttc cttacatgtt ttactagcca   10080 gattttctc cctctcctga ctactcccag tcatagctgt ccctcttctc ctgcagatat   10140
ctataacaag aaaatatata tataataagt tatcacgtaa gtagaacatg aaataacaat   10200
ataattatcg tatgagttaa atcttaaaag tcacgtaaaa gataatcatg cgtcattttg   10260
actcacgcgg tcgttatagt tcaaaatcag tgacacttac cgcattgaca agcacgcctc   10320
acgggagctc caagcggcga ctgagatgtc ctaaatgcac agcgacggat tcgcgctatt   10380
tagaaagaga gagcaatatt tcaagaatgc atgcgtcaat tttacgcaga ctatctttct   10440
```

```
agggttaagc ttggcgtaat catggtcata gctgtttcct gtgtgaaatt gttatccgct   10500
cacaattcca cacaacatac gagccggaag cataaagtgt aaagcctggg gtgcctaatg   10560
agtgagctaa ctcacattaa ttgcgttgcg ctcactgccc gctttccagt cgggaaacct   10620
gtcgtgccag cggatccgca tctcaattag tcagcaacca tagtcccgcc cctaactccg   10680
cccatcccgc ccctaactcc gcccagttcc gcccattctc cgccccatgg ctgactaatt   10740 tttttattt atgcagaggc cgaggccgcc tcggccagat ctctcgaggc cctgtgggag   10800
gaagagaaga ggtcagaagc ttgccccact gtggggtgga ggggacagat aaaagtaccc   10860
agaaccagag ccacattaac cggccctggg aatataaggt ggtcccagct cggggacaca   10920
ggatccctgg aggcagcaaa catgctgtcc tgaagtggac ataggggccc gggttggagg   10980
aagaagacta gctgagctct cggacccctg gaagatgcca tgacagggg ctggaagagc   11040 tagcacagac tagagaggta aggggggtag gggagctgcc caaatgaaag gagtgagagg   11100
tgacccgaat ccacaggaga acggggtgtc caggcaaaga aagcaagagg atggagaggt   11160
ggctaaagcc agggagacgg ggtactttgg ggttgtccag aaaaacggtg atgatgcagg   11220
cctacaagaa ggggaggcgg gacgcaaggg agacatccgt cggagaaggc catcctaaga   11280
aacgagagat ggcacaggcc ccagaaggag aaggaaaagg gaaccagcg agtgaagacg   11340 gcatggggtt gggtgaggga ggagagatgc ccggagagga cccagacacg gggaggatcc   11400
gctcagagga catcacgtgg tgcagcgccg agaaggaagt gctccggaaa gagcatcctt   11460
gggcagcaac acagcagaga gcaagggaa gagggagtgg aggaagacgg aacctgaagg   11520
aggcggcagg aaggatctg ggccagccgt agaggtgacc caggccacaa gctgcagaca   11580
gaaagcggca caggcccagg ggagagaatg ctggtcagag aaagcaaagg gcgaattcgt   11640
ttaaacctgc aggactagtc cctttagtga gggttaattc tgagcttggc gtaatcatgg   11700
tcatagctgt ttcctgtgtg aaattgttat ccgctcacaa ttccacacaa catacgagcc   11760
ggaagcataa agtgtaaagc ctggggtgcc taatgagtga gctaactcac attaattgcg   11820
ttgcgctcac tgcccgcttt ccagtcggga aacctgtcgt gccagctgca ttaatgaatc   11880
ggccaacgcg cggggagagg cggtttgcgt attgggcgct cttccgcttc ctcgctcact   11940
gactcgctgc gctcggtcgt tcggctgcgg cgagcggtat cagctcactc aaaggcggta   12000
atacggttat ccacagaatc aggggataac gcaggaaaga acatgtgagc aaaaggccag   12060
caaaaggcca ggaaccgtaa aaaggccgcg ttgctggcgt ttttccatag gctccgcccc   12120
cctgacgagc atcacaaaaa tcgacgctca agtcagaggt ggcgaaaccc gacaggacta   12180
taaagatacc aggcgtttcc ccctggaagc tccctcgtgc gctctcctgt tccgaccctg   12240
ccgcttaccg gatacctgtc cgcctttctc ccttcgggaa gcgtggcgct ttctcatagc   12300
tcacgctgta ggtatctcag ttcggtgtag tcgttcgct ccaagctggg ctgtgtgcac   12360
gaaccccccg ttcagcccga ccgctgcgcc ttatccggta actatcgtct tgagtccaac   12420
ccggtaagac acgacttatc gccactggca gcagccactg gtaacaggat tagcagagcg   12480
aggtatgtag gcggtgctac agagttcttg aagtggtggc ctaactacgg ctacactaga   12540
agaacagtat ttggtatctg cgctctgctg aagccagtta ccttcggaaa aagagttggt   12600
agctcttgat ccggcaaaca aaccaccgct ggtagcggtg gtttttttgt ttgcaagcag   12660
cagattacgc gcagaaaaaa aggatctcaa gaagatcctt tgatcttttc tacgggtct   12720 gacgctcagt ggaacgaaaa ctcacgttaa gggattttgg tcatgagaca ataaccctga   12780
taaatgcttc aataatattg aaaaaggaag agtatgagta ttcaacattt ccgtgtcgcc   12840
```

```
cttattccct tttttgcggc attttgcctt cctgttttg ctcacccaga aacgctggtg    12900
aaagtaaaag atgctgaaga tcagttgggt gcacgagtgg gttacatcga actggatctc    12960
aacagcggta agatccttga gagttttcgc cccgaagaac gttttccaat gatgagcact    13020
tttaaagttc tgctatgtgg cgcggtatta tcccgtattg acgccgggca agagcaactc    13080
ggtcgccgca tacactattc tcagaatgac ttggttgagt actcaccagt cacagaaaag    13140
catcttacgg atggcatgac agtaagagaa ttatgcagtg ctgccataac catgagtgat    13200
aacactgcgg ccaacttact tctgacaacg atcggaggac cgaaggagct aaccgctttt    13260
ttgcacaaca tggggatca tgtaactcgc cttgatcgtt gggaaccgga gctgaatgaa    13320
gccataccaa acgacgagcg tgacaccacg atgcctgtag caatggcaac aacgttgcgc    13380
aaactattaa ctggcgaact acttactcta gcttcccggc aacaattaat agactggatg    13440
gaggcggata agttgcagg accacttctg cgctcggccc ttccggctgg ctggtttatt    13500
gctgataaat ctggagccgg tgagcgtggg tctcgcggta tcattgcagc actggggcca    13560
gatggtaagc cctcccgtat cgtagttatc tacacgacgg ggagtcaggc aactatggat    13620
gaacgaaata gacagatcgc tgagataggt gcctcactga ttaagcattg gtaactgtca    13680
gaccaagttt actcatatat actttagatt gatttaaaac ttcattttta atttaaaagg    13740
atctaggtga agatccttt tgataatctc atgagcggat acatatttga atgtatttag    13800
aaaaataaac aaataggggt tccgcgcaca tttccccgaa aagtgccacc tgatgcggtg    13860
tgaaataccg cacagatgcg taaggagaaa ataccgcatc aggaaattgt aagcgttaat    13920
aattcagaag aactcgtcaa gaaggcgata gaaggcgatg cgctgcgaat cgggagcggc    13980
gataccgtaa agcacgagga agcggtcagc ccattcgccg ccaagctctt cagcaatatc    14040
acgggtagcc aacgctatgt cctgatagcg gtccgccaca cccagccggc cacagtcgat    14100
gaatccagaa aagcggccat tttccaccat gatattcggc aagcaggcat cgccatgggt    14160
cacgacgaga tcctcgccgt cgggcatgct cgccttgagc ctggcgaaca gttcggctgg    14220
cgcgagcccc tgatgctctt cgtccagatc atcctgatcg acaagaccgg cttccatccg    14280
agtacgtgct cgctcgatgc gatgtttcgc ttggtggtcg aatgggcagg tagccggatc    14340
aagcgtatgc agccgccgca ttgcatcagc catgatggat actttctcgg caggagcaag    14400
gtgagatgac aggagatcct gccccggcac ttcgcccaat agcagccagt cccttcccgc    14460
ttcagtgaca acgtcgagca cagctgcgca aggaacgccc gtcgtggcca gccacgatag    14520
ccgcgctgcc tcgtcttgca gttcattcag ggcaccggac aggtcggtct tgacaaaaag    14580
aaccgggcgc ccctgcgctg acagccggaa cacggcggca tcagagcagc cgattgtctg    14640
ttgtgcccag tcatagccga atagcctctc cacccaagcg gccggagaac ctgcgtgcaa    14700
tccatcttgt tcaatcatgc gaaacgatcc tcatcctgtc tcttgatcag agcttgatcc    14760
cctgcgccat cagatccttg gcggcaagaa agccatccag tttactttgc agggcttccc    14820
aaccttacca gagggcgccc cagctggcaa ttccggttcg cttgctgtcc ataaaaccgc    14880
ccagtctagc tatcgccatg taagcccact gcaagctacc tgctttctct ttgcgcttgc    14940
gttttccctt gtccagatag cccagtagct gacattcatc cggggtcagc accgtttctg    15000
cggactggct ttctacgtga aaaggatcta ggtgaagatc cttttgata atctcatgcc    15060 tgacatttat attccccaga acatcaggtt aatggcgttt ttgatgtcat tttcgcggtg    15120
gctgagatca gccacttctt ccccgataac ggagaccggc acactggcca tatcggtggt    15180
```

```
catcatgcgc cagctttcat ccccgatatg caccaccggg taaagttcac gggagacttt    15240
atctgacagc agacgtgcac tggccagggg gatcaccatc cgtcgcccg gcgtgtcaat     15300 aatatcactc tgtacatcca caaacagacg ataacggctc tctcttttat aggtgtaaac    15360
cttaaactgc cgtacgtata ggctgcgcaa ctgttgggaa gggcgatcgg tgcgggcctc    15420
ttcgctatta cgccagctgg cgaaaggggg atgtgctgca aggcgattaa gttgggtaac    15480 gccaggggttt tcccagtcac gacgttgtaa aacgacggcc agtgaattgt aatacgactc    15540 actataggc gaattgaatt tagcggccgc gaattcgccc ttgcccttag agcagagcca    15600 ggaaccctg tagggaaggg gcaggagagc caggggcatg agatggtgga cgaggaaggg     15660
ggacagggaa gcctgagcgc ctctcctggg cttgccaagg actcaaaccc agaagcccag    15720
agcagggcct tagggaagcg ggaccctgct ctgggcggag gaatatgtcc cagatagcac    15780
tggggactct ttaaggaaag aaggatggag aaagagaaag ggagtagagg cggccacgac    15840
ctggtgaaca cctaggacgc accattctca caaagggagt tttccacacg dacaccccc    15900 tcctcaccac agccctgcca ggacgggct ggctactggc cttatctcac aggtaaaact    15960
gacgcacgga ggaacaatat aaattgggga ctagaaaggt gaagagccaa agttagaact    16020
caggaccaac ttattctgat tttgttttc caaactgctt ctcctcttgg gaagtgtaag    16080
gaagctgcag caccaggatc agtgaaacgc accagacagc cgcgtcagag cagctcaggt    16140
tctgggagag ggtagcgcag ggtggccact gagaaccggg caggtcacgc atccccccct    16200
tccctcccac cccctgccaa gctctccctc ccaggatcct ctctggctcc atcgtaagca    16260
aaccttagag gttctggcaa ggagagagat ggctccagga aatgggggtg tgtcaccaga    16320
taaggaatct gcctaacagg aggtgggggt tagacccaat atcaggagac taggaaggag    16380
gaggcctaag gatggggctt ttctgtcacc aatcctgtcc ctagtaaagc ttagtact     16438
```

<210> SEQ ID NO 3
<211> LENGTH: 15067
<212> TYPE: DNA
<213> ORGANISM: Artificial Sequence
<220> FEATURE:
<223> OTHER INFORMATION: pDonor-Teton3g-2a-TagBFP-V5-nls-p2a-puroR
      WPRE_Insulated mpclover-2a-luc2pest-2a-gdnf wpre

<400> SEQUENCE: 3

```
ggtcgacatt gattattgac tagtggatcc gctgtaagtc tgcagaaatt gatgatctat      60
taaacaataa agatgtccac taaaatggaa gttttttcctg tcatactttg ttaagaaggg     120
tgagaacaga gtacctacat tttgaatgga aggattggag ctacggggg gggggtgggg      180 tgggattaga taaatgcctg ctctttactg aaggctcttt actattgctt tatgataatg     240
tttcatagtt ggatatcata atttaaacaa gcaaaaccaa attaagggcc agctcattcc     300
tcccactcat gatctataga tctatagatc tctcgtggga tcattgtttt tctcttgatt     360
cccactttgt ggttctaagt actgtggttt ccaaatgtgt cagtttcata gcctgaagaa     420
cgagatcagc agcctctgtt ccacatacac ttcattctca gtattgtttt gccaagttct     480
aattccatca gaagcttgca gatctgcgac tctagaggat ctgcgactct agaggatcat     540
aatcagccat accacatttg tagaggtttt acttgcttta aaaaacctcc cacacctccc     600
cctgaacctg aaacataaaa tgaatgcaat tgttgttgtt aacttgttta ttgcagctta     660
taatggttac aaataaagca atagcatcac aaatttcaca ataaagcat ttttttcact      720 gcattctagt tgtggtttgt ccaaactcat caatgtatct tatcatgtct ggatctgcga     780
```

```
ctctagagga tcataatcag ccataccaca tttgtagagg ttttacttgc tttaaaaaac    840
ctcccacacc tccccctgaa cctgaaacat aaaatgaatg caattgttgt tgttaacttg    900
tttattgcag cttataatgg ttacaaataa agcaatagca tcacaaattt cacaaataaa    960
gcattttttt cactgcattc tagttgtggt ttgtccaaac tcatcaatgt atcttatcat   1020
gtctggatct gcgactctag aggatcataa tcagccatac cacatttgta gaggttttac   1080
ttgctttaaa aaacctccca cacctccccc tgaacctgaa acataaaatg aatgcaattg   1140
ttgttgttaa cttgtttatt gcagcttata atggttacaa ataaagcaat agcatcacaa   1200
atttcacaaa taaagcattt ttttcactgc attctagttg tggtttgtcc aaactcatca   1260
atgtatctta tcatgtctgg atccccatca agctgatccg gaacccttaa tataacttcg   1320
tatagcatac attatacgaa gttattaggt ccctcgacct gcagcccaag ctagcttatc   1380
gatgctagcc agctgaccgg tggccgccac catgtctaga ctggacaaga gcaaagtcat   1440
aaactctgct ctggaattac tcaatggagt cggtatcgaa ggcctgacga caaggaaact   1500
cgctcaaaag ctgggagttg agcagcctac cctgtactgg cacgtgaaga caagcgggc   1560 cctgctcgat gccctgccaa tcgagatgct ggacaggcat catacccact cctgccccct   1620
ggaaggcgag tcatggcaag actttctgcg gaacaacgcc aagtcatacc gctgtgctct   1680
cctctcacat cgcgacgggg ctaaagtgca tctcggcacc cgcccaacag agaaacagta   1740
cgaaaccctg gaaaatcagc tcgcgttcct gtgtcagcaa ggcttctccc tggagaacgc   1800
actgtacgct ctgtccgccg tgggccactt acactgggc tgcgtattgg aggaacagga   1860
gcatcaagta gcaaaagagg aaagagagac acctaccacc gattctatgc ccccacttct   1920
gaaacaagca attgagctgt tcgaccggca gggagccgaa cctgccttcc ttttcggcct   1980
ggaactaatc atatgtggcc tggagaaaca gctaaagtgc gaaagcggcg ggccgaccga   2040
cgcccttgac gattttgact tagacatgct cccagccgat gcccttgacg actttgacct   2100
tgatatgctg cctgctgacg ctcttgacga ttttgacctt gacatgctcc ccggggatc   2160 cggaggatcc ggagccacga acttctctct gttaaagcaa gcaggagacg tggaagaaaa   2220
ccccggtcct atgagcgagc tgattaagga gaacatgcac atgaagctgt acatggaggg   2280
caccgtggac aaccatcact tcaagtgcac atccgagggc gaaggcaagc cctacgaggg   2340
cacccagacc atgagaatca aggtggtcga gggcggccct ctccccttcg ccttcgacat   2400
cctggctact agcttcctct acggcagcaa gaccttcatc aaccacaccc agggcatccc   2460
cgacttcttc aagcagtcct tccctgaggg cttcacatgg gagagagtca ccacatacga   2520 agacggggc gtgctgaccg ctacccagga caccagcctc caggacggct gcctcatcta   2580
caacgtcaag atcagagggg tgaacttcac atccaacggc cctgtgatgc agaagaaaac   2640
actcggctgg gaggccttca ccgagacgct gtaccccgct gacggcggcc tggaaggcag   2700
aaacgacatg gccctgaagc tcgtgggcgg gagccatctg atcgaaacg ccaagaccac   2760 atatagatcc aagaaacccg ctaagaacct caagatgcct ggcgtctact atgtggacta   2820
cagactggaa agaatcaagg aggccaacaa cgagacctac gtcgagcagc acgaggtggc   2880
agtggccaga tactgcgacc tccctagcaa actggggcac aagcttaatt ccggactcgg   2940
caagcctatc cctaacccct gctgggcct ggacagcacc gatccaaaaa agaagagaaa   3000
ggtagaccct aagaagaaga ggaaggtgga ccccaagaag aagagaaagg tgtgaggcag   3060
tggagggagt ggagcaacca atttttcact cctgaagcaa gctggggatg tagaggaga   3120 tcctgggcct atggactaca agacgatga cgacaagctt ggcactagtg gctttgcgaa   3180
```

```
tgaattggga cctaggttga tgggcaagct ttctagtcaa ctcgagatga ccgagtacaa   3240
gcccacggtg cgcctcgcca cccgcgacga cgtccccagg gccgtacgca ccctcgccgc   3300
cgcgttcgcc gactacccg ccacgcgcca caccgtcgat ccggaccgcc acatcgagcg    3360
ggtcaccgag ctgcaagaac tcttcctcac gcgcgtcggg ctcgacatcg gcaaggtgtg   3420
ggtcgcggac gacggcgccg cggtggcggt ctggaccacg ccggagagcg tcgaagcggg   3480
ggcggtgttc gccgagatcg gcccgcgcat ggccgagttg agcggttccc ggctggccgc   3540
gcagcaacag atggaaggcc tcctggcgcc gcaccggccc aaggagcccg cgtggttcct   3600
ggccaccgtc ggcgtctcgc ccgaccacca gggcaagggt ctgggcagcg ccgtcgtgct   3660
ccccggagtg gaggcggccg agcgcgccgg ggtgcccgcc ttcctggaga cctccgcgcc   3720
ccgcaacctc cccttctacg agcggctcgg cttcaccgtc accgccgacg tcgaggtgcc   3780
cgaaggaccg cgcacctggt gcatgacccg caagcccggt gcctgatacg tagcggccgc   3840
taatcaacct ctggattaca aaatttgtga agattgact ggtattctta actatgttgc    3900
tccttttacg ctatgtggat acgctgcttt aatgcctttg tatcatgcta ttgcttcccg   3960
tatggctttc attttctcct ccttgtataa atcctggttg ctgtctcttt atgaggagtt   4020
gtggcccgtt gtcaggcaac gtggcgtggt gtgcactgtg tttgctgacg caacccccac   4080
tggttggggc attgccacca cctgtcagct ccttccggg actttcgctt tcccctccc    4140 tattgccacg gcggaactca tcgccgcctg ccttgcccgc tgctggacag gggctcggct   4200
gttgggcact gacaattccg tggtgttgtc ggggaaatca tcgtcctttc cttggctgct   4260
cgcctgtgtt gccacctgga ttctgcgcgg gacgtccttc tgctacgtcc cttcggccct   4320
caatccagcg gaccttcctt cccgcggcct gctgccggct ctgcggcctc ttccgcgtct   4380
tcgccttcgc cctcagacga gtcggatctc ccttttgggc gcctcccgc aggccgcact    4440 cctcaggtgc aggctgccta tcagaaggtg gtggctggtg tggccaatgc cctggctcac   4500
aaataccact gagatctttt tccctctgcc aaaaattatg gggacatcat gaagcccctt   4560
gagcatctga cttctggcta ataaaggaaa tttattttca ttgcaatagt gtgttggaat   4620 ttttttgtgtc tctcactcgg aaggacatat gggagggcaa atcatttaaa acatcagaat   4680
gagtatttgg tttagagttt ggcaacatat gcccatatgc tggctgccat gaacaaggt    4740 tggctataaa gaggtcatca gtatatgaaa cagcccctg ctgtccattc cttattccat    4800
agaaaagcct tgacttgagg ttagattttt tttatatttt gttttgtgtt attttttct    4860 ttaacatccc taaaattttc cttacatgtt ttactagcca gattttttcct cctctcctga   4920 ctactcccag tcatagctgt ccctcttctc ttatggagat ccctcgacct gcagatcctc   4980
tagcgataag cttgatatcg aattcgagtt ggcgcgcctg tcattctaaa tctctctttc   5040
agcctaaagc tttttccccg tatccccca ggtgtctgca ggctcaaaga gcagcgagaa    5100
gcgttcagag gaaagcgatc ccgtgccacc ttccccgtgc ccgggctgtc cccgcacgct   5160
gccggctcgg ggatgcgggg ggagcgccgg accggagcgg agcccgggc ggctcgctgc    5220 tgcccctag cggggaggg acgtaattac atccctgggg gctttgggag ggggctgtcc     5280
ccgtgagctc ccaggcgcgc ctgtcattct aaatctctct ttcagcctaa agcttttttcc  5340 ccgtatcccc ccaggtgtct gcaggctcaa agagcagcga gaagcgttca gaggaaagcg   5400
atcccgtgcc accttccccg tgcccggggct gtccccgcac gctgccggct cggggatgcg   5460
gggggagcgc cggaccggag cggagccccg ggcggctcgc tgctgccccc tagcggggga   5520
```

-continued

```
gggacgtaat tacatccctg ggggctttgg ggggggctg tccccgtgag ctcaataaaa   5580
gagcccacaa cccctcactc ggcgcgccag tcctccgata gactgcgtcg cccgggtacc   5640
cgtgtatcca ataaaccctc ttgcagttta ccagccctc actccttctc tagggcgatc   5700
gccgccggaa ttcgttcctc ctggctgcac ctgccgcagt gcacagtccg gctgaggtgc   5760
acgggagccc gccggcctct ctctgcccgc gtccgtccgt gaaattccgg ccggggctca   5820
ccgcgatggc cctcccgaca ccctcggaca gcaccctccc cgcggaagcc cggggacgag   5880
gacggccacg gagactcgtt tggacccga gccaaagcga ggccctgcga gcctgctttg   5940
agcggaaccc gtaccgggc atcgccacca gagaacggct ggcccaggcc atcggcattc   6000
cggagcccag ggtccagatt tggtttcaga atgagaggtc acgccagctg aggcagcacc   6060
ggcgggaatc tcggcctgg cccgggagac gcggcccgcc agaaggcgg cgaaagcgga   6120
ccgccgtcac cggatcccag accgccctgc tcctccgagc ctttgagaag gatcgctttc   6180
caggcatcgc cgcccgggag gagctggcca gagagacggg cctccggag tccaggattc   6240
agatctggtt tcagaatcga agggccaggc acccgggaca gggtggcagg gcgcccgcgc   6300
aggcaggcgg cctgtgcagc gcggccccg gcggggtca ccctgctccc tcgtgggtcg   6360
ccttcgccca caccggcgcg tggggaacgg ggcttcccgc accccacgtg ccctgcgcgc   6420
ctgggctct cccacagggg gctttcgtga gccaggcagc gagggccgcc ccgcgctgc   6480
agcccagcca ggccgcgccg gcagagggg tctcccaacc tgccccggcg cgcggggatt   6540
tcgcctacgc cgccccggct cctccggagc cggggcgctc tcccaccctc aggctcctcg   6600
gtggcctccg cacccgggca aaagccggga ggaccgggac ccgcagcgcg acggcctgcc   6660
gggcccctgc gcggtggcac agcctgggcc cgctcaagcg gggccgcagg ccaaggggtg   6720
cttgcgccac ccacgtccca ggggagtccg tggtggggct ggggccgggg tccccaggtc   6780
gccggggcgg cgtgggaacc ccaagccggg gcagctccac ctccccagcc cgcgcccccg   6840
ggacgcctcc gcctccgcgc ggcagggca gatgcaaggc atcccggcgc cctcccaggc   6900
gctccaggag ccggcgccct ggtctgcact cccctgcggc ctgctgctgg atgagctcct   6960
ggcgagcccg gagtttctgc agcaggcgca acctctccta gaaacggagg ccccggggga   7020
gctggaggaa caagctttgc aaagatggat aaagttttaa acagagagga atctttgcag   7080
ccttaagttt actccctatc agtgatagag aacgtatgaa gagtttactc cctatcagtg   7140
atagagaacg tatgcagact ttactcccta tcagtgatag agaacgtata aggagtttac   7200
tccctatcag tgatagagaa cgtatgacca gtttactccc tatcagtgat agagaacgta   7260
tctacagttt actccctatc agtgatagag aacgtatatc agtttactc cctatcagtg   7320
atagagaacg tataagcttt aggcgtgtac ggtgggcgcc tataaaagca gagctcgttt   7380
agtgaaccgt cagatcgcct ggagcaattc cacaacactt ttgtcttata ccaactttcc   7440
gtaccacttc ctaccctcgt aaacagacgc gtggtgaccg ccgccaccat gggctgcatc   7500
aagagcaagc gcaaggacaa cctgaacgac gacgcgtgg acatggtgag caagggcgag   7560
gagctgttca ccggggtggt gcccatcctg gtcgagctgg acggcgacgt aaacggccac   7620
aagttcagcg tccgcggcga gggcgagggc gatgccacca acggcaagct gaccctgaag   7680
ttcatctgca ccaccggcaa gctgcccgtg cctggcccca ccctcgtgac caccttcggc   7740
tacggcgtgg cctgcttcag ccgctacccc gaccacatga agcagcacga cttcttcaag   7800
tccgccatgc ccgaaggcta cgtccaggag cgcaccatct ctttcaagga cgacggtacc   7860
tacaagaccc gcgccgaggt gaagttcgag ggcgacaccc tggtgaaccg catcgagctg   7920
```

```
aagggcatcg acttcaagga ggacggcaac atcctggggc acaagctgga gtacaacttc   7980
aacagccaca acgtctatat cacggccgac aagcagaaga acggcatcaa ggctaacttc   8040
aagatccgcc acaacgttga ggacggcagc gtgcagctcg ccgaccacta ccagcagaac   8100
accccatcg gcgacggccc cgtgctgctg cccgacaacc actacctgag ccatcagtcc   8160
gccctgagca aagaccccaa cgagaagcgc gatcacatgg tcctgctgga gttcgtaacc   8220
gccgccggat ccggagccac gaacttctct ctgttaaagc aagcaggaga cgtggaagaa   8280
aaccccgggc ctatggaaga tgccaaaaac attaagaagg cccagcgcc attctaccca    8340
ctcgaagacg ggaccgccgg cgagcagctg cacaaagcca tgaagcgcta cgccctggtg   8400
cccggcacca tcgcctttac cgacgcacat atcgaggtgg acattaccta cgccgagtac   8460
ttcgagatga gcgttcggct ggcagaagct atgaagcgct atgggctgaa tacaaaccat   8520
cggatcgtgg tgtgcagcga gaatagcttg cagttcttca tgcccgtgtt gggtgccctg   8580
ttcatcggtg tggctgtggc cccagctaac gacatctaca cgagcgcga gctgctgaac    8640
agcatgggca tcagccagcc caccgtcgta ttcgtgagca agaaagggct gcaaaagatc   8700
ctcaacgtgc aaaagaagct accgatcata caaaagatca tcatcatgga tagcaagacc   8760
gactaccagg gcttccaaag catgtacacc ttcgtgactt cccatttgcc acccggcttc   8820
aacgagtacg acttcgtgcc cgagagcttc gaccgggaca aaaccatcgc cctgatcatg   8880
aacagtagtg gcagtaccgg attgcccaag ggcgtagccc taccgcaccg caccgcttgt   8940
gtccgattca gtcatgcccg cgaccccatc ttcggcaacc agatcatccc cgacaccgct   9000
atcctcagcg tggtgccatt tcaccacggc ttcggcatgt tcaccacgct gggctacttg   9060
atctgcggct ttcgggtcgt gctcatgtac cgcttcgagg aggagctatt cttgcgcagc   9120
ttgcaagact ataagattca atctgccctg ctggtgccca cactatttag cttcttcgct   9180
aagagcactc tcatcgacaa gtacgaccta agcaacttgc acgagatcgc cagcggcggg   9240
gcgccgctca gcaaggaggt aggtgaggcc gtggccaaac gcttccacct accaggcatc   9300
cgccagggct acggcctgac agaaacaacc agcgccattc tgatcacccc cgaaggggac   9360
gacaagcctg gcgcagtagg caaggtggtg cccttcttcg aggctaaggt ggtggacttg   9420
gacaccggta agacactggg tgtgaaccag cgcggcgagc tgtgcgtccg tggccccatg   9480
atcatgagcg gctacgttaa caaccccgag gctacaaacg ctctcatcga caaggacggc   9540
tggctgcaca gcggcgacat cgcctactgg gacgaggacg agcacttctt catcgtggac   9600
cggctgaaga gcctgatcaa atacaagggc taccaggtag ccccagccga actggagagc   9660
atcctgctgc aacaccccaa catcttcgac gccggggtcg ccggcctgcc cgacgacgat   9720
gccggcgagc tgcccgccgc agtcgtcgtg ctggaacacg gtaaaaccat gaccgagaag   9780
gagatcgtgg actatgtggc cagccaggtt acaaccgcca agaagctgcg cggtggtgtt   9840
gtgttcgtgg acgaggtgcc taaaggactg accggcaagt tggacgcccg caagatccgc   9900
gagattctca ttaaggccaa gaagggcggc aagatcgccg tgggatccgg aggatccgga   9960
gctacgaatt tcagtttgtt gaaacaagcg ggcgatgtcg aagaaaaccc cggccccatg   10020
aagttatggg atgtcgtggc tgtctgcctg gtgctgctcc acaccgcgtc cgccttcccg   10080
ctgcccgccg gtaagaggcc tcccgaggcg cccgccgaag accgctccct cggccgccgc   10140
cgcgcgccct tcgcgctgag cagtgactca aatatgccag aggattatcc tgatcagttc   10200
gatgatgtca tggatttat tcaagccacc attaaaagac tgaaaaggtc accagataaa   10260
```

```
caaatggcag tgcttcctag aagagagcgg aatcggcagg ctgcagctgc caacccagag    10320
aattccagag gaaaaggtcg gagaggccag aggggcaaaa accggggttg tgtcttaact    10380
gcaatacatt taaatgtcac tgacttgggt ctgggctatg aaaccaagga ggaactgatt    10440
tttaggtact gcagcggctc ttgcgatgca gctgagacaa cgtacgacaa aatattgaaa    10500
aacttatcca gaaatagaag gctggtgagt gacaaagtag ggcaggcatg ttgcagaccc    10560
atcgcctttg atgatgacct gtcgttttta gatgataacc tggtttacca tattctaaga    10620
aagcattccg ctaaaaggtg tggatgtatc tgattcgaaa gccgcactcc tcataatcaa    10680
cctctggatt acaaaatttg tgaaagattg actggtattc ttaactatgt tgctcctttt    10740
acgctatgtg gatacgctgc tttaatgcct ttgtatcatg ctattgcttc ccgtatggct    10800
ttcattttct cctccttgta taaatcctgg ttgctgtctc tttatgagga gttgtggccc    10860
gttgtcaggc aacgtggcgt ggtgtgcact gtgtttgctg acgcaacccc cactggttgg    10920
ggcattgcca ccacctgtca gctcctttcc gggactttcg cttt ccccct ccctattgcc    10980 acggcggaac tcatcgccgc ctgccttgcc cgctgctgga caggggctcg gctgttgggc    11040
actgacaatt ccgtggtgtt gtcggggaaa tcatcgtcct ttccttggct gctcgcctgt    11100
gttgccacct ggattctgcg cgggacgtcc ttctgctacg tcccttcggc cctcaatcca    11160
gcggaccttc cttcccgcgg cctgctgccg gctctgcggc ctcttccgcg tcttcgcctt    11220
cgccctcaga cgagtcggat ctccctttgg gccgcctccc cgcttaatta acttcgaact    11280
agggataaca gggtaatctc gactgtgcct tctagaaatt taaatcctcg agggccgcac    11340
tcctcagccg ctgtaagtct gcagaaattg atgatctatt aaacaataaa gatgtccact    11400
aaaatggaag ttttttcctgt catactttgt taagaagggt gagaacagag tacctacatt    11460
ttgaatggaa ggattggagc tacggggtg ggggtgggt gggattagat aaatgcctgc    11520
tctttactga aggctcttta ctattgcttt atgataatgt tcatagttg gatatcataa    11580 tttaaacaag caaaaccaaa ttaagggcca gctcattcct cccactcatg atctatagat    11640
ctatagatct ctcgtgggat cattgttttt ctcttgattc ccactttgtg gttctaagta    11700
ctgtggtttc caaatgtgtc agtttcatag cctgaagaac gagatcagca gcctctgttc    11760
cacatacact tcattctcag tattgttttg ccaagttcta attccatcag aagcttggat    11820
cctctagcga taagcttgat atcgaattcg agttggcgcg cctgtcattc taaatctctc    11880
tttcagccta aagcttttc cccgtatccc cccaggtgtc tgcaggctca aagagcagcg    11940
agaagcgttc agaggaaagc gatcccgtgc caccttcccc gtgcccgggc tgtccccgca    12000
cgctgccggc tcggggatgc gggggagcg ccggaccgga gcggagcccc gggcggctcg    12060
ctgctgcccc ctagcggggg agggacgtaa ttacatccct gggggctttg ggaggggct    12120 gtccccgtga gctccaggc gcgcctgtca ttctaaatct ctctttcagc ctaaagcttt    12180
ttccccgtat cccccaggt gtctgcaggc tcaaagagca gcgagaagcg ttcagaggaa    12240
agcgatcccg tgccaccttc cccgtgcccg ggctgtcccc gcacgctgcc ggctcgggga    12300
tgcgggggga gcgccggacc ggagcggagc ccgggcggc tcgctgctgc ccctagcgg    12360 gggagggacg taattacatc cctggggct tggggggg gctgtccccg tgagctcaat    12420
aaaagagccc acaacccctc actcggcgcg ccagtcctcc gatagactgc gtcgcccggg    12480
tacccgtgta tccaataaac cctcttgcag cctgcaggaa gttcctattc tctagaaagt    12540
ataggaactt caagcttggc gtaatcatgg tcatagctgt ttcctgtgtg aaattgttat    12600
ccgctcacaa ttccacacaa catacgagcc ggaagcataa agtgtaaagc ctggggtgcc    12660
```

```
taatgagtga gctaactcac attaattgcg ttgcgctcac tgcccgcttt ccagtcggga    12720
aacctgtcgt gccagcggat ccgcatctca attagtcagc aaccatagtc ccgcccctaa    12780
ctccgcccat cccgcccta actccgccca gttccgccca ttctccgccc catggctgac     12840
taattttttt tatttatgca gaggccgagg ccgcctcggc ctctgagcta ttccagaagt    12900
agtgaggagg cttttttgga ggcctaggct tttgcaaaaa gctaacttgt ttattgcagc    12960
ttataatggt tacaaataaa gcaatagcat cacaaatttc acaaataaag cattttttc     13020 actgcattct agttgtggtt tgtccaaact catcaatgta tcttatcatg tctggatccg    13080
ctgcattaat gaatcggcca acgcgcgggg agaggcggtt tgcgtattgg gcgctcttcc    13140
gcttcctcgc tcactgactc gctgcgctcg tcgttcggc tgcggcgagc ggtatcagct     13200
cactcaaagg cggtaatacg gttatccaca gaatcagggg ataacgcagg aaagaacatg    13260
tgagcaaaag gccagcaaaa ggccaggaac cgtaaaaagg ccgcgttgct ggcgttttc     13320 cataggctcc gcccccctga cgagcatcac aaaaatcgac gctcaagtca gaggtggcga    13380
aacccgacag gactataaag ataccaggcg tttccccctg gaagctccct cgtgcgctct    13440
cctgttccga ccctgccgct taccggatac ctgtccgcct ttctcccttc gggaagcgtg    13500
gcgctttctc atagctcacg ctgtaggtat ctcagttcgg tgtaggtcgt tcgctccaag    13560
ctgggctgtg tgcacgaacc ccccgttcag cccgaccgct gcgccttatc cggtaactat    13620
cgtcttgagt ccaacccggt aagacacgac ttatcgccac tggcagcagc cactggtaac    13680
aggattagca gagcgaggta tgtaggcggt gctacagagt tcttgaagtg gtggcctaac    13740
tacggctaca ctagaagaac agtatttggt atctgcgctc tgctgaagcc agttaccttc    13800
ggaaaaagag ttggtagctc ttgatccggc aaacaaacca ccgctggtag cggtggtttt    13860
tttgtttgca agcagcagat tacgcgcaga aaaaaaggat ctcaagaaga tcctttgatc    13920
ttttctacgg ggtctgacgc tcagtggaac gaaaactcac gttaagggat tttggtcatg    13980
agattatcaa aaaggatctt cacctagatc cttttaaatt aaaaatgaag ttttaaatca    14040
atctaaagta tatatgagta aacttggtct gacagttacc aatgcttaat cagtgaggca    14100
cctatctcag cgatctgtct atttcgttca tccatagttg cctgactccc cgtcgtgtag    14160
ataactacga tacgggaggg cttaccatct ggccccagtg ctgcaatgat accgcgagac    14220
ccacgctcac cggctccaga tttatcagca ataaaccagc cagccggaag ggccgagcgc    14280
agaagtggtc ctgcaacttt atccgcctcc atccagtcta ttaattgttg ccgggaagct    14340
agagtaagta gttcgccagt taatagtttg cgcaacgttg ttgccattgc tacaggcatc    14400
gtggtgtcac gctcgtcgtt tggtatggct tcattcagct ccggttccca acgatcaagg    14460
cgagttacat gatcccccat gttgtgcaaa aaagcggtta gctccttcgg tcctccgatc    14520
gttgtcagaa gtaagttggc cgcagtgtta tcactcatgg ttatggcagc actgcataat    14580
tctcttactg tcatgccatc cgtaagatgc ttttctgtga ctggtgagta ctcaaccaag    14640
tcattctgag aatagtgtat gcggcgaccg agttgctctt gcccggcgtc aatacgggat    14700
aataccgcgc cacatagcag aactttaaaa gtgctcatca ttggaaaacg ttcttcgggg    14760
cgaaaactct caaggatctt accgctgttg agatccagtt cgatgtaacc cactcgtgca    14820
cccaactgat cttcagcatc ttttactttc accagcgttt ctgggtgagc aaaaacagga    14880
aggcaaaatg ccgcaaaaaa gggaataagg gcgacacgga aatgttgaat actcatactc    14940
```

```
ttccttttc  aatattattg  aagcatttat  cagggttatt  gtctcatgag  cggatacata  15000
tttgaatgta  tttagaaaaa  taaacaaata  ggggttccgc  gcacatttcc  ccgaaaagtg  15060
ccacctg                                                                15067
```